US007232666B2

(12) United States Patent
Sharpe et al.

(10) Patent No.: US 7,232,666 B2
(45) Date of Patent: Jun. 19, 2007

(54) **OPTIMIZED BACTERIAL HOST STRAINS OF *METHYLOMONAS SP.* 16A**

(75) Inventors: Pamela L. Sharpe, Newark, DE (US); Qiong Cheng, Wilmington, DE (US); Melissa D. Bosak, Deptford, NJ (US); Luan Tao, Claymont, DE (US); Natalia Sedkova, Cherry Hill, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 45 days.

(21) Appl. No.: 10/997,844

(22) Filed: Nov. 24, 2004

(65) Prior Publication Data

US 2005/0124033 A1 Jun. 9, 2005

Related U.S. Application Data

(60) Provisional application No. 60/527,877, filed on Dec. 8, 2003, provisional application No. 60/527,083, filed on Dec. 3, 2003.

(51) Int. Cl.
*C12P 23/00* (2006.01)
*C07H 21/04* (2006.01)
*C12N 9/10* (2006.01)
*C12N 15/74* (2006.01)
*C12N 1/21* (2006.01)

(52) U.S. Cl. ............... 435/67; 435/193; 435/252.3; 435/471; 435/69.1; 536/23.2

(58) Field of Classification Search ............ 435/67, 435/193, 252.3, 471, 69.1; 536/23.2
See application file for complete search history.

(56) References Cited

U.S. PATENT DOCUMENTS

| 6,537,786 B2 | 3/2003 | Koffas et al. |
| 6,660,507 B2 | 12/2003 | Cheng et al. |
| 6,689,601 B2 * | 2/2004 | Koffas et al. ............... 435/247 |
| 6,929,928 B2 | 8/2005 | Cheng et al. |
| 2002/0102690 A1 * | 8/2002 | Cheng et al. ............... 435/193 |
| 2003/0003528 A1 | 1/2003 | Brzostowicz et al. |

FOREIGN PATENT DOCUMENTS

| WO | WO 02/18617 A2 * | 3/2002 | ............... 435/193 |

OTHER PUBLICATIONS

National Center for Biotechnology Information General Identifier No. 2224840, Accession No: X73889, Mar. 10, 2001, B. Wieland et al., Genetic and Biochemical Analyses of the Biosynthesis of the Yellow Carotenoid 4,4'-Diaponeurosporene of *Staphylococcus aureus*.

National Center for Biotechnology Information General Identifier No. 57634611, Accession No: NC_002758, Jan. 19, 2005, M. Kuroda et al., Whole Genome Sequencing of Meticillin-Resistant *Staphylococcus aureus*.

National Center for Biotechnology Information General Identifier No. 29165615, Accession No: NC_002745, Jan. 27, 2005, M. Kuroda et al., Whole Genome Sequencing of Meticillin-Resistant *Staphylococcus aureus*.

Axel Raisig et al., 4,4'-Diapophytoene Desaturase: Catalytic Properties of an Enzyme from the C30 Carotenoid Pathway of *Staphylococcus aureus*, Journal of Bacteriology, vol. 181(19):6184-6187, Oct. 1999.

John J. Kilbane, A Biosystem for Removal of Metal Ions from Water, Gas, Oil, Coal, Enviorn. Biotechnol., 3[Pap. IGT's Int. Symp.], 3rd ed., Meeting Date 1990, Akin, C. and J. Smith, Eds., IGT: Chicago, IL (1991); pp. 207-226.

Teizi Urakami et al., Occurrence of Isoprenoid Compounds in Gram-Negative Methanol-,Methane-, and Methylamine-Utilizing Bacteria, J. Gen. Appl. Microbio., vol. 32:317-341, 1986.

Brend Wieland et al., Genetic and Biochemical Analyses of the Biosynthesis of the Yellow Carotenoid 4,4'-Diaponeurosporene of *Staphylococcus aureus*, Journal of Bacteriology, vol. 178(24):7719-7726, Dec. 1994.

Ivanova et al., Mikrobiologiya, vol. 57(4):600-605, 1988.

National Center for Biotechnology Information General Identifier No. 14349229, Accession No: AP003137, Jan. 11, 2003, M. Kuroda et al., Whole Genome Sequencing of Meticillin-Resistant *Staphylococcus aureus*.

National Center for Biotechnology Information General Identifier No. 46395552, Accession No: AP003365, Apr. 17, 2004, M. Kuroda et al., Whole Genome Sequencing of Meticillin-Resistant *Staphylococcus aureus*.

* cited by examiner

*Primary Examiner*—Kathleen M. Kerr
*Assistant Examiner*—Kagnew Gebreyesus

(57) ABSTRACT

Methanotrophic bacterial strains are provided that have been optimized for the production of carotenoid compounds through the down-regulation of one or more of the crtN1, ald, crtN2 and crtN3 genes of the carotenoid biosynthetic pathway. The resulting strains lack pigmented $C_{30}$ carotenoid compounds, and show an increase in the production of $C_{40}$ carotenoids. The use of the optimized host strains for the production of the $C_{40}$ carotenoids canthaxanthin and astaxanthin is also described.

7 Claims, 8 Drawing Sheets

```
                        1                                                 50
wt Agro crtW    (1)                     ATGAGCGGACATGCCCTGCCCAAGCCAGA
syn Agro crtW   (1)     CAATTGAAGGAGGAATAAACCATGAGCGGCCATGCCCTGCCGAAAGCCGA 51                                                100
wt Agro crtW    (51)    TCTGACCGCCACCAGCCTGATCGTCTCGGGCGGCATCATCGCCGCTTGCC
syn Agro crtW   (51)    CCTGACCGCGACCAGCCTGATCGTCAGCGGTGGCATCATCGCGGCCTGCC 101                                               150
wt Agro crtW    (101)   TGGCCCTGCATGTGCATGCCGTGTGGTTTCTGGACGGAGCGGCGCATCGC
syn Agro crtW   (101)   TGGCGCTGCATGTCCATGCCCTGTGGTTCCTGGACGGCGCCGCCATCCG 151                                               200
wt Agro crtW    (151)   ATCCTGGCGATCGCAAATTTCCTGGGGCTGACCTGCTGTCGGTCGGATT
syn Agro crtW   (151)   ATCCTGGCCATCGCCAACTTCCTGGGCCTGACCTGGCTGAGCGTCGGCCT 201                                               250
wt Agro crtW    (201)   GTTCATCATCGCGCATGACGGATGCACGGGTCGGTGGTGCCGGGGCGTC
syn Agro crtW   (201)   GTTCATCATCGGCATCACGGCATGCATGGCAGCGTGGTCCGGGGTCGTC 251                                               300
wt Agro crtW    (251)   CCCGCGCCAATGGCGCGATGCGCCAGCTTGTCCTGTCGCTGTATGCGGGA
syn Agro crtW   (251)   CCCGTGCCAACGGCCGCCATGCCCCAAGTGGTCCTGTCGTTGTATGCGGC 301                                               350
wt Agro crtW    (301)   TTTCGCTGGCGCAAGATCATCGTCAAGCACATGCCCCATCACGGGCATGC
syn Agro crtW   (301)   TTCAGCTGGCGCAAGATCATCGTCAACATATGCCCCATCATCGGCACCGG 351                                               400
wt Agro crtW    (351)   CGGAACCGACGACGACCGCGATTTCCACCATCGCCGCCCGGTCCGCTGGT
syn Agro crtW   (351)   GGGCACCGACGACGATCGGCACTTCCACCATCGTCGCCCGGTCCGCTGGT 401                                               450
wt Agro crtW    (401)   ACGCCGGCTTCATCGGCAGCTATTTCGGCTGCCGCAGCGGCTGCTCCTG
syn Agro crtW   (401)   ATGCGGGCTTCATCGGCACCTATTTCGGGCTGCCCTGAAGGCCTGTTGCTC 451                                               500
wt Agro crtW    (451)   CCCGTCATCGTGACGGTCTATGCGCTGATCCTTCGGCATCGGTCGATGTA
syn Agro crtW   (451)   CCGGTCATCGTCACCGTCTATGCCCTGATCCTGGGCCGACGGTGGATGTA 501                                               550
wt Agro crtW    (501)   CCTGGTCTTCTGGCCGGCTGCCGTCGATCCTGGCCGTCGATGCACCTGTTCC
syn Agro crtW   (501)   TGTCGTCTTCTGGCCGGCTGCCGAGCATCCTGGCCAGCATCCAACTGTTCC 551                                               600
wt Agro crtW    (551)   TGTTCGGCCAGCTGGCTGCCGCACCGCCCGGGCACGAGCGTTCCCGGAC
syn Agro crtW   (551)   TCTTCGGTACCTGGCTGCCGCATCGCCCGGGCCATGACGGCTTTCCCGGAC 601                                               650
wt Agro crtW    (601)   CCGCACAATGGCGCGGTCGTCGGGGATCAGGCGACCCGTGTCGCTGCTGAC
syn Agro crtW   (601)   CCCCATAACGGCCGGCAGCAGCGGCATCAGCGACCGGGTCAGCCTGCTGAC 651                                               700
wt Agro crtW    (651)   CTGCTTTCACTTTGGCGGTTATCATCACGAACACCACGTGCACCCGGACGG
syn Agro crtW   (651)   CTGCTTCCATTTCGGCGGCTATCATCATGAACATCATCTGCATCCGGACCG 701                                               750
wt Agro crtW    (701)   TGCCCGTGGTGGCGGCCTGCCCAGCACCCGCACCAAGGGGACACGGCATGA
syn Agro crtW   (701)   TCCCGTGGTGGCGGCCTGCCCGAGCACCCGCACCAAAGGCGACACGGCTGA 751
wt Agro crtW    (751)
syn Agro crtW   (751)   CAATTG
```

Figure 6

```
1                                                                50
  wt agro crtZ   (1) ---------------------------ATGACCAATTTGCTGATCGT
  syn agro crtZ  (1) CAATTGTGCTCTAGAAAGGAGGAATAAACCATGACCAACTTCCTGATCGT 51                                              100
  wt agro crtZ  (21) CGTCGCCACCGTGCTGGTGATGGAGTTGACGGCCTATTCGGTCCACCGCT
  syn agro crtZ (51) CGTCGCCACCGTGCTGGTCATGGAACTGACCGCGTATAGCGTCCATCCTT 101                                             150
  wt agro crtZ  (71) GGATCATGCACGGCCGCCTGGCCTGGGCGTGGCACAAGTCCCACCACGAG
  syn agro crtZ (101) GGATCATGCATGGTCCGTTGGCGTGGGCGTGGCACAAGAGCCATCATCA 151                                             200
  wt agro crtZ (121) CAACACCACCGGCTGGAAAAGAACGACCTGTACGGGCTGGTCTTTGC
  syn agro crtZ (151) CAACATCACCATGCCTTGGAAAAGAATGACCTGTATGGGTTGGTCTTCGC 201                                             250
  wt agro crtZ (171) GGTGATCGCCACGGTGCTGTTCACGGTGGCCTGCATCTGGGGCGCGGTC
  syn agro crtZ (201) CGTCATCGCCAGCGTCCTGTTCACCGTCGCCTGCATCTGGGCCTCAGTGT 251                                             300
  wt agro crtZ (221) TGTCGTCGATCGCCTTGGGCATGACTCGCCTATGGCCTGATCTATTTCGTC
  syn agro crtZ (251) TGTCCTCGATCGCCTTGGGCATGACCCGTCTATGGCTTCATCTACTTCGTC 301                                             350
  wt agro crtZ (271) GTGCATGACGGGCTGCTGCATCAGCGGCTGGCCCGTCCGTGATATCGGCCG
  syn agro crtZ (301) GTGCATGATGGCTTGGTCCATCAAGGCTGGCCGTTCGCCTACATCCGGCG 351                                             400
  wt agro crtZ (321) CAAGGCCTATCGCAGAGCGCTGTATCAGCCCCACCGGCTGCACCACCGG
  syn agro crtZ (351) CATAGGCTATGCCCGTGGCTTGTATCAGCCCATCGGTTGCATCATGCCG 401                                             450
  wt agro crtZ (371) TCGACGGGCGCCGACCATGCGTCAGCTCGGCTTCATCTATCGCGCCCCG
  syn agro crtZ (401) TCGAAGGTCCTGATCATTGCGTCAGCTTGGCTTCATCTATCGCCGACG 451                                             500
  wt agro crtZ (421) GTCCACAAGGTGAAGCAGCACCTGAACATGTCGCCGCGCTCCGGCCCA
  syn agro crtZ (451) GTCCACTAGCTGAAACAAGACCTGAACATGAGCGCGCGCTTCGCGTGCCA 501           533
  wt agro crtZ (471) GCCGCAGCAGCGCACGTGA-------------
  syn agro crtZ (501) AGCCCAAGCAGCGCAGCTAATAGATCTGGAATTC
```

OPTIMIZED BACTERIAL HOST STRAINS OF *METHYLOMONAS SP.* 16A

This application claims the benefit of U.S. Provisional Application No. 60/527,083 filed Dec. 3, 2003 and U.S. Provisional Application No. 60/527,877 filed Dec. 8, 2003.

FIELD OF THE INVENTION

The invention relates to the field of microbiology and molecular biology. More specifically, the invention relates to methanotrophic bacterial host strains optimized for the production of carotenoid compounds through the down-regulation of various genes in the carotenoid biosynthetic pathway.

BACKGROUND OF THE INVENTION

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass;

Obligate methylotrophs are those organisms which are limited to the use of organic compounds that do not contain carbon-carbon bonds for the generation of energy; and Obligate methanotrophs are those obligate methylotrophs that have the distinct ability to oxidize methane.

The ability of obligate methanotrophic bacteria to use methane as their sole source of carbon and energy under ambient conditions, in conjunction with the abundance of methane, makes the biotransformation of methane a potentially unique and valuable process. As such, several have attempted to harness the unique natural abilities of these organisms for commercial applications. For example, the commercial applications for the biotransformation of methane have historically fallen broadly into three categories: 1.) production of single cell protein; 2.) epoxidation of alkenes for production of chemicals; and 3.) biodegradation of chlorinated pollutants. Of these, only epoxidation of alkenes has experienced some commercial success; however, the success has been limited due to low product yields, toxicity of products, and the large amount of cell mass required to generate products. Large-scale protein production from methane, termed single cell protein (or "SCP"), has been technically feasible and commercialized at large scale (Villadsen, J., *Recent Trends Chem. React Eng., [Proc. Int. Chem. React. Eng. Conf.]*, 2$^{nd}$ ed.; Kulkarni, B. D., Mashelkar, R. A., and Sharma, M. M., Eds.; Wiley East: New Delhi, India (1987); Vol 2, pp 320-33). However, SCP has not been economically successful thus far due to the relatively high cost of producing microbial protein, as compared to agriculturally derived protein (i.e., soy protein). This makes SCP a relatively low value product whose economic production cannot tolerate heavy bioprocessing costs. Thus, the yield of the methanotrophic strain used for producing SCP may be critical to the overall economic viability of the process. Microbial biomass produced by methanotrophic bacteria is typically very high in protein content (~70-80% by weight), which can restrict the direct use of this protein to certain types of animal feed.

In addition to the synthesis of SCP, methanotrophic cells can further build the oxidation products of methane (i.e., methanol and formaldehyde) into complex molecules such as carbohydrates and lipids. For example, under certain conditions methanotrophs are known to produce exopolysaccharides (U.S. Pat. No. 6,537,786; U.S. Pat. No. 6,689,601; Ivanova et al., *Mikrobiologiya*, 57(4):600-5 (1988); Kilbane, John J., II, Gas, *Oil, Coal, Environ. Biotechnol.* 3, [Pap. IGT's Int. Symp.], 3$^{rd}$ ed., Meeting Date 1990; Akin, C. and J. Smith, Eds; IGT: Chicago, Ill. (1991); pp 207-26). Similarly, methanotrophs are known to accumulate both isoprenoid compounds and carotenoid pigments of various carbon lengths (U.S. Pat. No. 6,660,507; U.S. Pat. No. 6,689,601; Urakami et. al., *J. Gen. Appl. Microbiol.*, 32(4):317-41 (1986)).

Most recently, the natural abilities of methanotrophic organisms have been extended by the advances of genetic engineering. Odom et al. have investigated *Methylomonas* sp. 16a as a microbial platform of choice for production of a variety of materials beyond single cell protein, including carbohydrates, pigments, terpenoid compounds and aromatic compounds (U.S. Pat. No. 6,689,601 and U.S. Ser. No. 09/941,947, herein incorporated entirely by reference). This particular pink-pigmented methanotrophic bacterial strain is capable of efficiently using either methanol or methane as a carbon substrate, is metabolically versatile in that it contains multiple pathways for the incorporation of carbon from formaldehyde into 3-carbon units, and is capable of genetic exchange with donor species such as *Escherichia coli* via bacterial conjugation. Thus, *Methylomonas* sp. 16a can be engineered to produce new classes of products other than those naturally produced from methane. Further advancement in the metabolic engineering of this particular host organism for production of various commercial products on an economic scale, however, requires some optimization of the host organism. Specifically, it would be desirable to knockout the native carotenoid pathway of the organism leading to the production of pink-pigmented $C_{30}$ carotenoids, increasing the available carbon flux directed toward the products of interest. These modified host organisms should preferably lack antibiotic markers, since the presence of antibiotic resistance genes in the modified host organism could be undesirable in many food and feed applications. The problem to be solved, therefore, is to develop an optimized non-pigmented *Methylomonas* sp. 16a bacterial host organism lacking antibiotic markers for production of various commercial products on an economic scale.

The present problem has been solved through the development of a suite of optimized non-pigmented *Methylomonas* sp. 16a bacterial host organisms, each lacking antibiotic markers. These bacterial hosts were created by investigation of allelic exchange mutations within the native crt gene cluster (comprising the crtN1, ald, and crtN2 genes) and the crtN3 gene of *Methylomonas* sp. 16a, each of which is associated in the biosynthesis of native $C_{30}$ carotenoids in the organism. An efficient means of generating defined mutants by homologous recombination permitted transformants that have undergone allelic exchange to be selected based on a positive selection strategy. This methodology also enabled production of "markerless" transformants and permitted multiple rounds of mutation to be performed.

SUMMARY OF THE INVENTION

The present invention provides optimized C1 metabolizing host cells useful for the production of carotenoid compounds and particularly $C_{40}$ carotenoids. In one embodiment, the optimized host cells of the invention are preferably methanotrophs comprised of a functional Embden-Meyerhof carbon pathway, making them particularly effective in the use of carbon for carotenoid production. Additionally, the host cells have mutations in at least one of the crtN1, ald, crtN2, and crtN3 genes, resulting in the down-regulation and/or complete disruption of the genes. Disruption of one or more of these genes increased production of downstream carotenoids through the re-allocation of carbon in the cells.

Accordingly, the invention provides a high growth methanotrophic bacterial strain which:
 a) grows on a C1 carbon substrate selected from the group consisting of methanol and methane;
 b) comprises a functional Embden-Meyerhof carbon pathway, said pathway comprising a gene encoding a pyrophosphate dependent phosphofructokinase enzyme; and
 c) possesses a disruption such that at least one endogenous gene selected from the group consisting of crtN1, ald, crtN2, and crtN3 is down-regulated.

In a specific embodiment, the invention provides a *Methylomonas* sp. strain optimized for the production of $C_{40}$ carotenoids selected from the group consisting of: MWM1000 (Δald(crtN1)), MWM1100 (Δcrt cluster promoter), MWM1400 (ΔcrtN1), MWM1200 (Δcrt cluster promoter+ΔcrtN3), MWM1600 (Δcrt cluster), MWM1800 (ΔcrtN1+ΔcrtN3), MWM1900 (Δcrt cluster+ΔcrtN3), and MWM1300 (Δald(crtN1)+ΔcrtN3).

In a preferred embodiment, the invention provides a method for the production of $C_{40}$ carotenoids, comprising:
 a) providing the high growth methanotrophic bacterial strain of the invention comprising at least one gene encoding an enzyme of the $C_{40}$ carotenoid biosynthesis pathway;
 b) growing the bacterial strain of step (a) under conditions wherein the gene encoding an enzyme of the $C_{40}$ carotenoid biosynthesis pathway is expressed producing a $C_{40}$ carotenoid; and
 c) optionally recovering the $C_{40}$ carotenoid.

In an alternate embodiment, the invention provides a method for the production of canthaxanthin comprising:
 (a) providing a high growth methanotrophic bacterial strain comprising:
  i) a functional Embden-Meyerhof carbon pathway, said pathway comprising a gene encoding a pyrophosphate dependent phosphofructokinase enzyme; and
  ii) a disruption in at least one endogenous gene selected from the group consisting of crtN1, ald, crtN2, and crtN3;
  iii) a crtE-idi-crtY-crtI-crtB gene cluster having the sequence as set forth in SEQ ID NO:6; and
  iv) a codon-optimized β-carotene ketolase gene having the sequence as set forth in SEQ ID NO:7;
  wherein said high growth methanotrophic bacterial strain grows on a C1 carbon substrate selected from the group consisting of methanol and methane;
 (b) growing the high growth methanotrophic bacterial strain of step (a) under conditions wherein the crtE-idi-crtY-crtI-crtB gene cluster genes and the codon-optimized β-carotene ketolase gene are expressed producing canthaxanthin; and
 (c) optionally recovering the canthaxanthin.

Similarly, the invention provides a method for the production of astaxanthin comprising:
 (a) providing a high growth methanotrophic bacterial strain comprising:
  i) a functional Embden-Meyerhof carbon pathway, said pathway comprising a gene encoding a pyrophosphate dependent phosphofructokinase enzyme; and
  ii) a disruption in at least one endogenous gene selected from the group consisting of crtN1, ald, crtN2, and crtN3;
  iii) a crtE-idi-crtY-crtI-crtB gene cluster having the sequence as set forth in SEQ ID NO:6;
  iv) a codon-optimized β-carotene ketolase gene having the sequence as set forth in SEQ ID NO:7; and
  (v) a codon-optimized β-carotene hydroxylase gene having the sequence as set forth in SEQ ID NO:8;
  wherein said high growth methanotrophic bacterial strain grows on a C1 carbon substrate selected from the group consisting of methanol and methane;
 (b) growing the high growth methanotrophic bacterial strain of step (a) under conditions wherein the crtE-idi-crtY-crtI-crtB gene cluster genes, the codon-optimized β-carotene ketolase gene, and the codon-optimized β-carotene hydroxylase gene are expressed producing astaxanthin; and
 (c) optionally recovering the astaxanthin.

Additionally the invention provides an isolated nucleic acid molecule selected from the group consisting of:
 (a) an isolated nucleic acid molecule as set forth in SEQ ID NO:7 which encodes a β-carotene ketolase enzyme; and
 (b) an isolated nucleic acid molecule that is completely complementary to (a).

Similarly, the invention provides an isolated nucleic acid molecule which encodes a β-carotene ketolase enzyme as set forth in SEQ ID NO:33 wherein at least 99 codons are codon-optimized for expression in *Methylomonas* sp.

In another embodiment the invention provides an isolated nucleic acid molecule selected from the group consisting of:
 (a) an isolated nucleic acid molecule as set forth in SEQ ID NO:8 which encodes a β-carotene hydroxylase enzyme; and
 (b) an isolated nucleic acid molecule that is completely complementary to (a).

Additionally, the invention provides an isolated nucleic acid molecule which encodes a β-carotene hydroxylase enzyme as set forth in SEQ ID NO:34 wherein at least 73 codons are codon-optimized for expression in *Methylomonas* sp.

BRIEF DESCRIPTION OF THE FIGURES, SEQUENCE DESCRIPTIONS, AND BIOLOGICAL DEPOSITS

FIG. 6 shows a comparison of the codon-optimized crtW gene (SEQ ID NO:7) with the wild-type crtW gene (SEQ ID NO:31) from *Agrobacterium aurantiacum*.

FIG. 7 shows a comparison of the codon-optimized crtZ gene (SEQ ID NO:8) with the wild-type crtZ gene (SEQ ID NO:32) from *Agrobacterium aurantiacum*.

Figure 1:
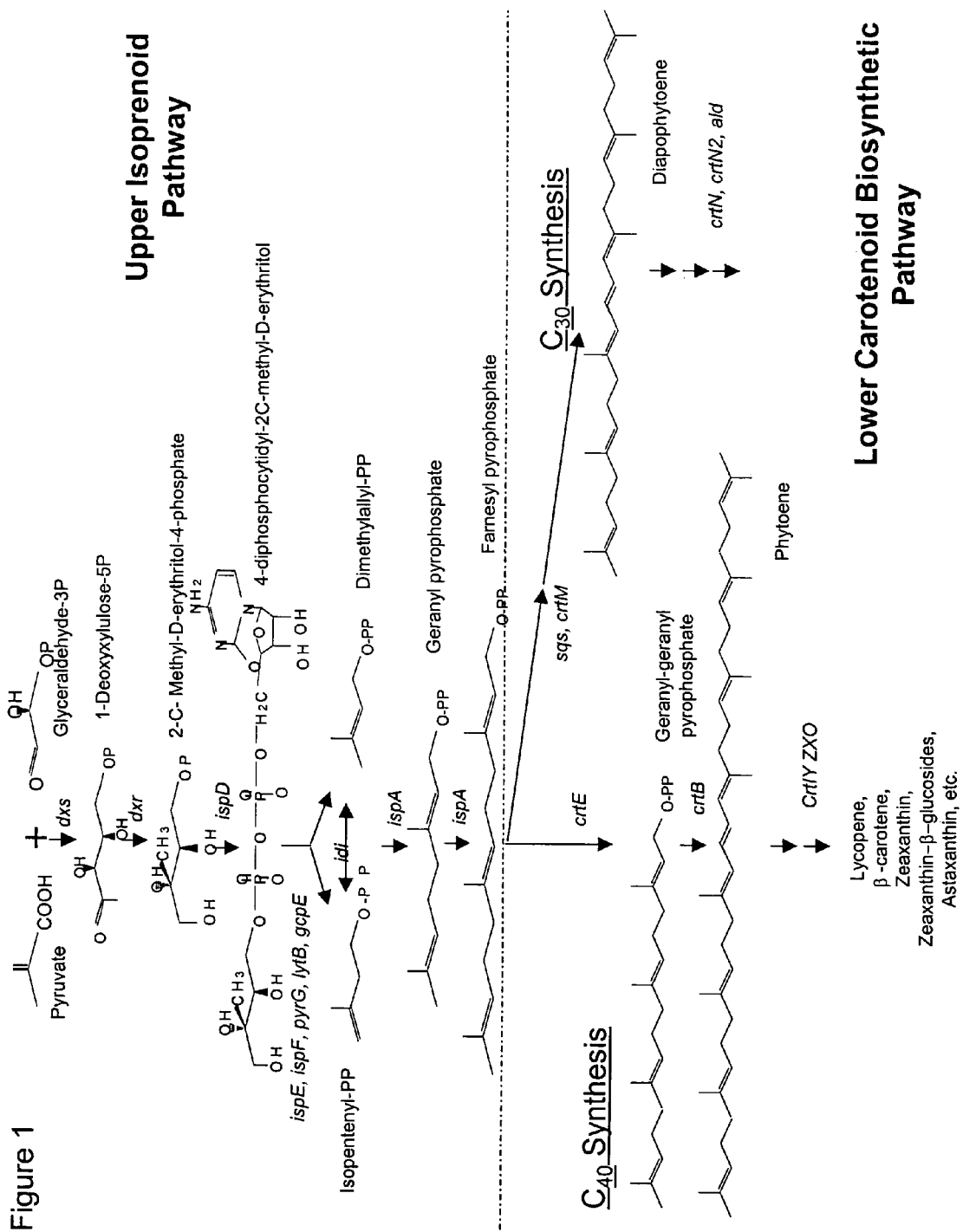
FIG. 1 shows the upper isoprenoid and lower carotenoid biosynthetic pathways.

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the 16S rRNA gene from *Methylomonas* sp. 16a.

SEQ ID NO:2 is the nucleotide sequence of the crtN1 gene from *Methylomonas* sp. 16a.

SEQ ID NO:3 is the nucleotide sequence of the ald gene from *Methylomonas* sp. 16a.

SEQ ID NO:4 is the nucleotide sequence of the crtN2 gene from *Methylomonas* sp. 16a.

SEQ ID NO:5 is the nucleotide sequence of the crtN3 gene from *Methylomonas* sp. 16a.

SEQ ID NO:6 is the nucleotide sequence of the crtE-idi-crtY-crtI-crtB gene cluster from Pantoea agglomerans DC404 (US 10/808,807).

SEQ ID NO:7 is the nucleotide sequence of the codon-optimized β-carotene ketolase gene from *Agrobacterium aurantiacum*.

SEQ ID NO:8 is the nucleotide sequence of the codon-optimized β-carotene hydroxylase gene from *Agrobacterium aurantiacum*.

SEQ ID NOs:9 and 10 are the nucleotide sequences of primers DrdI/npr-sacB and TthIII/npr-sacB, respectively, used for amplification of the npr-sacB cassette from plasmid pBE83, as described in Example 2.

SEQ ID NOs:11-30 and 48-53 are the nucleotide sequences of primers used for cloning of the carotenoid deletion fragments, as described in Example 3 and for confirmation of the mutant constructs as describe in Example 5.

SEQ ID NO:31 is the nucleotide sequence of the wild-type β-carotene ketolase gene from *Agrobacterium aurantiacum*.

SEQ ID NO:32 is the nucleotide sequence of the wild-type β-carotene hydroxylase gene from *Agrobacterium aurantiacum*.

SEQ ID NO:33 is the amino acid sequence of the β-carotene ketolase enzyme from *Agrobacterium aurantiacum*.

SEQ ID NO:34 is the amino acid sequence of the β-carotene hydroxylase enzyme from *Agrobacterium aurantiacum*.

SEQ ID NO:35 is the nucleotide sequence of the crtE gene from *Pantoea stewartii*.

SEQ ID NO:36 is the nucleotide sequence of the crtYIB gene cluster from *Pantoea stewartii*.

SEQ ID NOs:37-40 are the nucleotide sequences of primers used to construct the canthaxanthin expression plasmid pDCQ307, as described in Example 9.

SEQ ID NO:41 is the nucleotide sequence of the crtEidiY-IBZ gene cluster from *Pantoea agglomerans*.

SEQ ID NOs:42 and 43 are the nucleotide sequences of primers used to construct the canthaxanthin expression plasmid pDCQ333, as described in Example 11.

SEQ ID NOs:44-47 are the nucleotide sequences of primers used to construct the astaxanthin expression plasmids pDCQ324 and pDCQ334, as described in Example 12.

Applicants made the following biological deposit under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Definitions

In this disclosure, a number of terms and abbreviations are used. The following definitions are provided.

As used herein, the term "comprising" means the presence of the stated features, integers, steps, or components as referred to in the claims, but that it does not preclude the presence or addition of one or more other features, integers, steps, components or groups thereof.

"Open reading frame" is abbreviated ORF.

"Polymerase chain reaction" is abbreviated PCR.

"High Performance Liquid Chromatography" is abbreviated HPLC.

"Kanamycin" is abbreviated Kan.

"Ampicillin" is abbreviated Amp.

The term "isoprenoid compound" refers to compounds formally derived from isoprene (2-methylbuta-1,3-diene; $CH_2=C(CH_3)CH=CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be, for example, of 5, 10, 15, 20, 30, or 40 carbons in length.

The term "carotenoid biosynthetic pathway" refers to those genes comprising members of the upper isoprenoid pathway and/or lower carotenoid biosynthetic pathway, as illustrated in FIG. 1.

The terms "upper isoprenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methyl-erythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$-$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtR, crtZ, crtW, crtO, crtA, crtC, crtD, crtF, and crtU. Finally, the term "lower carotenoid biosynthetic enzyme" is an inclusive term referring to any and all of the enzymes in the present lower pathway including, but not limited to: CrtM, CrtN, CrtN2, CrtE, CrtX, CrtY, CrtI, CrtB, CrtR, CrtZ, CrtW, CrtO, CrtA, CrtC, CrtD, CrtF, and CrtU.

The term "carotenoid" refers to a class of hydrocarbons having a conjugated polyene carbon skeleton formally derived from isoprene. This class of molecules is composed of $C_{30}$ diapocarotenoids and $C_{40}$ carotenoids and their oxygenated derivatives; and, these molecules typically have strong light absorbing properties.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure (Formula I below, hereinafter referred to as "diapophytoene"), having a long central chain of conjugated double bonds, by: (i) hydrogenation (ii) dehydrogenation, (iii) cyclization, (iv) oxidation, (v) esterification/glycosylation, or any combination of these processes.

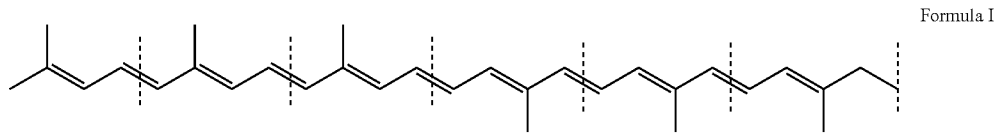

Formula I

"Tetraterpenes" or "$C_{40}$ carotenoias consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

The term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

The term "Idi" refers to an isopentenyl diphosphate isomerase enzyme (E.C. 5.3.3.2) encoded by the idi gene.

The term "CrtY" refers to a lycopene cyclase enzyme encoded by the crY gene which converts lycopene to β-carotene.

The term "CrtI" refers to a phytoene desaturase enzyme encoded by the crtI gene. CrtI converts phytoene into lycopene via the intermediaries of phytofluene, ζ-carotene and neurosporene by the introduction of 4 double bonds.

The term "CrtB" refers to a phytoene synthase enzyme encoded by the crtB gene which catalyzes the reaction from prephytoene diphosphate to phytoene.

The term "CrtZ" refers to a carotenoid hydroxylase enzyme (e.g. β-carotene hydroxylase) encoded by the crtZ gene which catalyzes a hydroxylation reaction. The oxidation reaction adds a hydroxyl group to cyclic carotenoids having a β-ionone type ring. This reaction converts cyclic carotenoids, such as β-carotene or canthaxanthin, into the hydroxylated carotenoids zeaxanthin or astaxanthin, respectively. Intermediates in the process typically include β-cryptoxanthin and adonirubin. It is known that CrtZ hydroxylases typically exhibit substrate flexibility, enabling production of a variety of hydroxylated carotenoids depending upon the available substrates.

The term "CrtW" refers to a β-carotene ketolase enzyme encoded by the crtW gene which catalyzes an oxidation reaction where a keto group is introduced on the β-ionone type ring of cyclic carotenoids. This reaction converts cyclic carotenoids, such as β-carotene or zeaxanthin, into the ketocarotenoids canthaxanthin or astaxanthin, respectively. Intermediates in the process typically include echinenone and adonixanthin. It is known that CrtW ketolases typically exhibit substrate flexibility.

The term "CrtX" refers to a zeaxanthin glucosyl transferase enzyme encoded by the crtX gene and which converts zeaxanthin to zeaxanthin-β-diglucoside.

The term "crtE-idi-crtY-crtI-crtB" or "crtE-idi-crtYIB" gene cluster refers to a molecule having the following genetic organization: the crtE, idi, crtY, crtI, and crtB genes are clustered in the order stated.

As used here, the term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In another embodiment, the $C_1$ carbon substrates is selected from the group consisting of methanol and/or methane.

The term "$C_1$ metabolizer" refers to a microorganism that has the ability to use a single carbon substrate as its sole source of energy and biomass. $C_1$ metabolizers will typically be methylotrophs and/or methanotrophs.

The term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph. In one embodiment, the methylotroph uses methanol and/or methane as its primary carbon source.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus*, and *Methylosinus*. In one embodiment, the methanotrophic bacteria uses methane and/or methanol as its primary carbon source.

The term "high growth methanotrophic bacterial strain" refers to a bacterium capable of growth with methane and/or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

The terms "crtN1 gene cluster", "$C_{30}$ crt gene cluster", "crt gene cluster", and "endogenous *Methylomonas* crt gene cluster" refer to an operon comprising crtN1, ald, and crtN2 genes that is active in the native carotenoid biosynthetic pathway of *Methylomonas* sp. 16a.

The term "CrtN1" refers to an enzyme encoded by the crtN1 gene, active in the native carotenoid biosynthetic pathway of *Methylomonas* sp. 16a. This gene is located within an operon comprising crtN2 and ald.

The term "ALD" refers to an enzyme (an aldehyde dehydrogenase) encoded by the ald gene, active in the native carotenoid biosynthetic pathway of *Methylomonas* sp. 16a. This gene is located within an operon comprising crtN1 and crtN2. As used herein, the gene and gene product of the ald gene may be optionally referred to as "aldehyde dehydrogenase".

The term "CrtN2" refers to an enzyme encoded by the crtN2 gene, active in the native carotenoid biosynthetic pathway of *Methylomonas* sp. 16a. This gene is located within an operon comprising crtN1 and ald.

Figure 2:
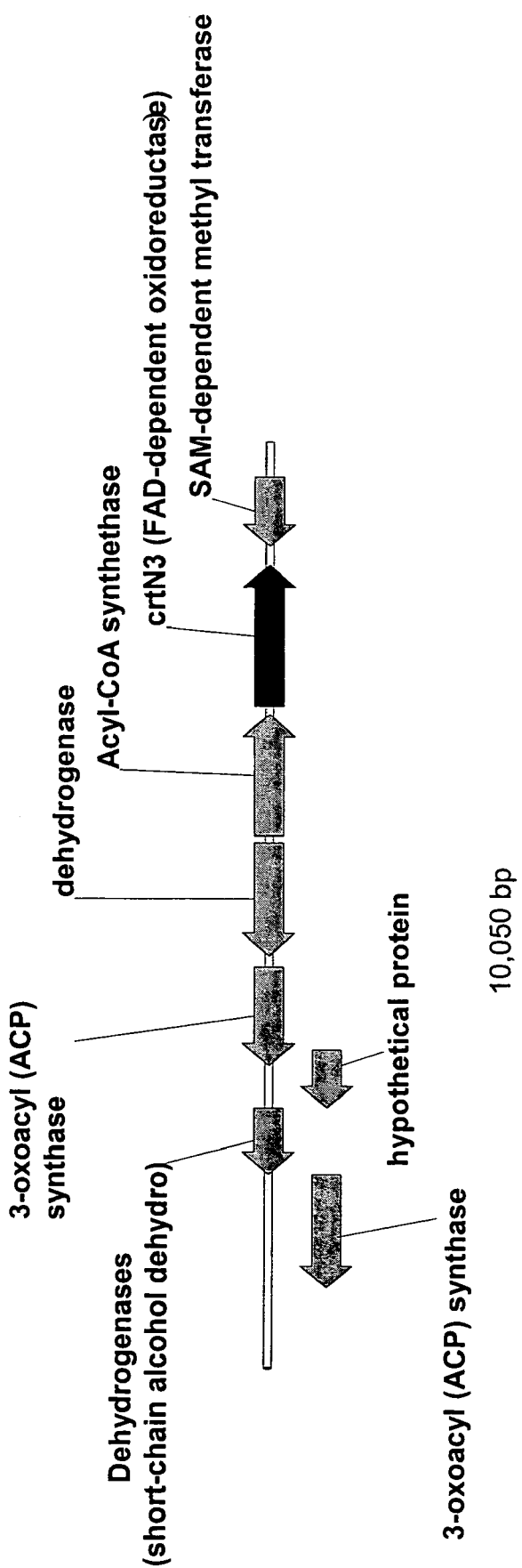
FIG. 2 illustrates the position of the crtN3 gene within *Methylomonas*' genome, with respect to other genes.

The term "CrtN3" refers to an enzyme encoded by the crtN3 gene, active in the native carotenoid biosynthetic pathway of *Methylomonas* sp. 16a. This gene is not located within the crt gene cluster; instead this gene is present in a different location within the *Methylomonas* genome, as illustrated in FIG. 2.

The term "Sqs" refers to the squalene dehydrogenase enzyme encoded by the sqs gene.

The term "pigmentless" or "white mutant" refers to a *Methylomonas* sp. 16a bacterium wherein the native pink pigment (e.g., a $C_{30}$ carotenoid) is not produced. Thus, the bacterial cells appear white in color, as opposed to pink.

The term "positive selection" means a selection method that enables only those cells that carry a DNA insert integrated at a specific chromosomal location to grow under particular conditions. In contrast, negative selection is based on selection methods whereby only those individuals that do not possess a certain character (e.g., cells that do not carry a DNA insert integrated at a specific chromosomal location) are selected.

The term "homologous recombination" refers to the exchange of DNA fragments between two DNA molecules (during cross over). The fragments that are exchanged are flanked by sites of identical nucleotide sequences between the two DNA molecules (i.e., homologous DNA regions). Homologous recombination is the most common means for generated genetic diversity in microbes.

The term "chromosomal integration" means that a chromosomal integration vector becomes congruent with the chromosome of a microorganism through recombination between homologous DNA regions on the chromosomal integration vector and within the chromosome.

The term "chromosomal integration vector" means an extra-chromosomal vector that is capable of integrating into the host's genome through homologous recombination.

The term "suicide vector" or "positive selection vector" refers to a type of chromosomal integration vector that is capable of replicating in one host but not in another. Thus, the vector is conditional for its replication.

The terms "single-crossover event" and "plasmid integration" are used interchangeably and mean the incorporation of a chromosomal integration vector into the genome of a host via homologous recombination between regions of homology between DNA present within the chromosomal integration vector and the host's chromosomal DNA. A "single-crossover mutant" refers to a cell that has undergone a single-crossover event.

Figure 4:
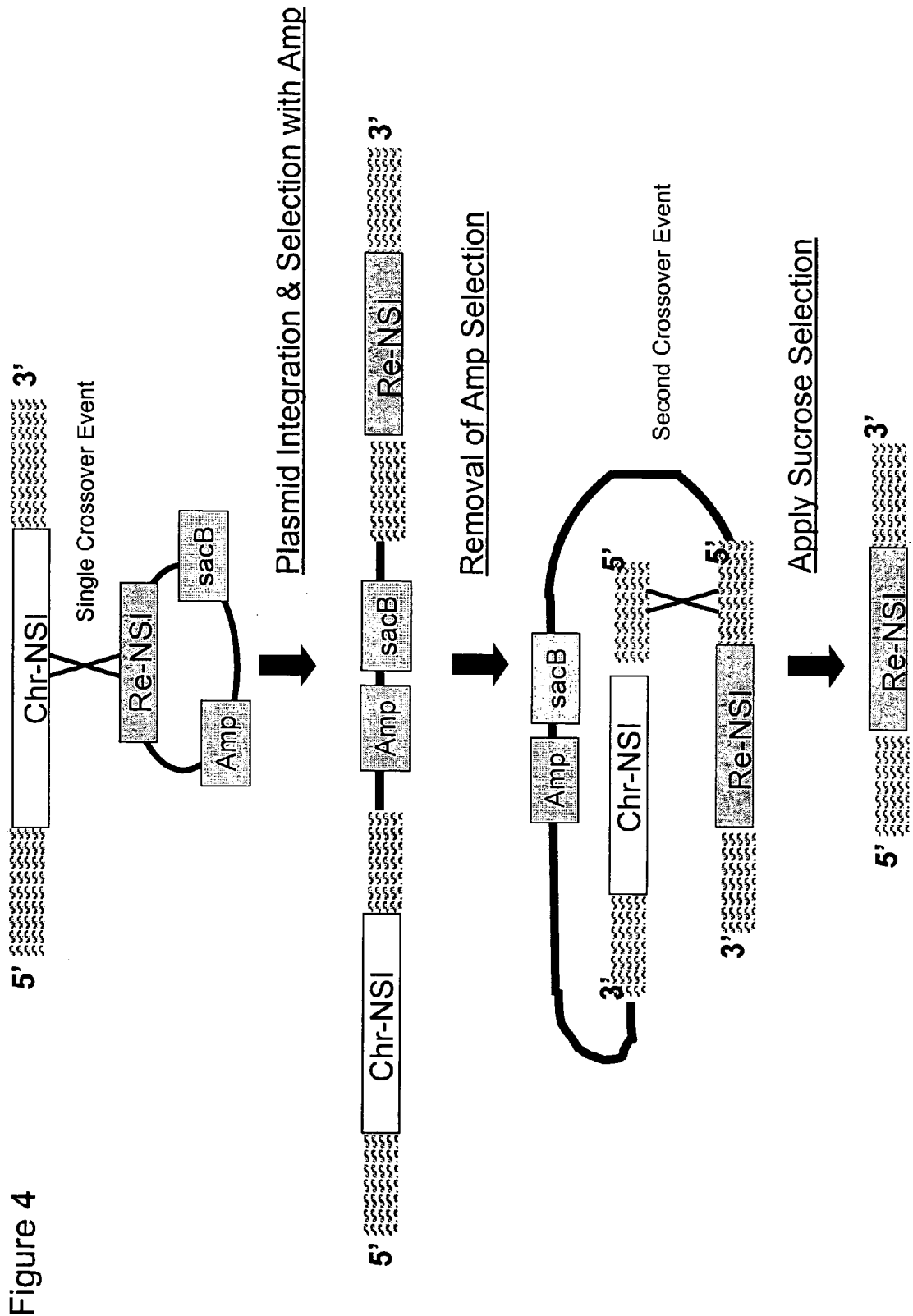
FIG. 4 is a schematic diagram illustrating the two-step selection protocol used for identifying "markerless" double-crossover mutants in C1 metabolizing bacteria.

The terms "double-crossover event", "allelic exchange" and "gene replacement" are used interchangeably and mean the homologous recombination between a DNA region within the chromosomal integration vector and a region within the chromosome that results in the replacement of the functional chromosomal nucleotide sequence of interest (i.e., chr-NSI) with a homologous plasmid region (i.e., the replacement nucleotide sequence of interest, or re-NSI) (FIG. 4). A "double-crossover mutant" or "allelic exchange mutant" is the result of a double-crossover event. This mutant can be generated by two simultaneous reciprocal breakage and reunion events between the same two DNA fragments; alternatively, a double-crossover mutant can be the result of two single-crossovers that occur non-simultaneously.

The term "chromosomal nucleotide sequence of interest" or "chr-NSI" refers to a specific chromosomal sequence that is targeted for homologous recombination. In a preferred embodiment, the chr-NSI encodes one or more of the native crtN1, ald, crtN2, or crtN3 genes of *Methylomonas* sp. 16a; alternatively, the chr-NSI corresponds to the promoter driving the *Methylomonas* sp. 16a crt gene cluster.

The term "replacement nucleotide sequence of interest" or "re-NSI" refers to a nucleotide sequence of interest that is cloned into a chromosomal integration vector for the purpose of inducing homologous recombination with a chromosomal sequence. The re-NSI is modified with respect to chr-NSI by the addition, deletion, or substitution of at least one nucleotide. Sufficient homology must exist, however, between the two nucleotide sequences of interest to enable homologous recombination to occur. For the purposes herein, re-NSI will enable production of a transformed *Methylomonas* sp. 16a having a deletion in at least one of the crtN1, ald, crtN2, or crtN3 genes, or a deletion of the promoter driving the endogenous crt gene cluster.

The term "genetic marker" or "selectable marker" means a phenotypic trait that can be visualized under special conditions. For example, an antibiotic resistance marker serves as a useful selectable marker, since it enables detection of cells which are resistant to the antibiotic, when cells are grown on media containing that particular antibiotic.

The term "markerless mutants" or "markerless transformants" refers to an allelic exchange mutant, wherein the mutant allele does not carry a genetic marker.

The term "SacB" means a *Bacillus* encoded protein that catalyzes the conversion of sucrose into levan, a product that is toxic to most Gram-negative microorganisms. The term "sacB" means a gene that encodes the "SacB" protein.

A "nucleic acid" is a polymeric compound comprised of covalently linked subunits called nucleotides. Nucleic acids include polyribonucleic acid (RNA) and polydeoxyribonucleic acid (DNA), both of which may be single-stranded or double-stranded. DNA includes cDNA, genomic DNA, synthetic DNA, and semi-synthetic DNA.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor (1989), particularly Chapter 11 and Table 11.1 therein (entirely incorporated herein by reference).

The term "oligonucleotide" refers to a nucleic acid, generally of about at least 18 nucleotides, that is hybridizable to a genomic DNA molecule, a cDNA molecule, or an mRNA molecule.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing "Gene" refers to a nucleic acid fragment that expresses a specific protein. It may or may not include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "homolog", as applied to a gene, means any gene derived from the same or a different microbe having the same function. A homologous gene may have significant sequence similarity.

"Coding sequence" or "coding region of interest" refers to a DNA sequence that codes for a specific amino acid sequence.

The term "codon optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes. Within the context of the present invention genes and DNA coding regions are codon optimized for optimal expression in *Methylomonas* sp. 16a.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include sequences encoding regulatory signals capable of affecting mRNA processing or gene expression.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

"Transformation" refers to the transfer of a nucleic acid fragment into the genome of a host organism, resulting in genetically stable inheritance. In the present invention, the host cell's genome is comprised of chromosomal and extra-chromosomal (e.g. plasmid) genes. Host organisms containing the transformed nucleic acid fragments are referred to as "transgenic" or "recombinant" or "transformed" organisms.

"Conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements (in addition to the foreign gene) that facilitate transformation of a particular host cell. "Expression cassette" refers to a specific vector containing a foreign gene and having elements in addition to the foreign gene that allow for enhanced expression of that gene in a foreign host.

The term "altered biological activity" refers to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

As used herein, the term "down-regulated" refers to a gene that has been mutated and/or disrupted such that the expression of the gene is less than that associated with the native sequence. In another embodiment, down-regulated includes elimination of the gene's expression (i.e. gene knockout). As used herein, the symbol "Δ" will be used to denote a mutation in the specified coding sequence and/or promoter wherein at least a portion (up to and including all) of said coding sequence and/or promoter has been disrupted by a deletion. In another embodiment, the disruption can occur by optionally inserting a nucleic acid molecule into the native sequence whereby the expression of one or more genes is down-regulated (either partially or completely).

The term "MWM1000 (Δald/crtN1)" refers to a mutant of Methylomonas sp. 16a in which the ald and crtN1 genes have been disrupted.

The term "MWM1100 (Δcrt cluster promoter)" refers to a mutant of Methylomonas sp. 16a in which the crt gene cluster promoter has been disrupted.

The term "MWM1200 (Δcrt cluster promoter +ΔcrtN3)" refers to a mutant of Methylomonas sp. 16a in which the crt gene cluster promoter and the crtN3 gene have been disrupted.

The term "MWM1300 (Δald/crtN1+ΔcrtN3)" refers to a mutant of Methylomonas sp. 16a in which the ald, crtN1 and the crtN3 genes have been disrupted.

The term "MWM1400 (ΔcrtN1)" refers to a mutant of Methylomonas sp. 16a in which the crtN1 gene has been disrupted.

The term "MWM1600 (Δcrt cluster)" refers to a mutant of Methylomonas sp. 16a in which the crt gene cluster comprising the ald, crtN1, and crtN2 genes has been disrupted.

The term "MWM1800 (ΔcrtN1+ΔcrtN3)" refers to a mutant of Methylomonas sp. 16a in which the crtN1 and crtN3 genes have been disrupted.

The term "MWM1900 (Δcrt cluster+ΔcrtN3)" refers to a mutant of Methylomonas sp. 16a in which the ald, crtN1, crtN2, and crtN3 genes have been disrupted.

The term "MPM1000 (ΔcrtN3)" refers to a mutant of Methylomonas sp. 16a in which the crtN3 gene has been disrupted.

The term "MPM1200 (ΔcrtN2)" refers to a mutant of Methylomonas sp. 16a in which the crtN2 gene has been disrupted.

The term "MPM1300 (Δald)" refers to a mutant of Methylomonas sp. 16a in which the ald gene has been disrupted.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.); BLASTP, BLASTN, BLASTX (Altschul et al., *J. Mol. Biol.* 215:403-410 (1990)); DNASTAR (DNASTAR, Inc., Madison, Wis.); and the FASTA program incorporating the Smith-Waterman algorithm (W. R. Pearson, *Comput. Methods Genome Res.*, [Proc. Int. Symp.], Meeting Date 1992, 111-20. Suhai, Sandor, Ed.; Plenum: New York, N.Y. (1994)). Within the context of this application it will be understood that where sequence analysis software is used for analysis, the results of the analysis are based on the "default values" of the program referenced, unless otherwise specified. As used herein "default values" will mean any set of values or parameters (set by the software manufacturer) which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular*

*Biology*, published by Greene Publishing Assoc. and Wiley-Interscience, Hoboken, N.J. (1987).

*Methylomonas* sp. 16a

Of particular interest in the present invention are high growth obligate methanotrophs having an energetically favorable carbon flux pathway. For example, a specific strain of methanotroph has been discovered having several pathway features that makes it particularly useful for carbon flux manipulation. This strain is known as *Methylomonas* 16a (ATCC PTA 2402) (U.S. Pat. No. 6,689,601; hereby incorporated by reference); and, this particular strain and other related methylotrophs are preferred microbial hosts for expression of numerous gene products. This strain may be identified by the characteristic 16S rRNA sequence as set forth in SEQ ID NO:1.

The present strain contains several anomalies in the carbon utilization pathway. For example, based on genome sequence data, the strain is shown to contain genes for two pathways of hexose metabolism. The Entner-Douderoff Pathway (which utilizes the keto-deoxy phosphogluconate aldolase enzyme) is present in the strain. It is generally well accepted that this is the operative pathway in obligate methanotrophs. Also present, however, is the Embden-Meyerhof Pathway (which utilizes the fructose bisphosphate aldolase enzyme). It is well known that this pathway is either not present, or not operative, in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Additional methanotrophic bacteria having this characteristic were subsequently discovered including, for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate-dependent instead of ATP-dependent. This feature adds to the energy yield of the pathway by using pyrophosphate instead of ATP. Because of its significance in providing an energetic advantage to the strain, this gene in the carbon flux pathway is considered diagnostic for the present strain.

In methanotrophic bacteria, methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those 3-carbon molecules is recycled back through the RuMP pathway and the other 3-carbon fragment is utilized for cell growth. In methanotrophs and methylotrophs the RuMP pathway may occur as one of three variants. However, only two of these variants are commonly found: the FBP/TA (fructose bisphosphotase/transaldolase) pathway or the KDPG/TA (keto deoxy phosphogluconate/transaldolase) pathway (Dijkhuizen L., G. E. Devries. "The Physiology and biochemistry of aerobic methanol-utilizing gram negative and gram positive bacteria". In: *Methane and Methanol Utilizers*; Colin Murrell and Howard Dalton, Eds.; Plenum: N.Y., 1992).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected, whereas the former is not. The finding of the FBP genes in an obligate methane-utilizing bacterium is both surprising and suggestive of utility. The FBP pathway is energetically favorable to the host microorganism due to the fact that more energy (ATP) is utilized than is utilized in the KDPG pathway. Thus, organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane-utilizing organisms as production platforms for either single cell protein or for any other product derived from the flow of carbon through the RuMP pathway (e.g., carotenoids).

Thus, it is expected that high growth, energetically favorable *Methylomonas* strain which:

(a) grows on a C1 carbon substrate selected from the group consisting methane and/or methanol; and (b) comprises a functional Embden-Meyerhof carbon pathway, said pathway comprising a gene encoding a pyrophosphate-dependent phosphofructokinase enzyme;

will be a particularly preferred microbial host organism that is well suited for the production of various commercial products of interest, following appropriate genetic engineering.

The Native $C_{30}$ Carotenoid Pathway of *Methylomonas* sp. 16a

*Methylomonas* sp. 16a naturally produces a $C_{30}$ carotenoid in very high concentrations within the cell, which is responsible for the organism's natural pink pigment upon visual inspection of the bacterial cells. Production of this pigment is indicative of naturally high carbon flow through the isoprenoid pathway. Isoprenoids are an extremely large and diverse group of natural products found in all living organisms that have a common biosynthetic origin, based on a single metabolic precursor known as isopentenyl diphosphate (IPP). The group of natural products known as isoprenoids includes all substances that are derived biosynthetically from the 5-carbon compound isopentenyl diphosphate, and includes steroids, carotenoids, and squalene.

Genes Involved in Carotenoid Production

The enzyme pathway involved in the biosynthesis of carotenoid compounds can be conveniently viewed in two parts, the upper isoprenoid pathway (providing for the conversion of pyruvate and glyceraldehyde-3-phosphate to farnesyl pyrophosphate) and the lower carotenoid biosynthetic pathway (which provides for the synthesis of either diapophytoene ($C_{30}$) or phytoene ($C_{40}$) and all subsequently produced carotenoids) (see FIG. 1).

The upper isoprenoid biosynthetic pathway leads to the production of a $C_5$ isoprene subunit, isopentenyl pyrophosphate (IPP); however, this biosynthetic process may occur through either of two pathways. First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135-140(1993); Rohmer et al, *Biochem.*, 295: 517-524 (1993); Schwender et al., *Biochem.*, 316: 73-80 (1996); and Eisenreich et al., *Proc. Natl. Acad. Sci. USA*, 93: 6431-6436 (1996)). This mevalonate-independent pathway (shown in FIG. 1) is characterized by, but not limited to, the enzymes encoded by the following genes: the "dxs" gene (encoding 1-deoxyxylulose-5-phosphate synthase); the "dxr" gene (encoding 1-deoxyxylulose-5-phosphate reductoisomerase; also known as ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "IytB" gene (also known as ispH)involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase). The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The division between the upper isoprenoid pathway and the lower carotenoid pathway is somewhat subjective. Because FPP synthesis is common in both carotenogenic and non-carotenogenic bacteria, Applicants consider the first step in the lower carotenoid biosynthetic pathway to begin with the conversion of farnesyl pyrophosphate (FPP) to compounds of two divergent pathways, which lead to the formation of either $C_{30}$ diapocarotenoids or $C_{40}$ carotenoids.

For the biosynthesis of $C_{40}$ carotenoids, a series of enzymatic reactions catalyzed by CrtE and CrtB occur to convert FPP to geranylgeranyl pyrophosphate (GGPP) to phytoene, the first 40-carbon molecule of the lower carotenoid biosynthesis pathway. From the compound phytoene, a spectrum of $C_{40}$ carotenoids are produced by subsequent hydrogenation, dehydrogenation, cyclization, oxidation, or any combination of these processes. For example, lycopene, which imparts a "red"-colored spectra, is produced from phytoene through four sequential dehydrogenation reactions by the removal of eight atoms of hydrogen, catalyzed by phytoene desaturase (encoded by the gene crtI). Lycopene cyclase (encoded by the gene crtY) converts lycopene to β-carotene. β-carotene is converted to zeaxanthin via a hydroxylation reaction resulting from the activity of β-carotene hydroxylase (encoded by the crtZ gene). These examples are not limiting and many other carotenoid genes and products (e.g., crtX, crtW/O) exist within this $C_{40}$ lower carotenoid biosynthetic pathway. For example, β-carotene can be converted to canthaxanthin by β-carotene ketolases encoded by crtW, bkt or crtO genes, canthaxanthin can be converted to astaxanthin by β-carotene hydroxylase encoded by the crtZ gene, and zeaxanthin can be converted to astaxanthin by β-carotene ketolases encoded by crtW, bkt, or crtO genes.

Within the $C_{30}$ pathway, the first unique step in the biosynthetic pathway begins with the conversion of FPP to diapophytoene. However, details concerning the conversion of FPP to diapophytoene and subsequent reactions to produce various $C_{30}$ carotenoids are not particularly well-understood or generalized.

In *Staphylococcus aureus*, it has been determined that the first committed reaction toward $C_{30}$ carotenoid biosynthesis is the head-to-head condensation of two molecules of FPP by CrtM, forming dehydrosqualene (Wieland, B. et al., *J. Bacteriol.*, 176(24): 7719-7726 (1994)). Subsequently, dehydrosqualene desaturase (encoded by crtN) is successively dehydrogenated in three steps to produce 4,4'-diaponeurosporene (Wieland et al., supra). However, at present time public databases include only one single gene (GenBank® Accession Number X73889) and 4 genomic sequences (NC002745, NC002758, AP003137, AP003365) of crtN and crtM, isolated from *S. aureus* strains N315 and Mu50. A single report exists concerning the heterologous overexpression of crtN from *S. aureus* in *E. coli* (Raisig, A., and G. Sandmann., *J. Bacteriol.*, 181(19):6184-6187 (1999)). Based on identification of carotenoid compounds, it is known that the next stages in the $C_{30}$ metabolic pathway for *S. aureus* involve introduction of oxygen functions on the terminal methyl group to produce aldehyde and carboxylic acid forms of the carotenoid (Marshall, J. H., and G. J. Wilmoth., *J. Bacteriol.*, 147: 900-913 (1981) and 147: 914-919 (1981)); however, the genes responsible for this functionality have not been clearly identified.

In *Methylomonas* 16a, two operons have been identified within the genomic sequence containing carotenoid biosynthetic genes. The first biosynthetic operon (referred to herein as the "crt gene cluster"), encodes three genes, each of which is described below:

The first gene (designated crtN1; SEQ ID NO:2) encodes a putative diapophytoene dehydrogenase with the highest BLAST hit to a diapophytoene dehydrogenase from *Heliobacillus mobilis* (34% identity and 58% similarity);

The middle gene (designated ald; SEQ ID NO:3) encodes a putative aldehyde dehydrogenase with the highest BLAST hit to a betaine aldehyde dehydrogenase from *Arabidopsis thaliana* (33% identity and 50% similarity); and The third gene (designated crtN2; SEQ ID NO:4) also encodes a putative diapophytoene dehydrogenase with the highest BLAST hit to a hypothetical protein of phytoene dehydrogenase family from *Staphylococcus aureus* (51% identity and 67% similarity).

Figure 3:
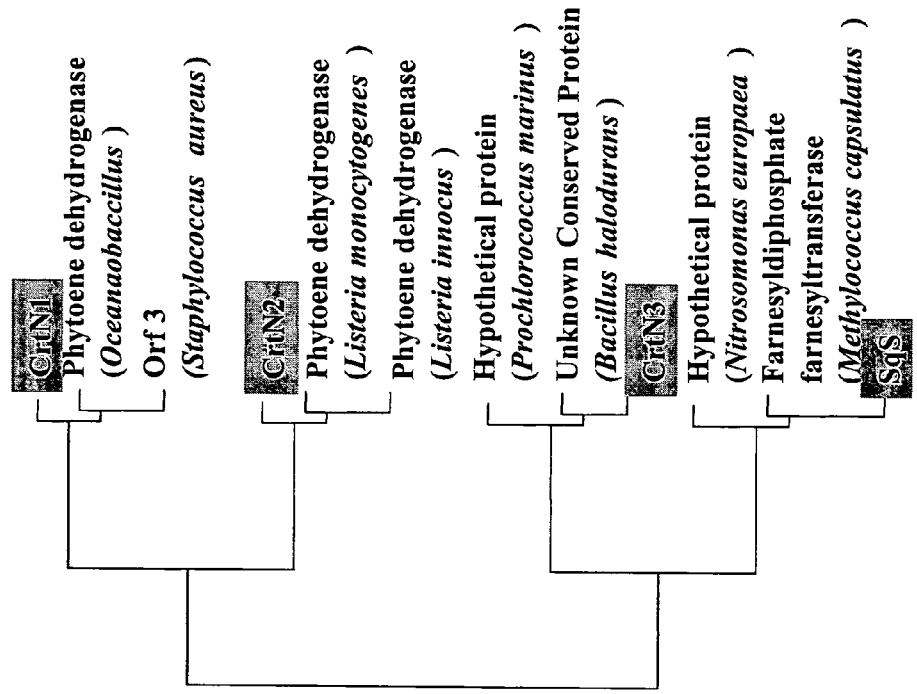
FIG. 3 shows results of a Clustal W analysis of the *Methylomonas* sp. 16a carotenoid genes crtN1, crtN2, crtN3, and sqs.

The second biosynthetic operon encodes a fourth gene designated as crtN3 (SEQ ID NO:5; FIG. 2). "Clustal W" analysis conducted using the sequences for crtN1, crtN2, crtN3 and sqs revealed that crtN3 is not closely linked to crtN1 and crtN2 (FIG. 3). "Clustal W" is a multiple sequence alignment program for DNA or proteins that produces biologically meaningful multiple sequence alignments of divergent sequences. This program calculates the best match for a selected sequence, and lines them up so that the identities, similarities and differences can be visualized (D. Higgins et. al., *Nucleic Acid Res.*, 22:4673-4680 (1994)). When the crtN3 (which contains sequences that are homologous to domains of other FAD-dependent oxidoreductases) was viewed in context of its surrounding ORFs, it was observed that crtN3 is located at the end of a cluster of ORFs that have high homology to proteins that play a role in fatty acid metabolism (FIG. 2). The crtN3 gene encodes a hypothetical protein with the highest BLAST hit to an unknown conserved protein family from *Bacillus halodurans* (31% identity and 48% similarity).

The interaction between these proteins of the carotenoid biosynthetic pathway in *Methylomonas* sp. 16a is not well understood at this time.

Creation of Allelic Exchange Mutants via Homologous Recombination and Positive Selection The ability to produce specific defined mutations in a microorganism frequently relies on exploitation of the native homologous recombination properties of the cell to replace a nucleotide sequence of interest with a modified copy. Most frequently, the nucleotide sequence of interest is a particular functional gene of interest, which is then disrupted by the insertion of an antibiotic-resistance marker. In theory, this type of recombination event is easily detected on a selective medium; however, performing allelic exchange in C1 metabolizing microorganisms has been relatively cumbersome due to the organisms' slow growth rates and the rarity of double-crossover events (which require extensive screening to isolate an allelic-exchange mutant). Despite these difficulties, a novel positive selection method for the identification of allelic exchange mutants obtained by targeted homologous recombination has been developed, as described in co-pending U.S. patent application Ser. No. 60/527,877, which is incorporated herein by reference.

Briefly, the positive selection (or direct genetic selection) of mutant bacteria is possible whenever survival of the recombinant bacteria depends upon the presence or absence of a particular function encoded by the DNA that is introduced into the organism. The advantage of a selection method over a screening method is that growth of bacteria with the specific desired mutation is greatly favored over bacteria lacking that specific mutation, thus facilitating the identification of the preferred mutants.

Direct or positive selection vectors containing genes that convey lethality to the host are well known. For example, expression of the *Bacillus subtilis* or the *B. amyloliquefaciens* sacB genes in the presence of sucrose is lethal to *E. coli* and a variety of other Gram-negative and Gram-positive bacteria. The sacB gene encodes levansucrase, which catalyzes both the hydrolysis of sucrose and the polymerization of sucrose to form the lethal product levan. Although the basis for the lethality of levansucrase in the presence of sucrose is not fully understood, the inability of *E. coli* and many other gram negative bacteria to grow when sacB is expressed can be exploited to directly select for cells that have lost the sacB gene via homologous recombination. Numerous methods have been developed for the selection of various bacterial mutants, based on sacB. See for example: U.S. Pat. No. 6,048,694 (Bramucci et al.) concerning *Bacillus*; U.S. Pat. No. 5,843,664 (Pelicic et al.) concerning mycobacterium; U.S. Pat. No. 5,380,657 (Schaefer et al.) concerning *Coryneform* bacteria; Hoang et al. (*Gene*, 212 (1):77-86 (1998)) concerning *Pseudomonas aeruginosa*; Copass et al. (*Infection and Immun.*, 65(5):1949-1952 (1997)) concerning *Helicobacter pylori*; and Kamoun et al. (*Mol. Microbiol.*, 6(6):809-816 (1992)) concerning *Xanthomonas*.

Figure 5:
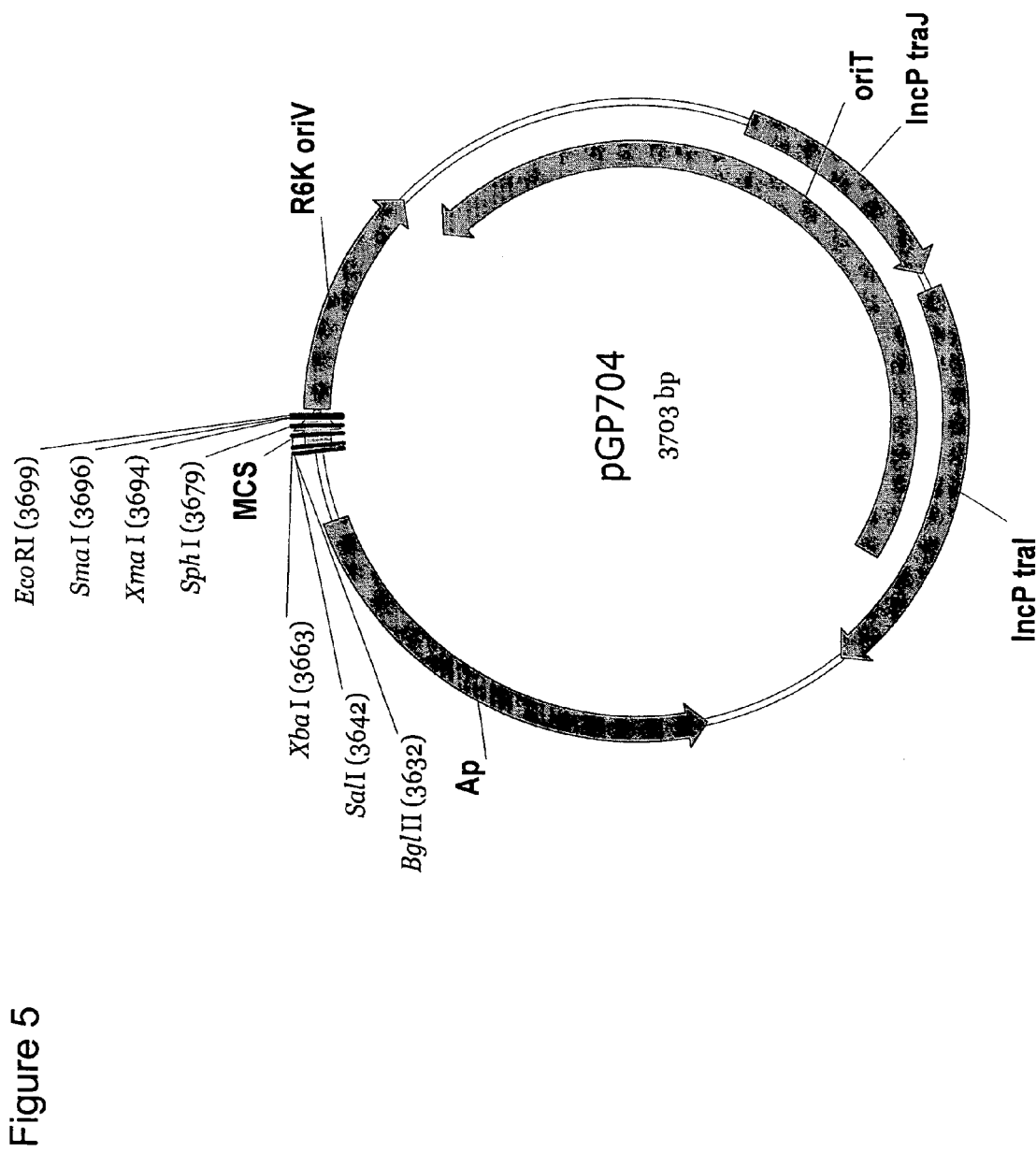
FIG. 5 is a plasmid map of pGP704.

The principle of the two-step positive selection strategy based on use of sacB for C1 metabolizing bacteria is illustrated in FIG. 4. This method relies on the application of a positive selection vector, in a preferred embodiment derived from the suicide delivery vector pGP704, which is able to integrate into the chromosome of C1 metabolizing bacteria to produce mutations that are the result of both single- or double-crossover events (FIG. 5). Specifically, the positive selection vector comprises:

(i) at least one gene encoding resistance to a first selectable marker (e.g., Amp);

(ii) a sacB coding region encoding a levansucrase enzyme under the control of a suitable promoter; and (iii) a replacement nucleotide sequence of interest (i.e., re-NSI), which one desires to insert into the chromosome of the C1 metabolizing bacteria as a replacement to an existing nucleotide sequence of interest in the bacterial chromosome (i.e., chr-NSI). Thus, re-NSI is modified with respect to chr-NSI by the addition, substitution, or deletion of at least one nucleotide.

Upon transformation of C1 metabolizing bacteria with the positive selection vector described above, a single-crossover event by homologous recombination occurs between chr-NSI and re-NSI, such that the entire positive selection vector is integrated into the bacterial chromosome at the site of crossover. These events can be selected by growth on the first selectable marker (e.g., Amp), whereby a complete copy of chr-NSI and a complete copy of re-NSI are present in the chromosome. Upon removal of selection by the first selectable marker, a second crossover event may occur, resulting in the "looping out" of the positive selection vector, to yield transformants containing either the chr-NSI or the re-NSI in the chromosome (FIG. 4). Direct selection of these allelic exchange transformants is possible by growing the transformants in the presence of sucrose, since single-crossover mutants will be killed under these conditions.

Screening Methods

Methods of screening in microbiology are discussed at length in Brock, supra. In the present invention, a two-step selection process permits the identification of double-crossover mutations in C1 metabolizing bacterial cells by applying positive selection pressure. Using this strategy, the positive selection vector should comprise a first selectable marker and a sacB marker. Selection involves first growing the transformants on media containing the first selectable marker, to identify those cells that have undergone a single-crossover (i.e., wherein the entire chromosomal integration vector has integrated into the host cell's genome). Then, the selection pressure is removed and a second crossover event may occur. Selection for allelic exchange mutants requires growth of the cells on sucrose, since SacB expression will be lethal to all single-crossover mutants. Differentiation between allelic exchange mutants containing the wildtype and mutant allele is then possible using standard molecular techniques (e.g., PCR), well known to one of skill in the art. One preferred advantage of the two-step selection strategy described above is that allelic exchange transformants that are produced are markerless (i.e., lacking any antibiotic or other genetic marker indicative of the allelic exchange).

Host Strain Optimization via Allelic Exchange within the $C_{30}$ Carotenoid Biosynthetic Pathway Four non-pigmented *Methylomonas* sp. 16a bacterial host organisms, each lacking any antibiotic markers, are provided in the instant invention. These optimized host strains comprise a deletion in the ald/crtN1 genes, a deletion of the crt gene cluster promoter, a deletion in the ald/crtN1 genes and the crtN3 gene, and a deletion in the crt gene cluster promoter and the crtN3 gene. Three other strains may convey additional advantages for a *Methylomonas* production host organism having knockouts in one or more of the crtN1, crtN2, and crtN3 genes. Each of these bacterial strains was created by investigation of allelic exchange mutations within the native crt gene cluster (comprising the crtN1, ald, and crtN2 genes) and the crtN3 gene of *Methylomonas* sp. 16a.

The process by which these allelic exchange mutants were created is shown in FIG. 4, and requires a re-NSI that is modified with respect to chr-NSI by the addition, substitution, or deletion of at least one nucleotide. For the purposes herein, the chr-NSI encodes at least one of the native crtN1, ald, crtN2, and crtN3 genes of *Methylomonas* sp. 16a; alternatively, the chr-NSI corresponds to the promoter driving the *Methylomonas* sp. 16a crt gene cluster. The re-NSI will enable production of a transformed *Methylomonas* sp. 16a having a deletion at least one of the crtN1, ald, crtN2, and crtN3 genes, or a deletion of the promoter driving the crt gene cluster. As will be obvious to one of skill in the art, the advantage of the two-step selection methodology described herein is that the double-crossover mutant thus generated is "markerless"; enabling subsequent mutations using the same technique (i.e., since there is no need for a different selectable marker corresponding to each mutation created).

One factor to consider regardless of the specific type of re-NSI generated is the overall homology between the re-NSI and the chr-NSI. In general, it is well known in the art that homologous recombination requires a minimum of 50 nucleotides of homology on each side of the site of a crossover. When preparing a re-NSI for use in the selection processes described herein, it is preferable to have regions homologous to the chr-NSI flanking (both 5' and 3') the site of the addition, substitution, or deletion. More preferably, a 1 kB region of homology is preferred on both sides of the addition, substitution, or deletion. In contrast, re-NSI is not expected to be limited in length, beyond the limitations inherent to homologous recombination.

Generation of a re-NSI containing an addition, substitution, or deletion of at least one nucleotide with respect to the chr-NSI can be accomplished using numerous techniques known to a skilled artisan in the field of molecular biology. Although not intended to be limiting, deletions and additions may be generated by the use of restriction endonucleases, in vitro transposition reactions, or PCR methodologies; all techniques well known to one of skill in the art.

A preferred method for generation of re-NSI is via PCR methodologies, as utilized herein. Alternatively, substitutions may be generated by mutagenesis of the re-NSI. Two suitable approaches include error-prone PCR (Leung et al., *Technique*, 1:11-15 (1989); Zhou et al., *Nucleic Acids Res.*, 19:6052-6052 (1991); and Spee et al., *Nucleic Acids Res.*, 21:777-778 (1993)) and in vivo mutagenesis. The principal advantage of error-prone PCR is that all mutations introduced by this method will be within the re-NSI, and any change may be easily controlled by changing the PCR conditions. Alternatively, in vivo mutagenesis may be employed using commercially available materials such as *E. coli* XL1-Red strain, and the *Epicurian coli* XL1-Red mutator strain from Stratagene (La Jolla, Calif.; Greener and Callahan, *Strategies*, 7:32-34 (1994)). This strain is deficient in three of the primary DNA repair pathways (mutS, mutD, and mutT), resulting in a mutation rate 5000-fold higher than that of wild-type. In vivo mutagenesis does not depend on ligation efficiency (as with error-prone PCR); however, a mutation may occur at any region of the vector and the mutation rates are generally much lower.

It is also contemplated that it may be desirable to replace a wild-type gene of interest (i.e., chr-NSI) in the C1 metabolizing bacteria with a mutant gene (i.e., re-NSI) that has been constructed using the method of "gene shuffling" (U.S. Pat. Nos. 5,605,793; 5,811,238; 5,830,721; and 5,837,458). The method of gene shuffling is particularly attractive due to its facile implementation, and high rate of mutagenesis. The process of gene shuffling involves the restriction of a gene of interest into fragments of specific size in the presence of additional populations of DNA regions of both similarity to, or difference to, the gene of interest. This pool of fragments is then denatured and reannealed to create a mutated gene. The mutated gene is subsequently screened for altered activity.

One factor to consider during the preparation of a re-NSI for use in the two-step selection strategy concerns the placement of the addition, deletion, or substitution within the sequence of interest. Specifically, the re-NSI is first inserted into the chromosome by integration of the chromosomal integration vector (a single-crossover event). The second crossover event that occurs can result in either a mutant or wildtype sequence in the chromosome, since the single-crossover contains two copies of the nucleotide sequence of interest. In order to increase the percentage of segregants that retain the re-NSI, as opposed to reverting to the wildtype encoded by the chr-NSI, it is desirable to "center" the mutation with respect to the flanking DNA that has homology to the chr-NSI. For example, if a point mutation was perfectly centered within a re-NSI, about 50% of the segregants would be expected to retain the mutation in the chromosome (thus producing a 1:1 ratio of double-crossover mutants to wild-type cells.

Transformation of C1 Metabolizing Bacteria

Techniques for the transformation of C1 metabolizing bacteria are not well developed, although general methodology that is utilized for other bacteria, which is well known to those of skill in the art, may be applied.

Electroporation has been used successfully for the transformation of: *Methylobacterium extorquens* AM1 (Toyama, H., et al., *FEMS Microbiol Left.*, 166:1-7 (1998)), *Methylophilus methylotrophus* AS1 (Kim, C. S., and T. K. Wood, *Appl. Microbiol. Biotechnol.*, 48:105-108 (1997)), and *Methylobacillus* sp. strain 12S (Yoshida, T., et al., *Biotechnol. Lett.*, 23: 787-791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in onT; 2.) A single-strand DNA is released to the recipient through a pore or pilus structure; 3.) A DNA relaxase enzyme cleaves the double-strand DNA at onT and binds to a released 5' end (forming a relaxosome as the intermediate structure); and 4.) Subsequently, a complex of auxiliary proteins assemble at onT to facilitate the process of DNA transfer.

2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an onT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (*Mikrobiologiya*, 64(5): 686-691 (1995)); Motoyama, H. et al. (*Appl. Micro. Biotech.*, 42(1): 67-72 (1994)); Lloyd, J. S. et al. (*Archives of Microbiology*, 171(6): 364-370 (1999)); and Odom, J. M. et al. (U.S. Ser. No. 09/941,947 corresponding to WO 02/18617).

Applications for the Optimized Hosts Provided Herein

As is well known to those of skill in the art, efforts to genetically engineer a microorganism for high-level production of a specific product frequently require substantial manipulation to the native host machinery and biosynthetic pathways. Historically, metabolic engineering of methanotrophs has remained relatively undeveloped due to the general lack of efficient genetic engineering tools, as compared to other industrial bacteria such as *E. coli* and the yeasts. Most methanotrophic molecular biology has focused on the engineering of the methane monooxygenase, such that it is directed toward more useful co-metabolic products (and wherein methane is not directly incorporated into the product molecule). In contrast, pathway engineering for net synthesis of carbon-containing compounds from methane requires both: 1.) the ability to inactivate genes already present in the methanotroph; and 2.) the ability to introduce foreign genes into the organism, to create new metabolic capabilities. In this way, new metabolic networks can be constructed to produce products that could not be made by the genetic engineering of methane monooxygenase alone.

The present invention represents tremendous progress in the genetic engineering of methanotrophic bacteria. Specifically, the *Methylomonas* sp. 16a optimized hosts provided herein comprise deletions in one or more of the crtN1, ald, crtN2, and crtN3 genes and the crt gene cluster promoter will be useful host organisms for the production of a variety of commercial products. In another embodiment, the optimized host provided herein comprise deletions selected from the group consisting of Δald(crtN1), ΔcrtN1, Δ crt cluster promoter, and Δ crt gene cluster (Δald+_ΔcrtN1+ΔcrtN2). In a further embodiment, the optimized hosts provided herein comprise deletions selected from the group consisting of Δald(crtN1)+ΔcrtN3, ΔcrtN1+ΔcrtN3, Δ crt cluster promoter+ΔcrtN3, and Δcrt gene cluster+ΔcrtN3. Specifically, advantages in the host organism are incurred by knocking out the native carotenoid pathway of the organism that lead to the production of pink-pigmented $C_{30}$ carotenoids, increasing the available carbon flux directed toward the products of interest. For example, products include, but are not limited to $C_{40}$ carotenoids, such as antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin. Additionally, these "markerless" mutants may offer significant advantages during industrial development of a C1 metabolizing host bacterium where the presence of antibiotic resistance genes would be undesirable, in terms of required regulatory approvals.

Recombinant Expression in the Optimized Hosts

Methods for introducing genes into a suitable microbial host, such as the optimized *Methylomonas* sp. 16a hosts described herein, are common. As will be obvious to one skilled in the art, the particular functionalities required to be introduced into a host organism for production of a particular product will depend on the host cell, the availability of substrate, and the desired end product(s).

The preferred genes to introduce into the optimized *Methylomonas* sp. 16a hosts of the present invention are various combinations of crt genes to produce $C_{40}$ carotenoids. Examples of suitable crt genes for use in the present invention include, but are not limited to crtE, crtB, crtI, crtY, crtZ and crt>genes isolated from *Pectobacterium cypripedii*, as described by Cheng et al. in copending U.S. Ser. No. 10/804,677, incorporated herein by reference; crtE, crtB, crtI, crtY, crtZ and crtX genes isolated from a member of the Enterobacteriaceae family, as described by Cheng et al. in copending U.S. Ser. No. 10/808,979, incorporated herein by reference; crtE, idi, crtB, crtI, crtY, crtZ genes isolated from *Pantoea agglomerans*, as described by Cheng et al. in copending U.S. Ser. No. 10/808,807, incorporated herein by reference; and crtE, idi, crtB, crtI, crtY, crtZ and crtX genes isolated from *Pantoea stewartii*, as described by Cheng et al. in copending U.S. Ser. No. 10/810,733, incorporated herein by reference. More preferably, the crtE-idi-crtY-crtI-crtB gene cluster, given as SEQ ID NO:6, derived from the crtE-idi-crtY-crtI-crtB-crtZ gene cluster (SEQ ID NO:41) isolated from *Pantoea agglomerans*, described by Cheng et al. in copending U.S. Ser. No. 10/808,807, is used.

For the purposes of the present invention, it was desirable to modify a portion of the codons encoding polypeptides having ketolase or hydroxylase activity, respectively, to enhance the expression of genes encoding those polypeptides in *Methylomonas* sp. 16a and derivatives thereof. Thus, the nucleic acid sequence of the native genes, e.g., the β-carotene ketolase (crtW) and the β-carotene hydroxylase (crtZ) genes from *Agrobacterium aurantiacum*, were modified to employ host preferred codons, as described in Example 8. In general, host preferred codons can be determined from the codons of highest frequency in the proteins (preferably expressed in the largest amount) in a particular host species of interest. Thus, the coding sequence for a polypeptide having ketolase or hydroxylase activity can be synthesized in whole or in part using the codons preferred in the host species. All (or portions) of the DNA also can be synthesized to remove any destabilizing sequences or regions of secondary structure which would be present in the transcribed mRNA. All (or portions) of the DNA also can be synthesized to alter the base composition to one more preferable in the desired host cell.

In one preferred embodiment, the crtE-idi-crtY-crtI-crtB gene cluster (SEQ ID NO:6) from *Pantoea agglomerans* is used in conjunction with the codon-optimized crtW (β-carotene ketolase) gene given as SEQ ID NO:7 to produce the $C_{40}$ carotenoid canthaxanthin.

In another preferred embodiment, the crtE-idi-crtY-crtI-crtB gene cluster is used in conjunction with the codon-optimized crtW gene and the codon-optimized crtZ (β-carotene hydroxylase) gene given as SEQ ID NO:8 to produce the $C_{40}$ carotenoid astaxanthin.

Microbial expression systems and expression vectors containing regulatory sequences that direct high level expression of foreign proteins are well known to those skilled in the art. Any of these could be used to construct chimeric genes for production of a variety of gene products. These chimeric genes could then be introduced into the optimized hosts of the present invention via transformation to provide high level expression of the required enzymes.

Vectors or cassettes useful for the transformation of the optimized hosts of the present invention are well known in the art. Typically the vector or cassette contains sequences directing transcription and translation of the relevant gene(s), a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the desired ORFs in the optimized host cells of the present invention are numerous and familiar to those skilled in the art. Virtually any promoter capable of driving the desired genes is suitable for the present invention including, but not limited to: CYC1, HIS3, GAL1, GAL10, ADH1, PGK, PHO5, GAPDH, ADC1, TRP1, URA3, LEU2, ENO, TPI, AOX1, lac, ara, tet, trp, $IP_L$, $IP_R$, T7, tac, trc, amy, apr, npr and various phage promoters. Additionally, the deoxy-xylulose phosphate synthase or methanol dehydrogenase operon promoter (Springer et al., *FEMS Microbiol Lett,* 160:119-124 (1998)), the promoter for polyhydroxyalkanoic acid synthesis (Foellner et al., *Appl. Microbiol. Biotechnol.,* 40:284-291 (1993)), promoters identified from native plasmids in methylotrophs (EP 296484), Plac (Toyama et al., *Microbiology,* 143:595-602 (1997); EP 62971), Ptrc (Brosius et al., *Gene,* 27:161-172 (1984)), and promoters associated with antibiotic resistance [e.g., kanamycin (Springer et al., *FEMS Microbiol Lett,* 160:119-124 (1998); Ueda et al., *Appl. Environ. Microbiol.,* 57:924-926 (1991)), tetracycline (U.S. Pat. No. 4,824,786) or chloramphenicol] are suitable for expression in the optimized *Methylomonas* sp. 16a host cells of the present invention.

It is necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell. Each of these types of modifications are encompassed in the present invention, as means to further optimize expression of preferred products within the optimized hosts of the present invention.

Finally, to promote accumulation of a preferred product, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

Industrial Production Methodologies

For commercial production of the desired product, e.g., $C_{40}$ carotenoids, a variety of culture methodologies may be applied. For example, large-scale production of a specific gene product overexpressed from the optimized *Methylomonas* sp. 16a bacterial host organisms of the present invention may be produced by batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur while adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, $2^{nd}$ ed. (1989) Sinauer Associates: Sunderland, Mass., or Deshpande, Mukund V., *Appl. Biochem. Biotechnol.*, 36:227 (1992).

Commercial production of the desired product, e.g., $C_{40}$ carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Fermentation media in the present invention must contain suitable carbon substrates. Suitable carbon substrates for the optimized *Methylomonas* sp. 16a host cells of the present invention include methane and methanol for which metabolic conversion into key biochemical intermediates has been demonstrated.

DESCRIPTION OF PREFERRED EMBODIMENTS

*Methylomonas* sp. 16a is a C1 metabolizing bacteria that is capable of efficiently using either methanol or methane as a carbon substrate. *Methylomonas* is also metabolically versatile in that it contains multiple pathways for the incorporation of carbon from formaldehyde into 3-carbon units, and is capable of genetic exchange with donor species such as *Escherichia coli* via bacterial conjugation. Despite these advantageous qualities, considerable optimization of the host organism for use as a microbial platform of choice for the production of a variety of materials was required. Specifically, it was desirable to reduce and/or eliminate the amount of carbon flow channeled toward the native $C_{30}$ carotenoids produced by the organism, such that this carbon would be available for more desirable products.

Following the recent development of a method for the generation and identification of defined mutations within the organism by homologous recombination, based on the positive selection vector pGP704::sacB, it was possible in the work described herein to methodically produce gene and promoter knockouts within the native $C_{30}$ carotenoid biosynthetic pathway. Specifically, five different allelic exchange mutations were investigated: ΔcrtN1, Δald/crtN1, ΔcrtN2, ΔcrtN3, Δcrt gene cluster (Δald, ΔcrtN1, and ΔcrtN2), and a deletion of the crt gene cluster promoter (thereby creating a ΔcrtN1, Δald, and ΔcrtN2 knockout). Additionally, several double mutants comprising a deletion in one or more of the $C_{30}$ carotenoid genes (i.e. ΔcrtN1, Δald(crtN1), Δcrt gene cluster promoter, and Δcrt gene cluster) in combination with a deletion of the crtN3 gene were also investigated. The results of this work produced four optimized host strains that were non-pigmented, since the wildtype $C_{30}$ carotenoid "pink" pigment was no longer produced in the organism.

It is expected that these optimized host strains will be useful for increased expression of a variety of heterologous proteins in *Methylomonas* sp. 16a. For example, there is a general practical utility for microbial production of $C_{40}$ carotenoid compounds. This practical utility results since these compounds are very difficult to make chemically (Nelis and Leenheer, *Appl. Bacteriol.*, 70:181-191 (1991)). Industrially, only a few carotenoids are used for food colors, animal feeds, pharmaceuticals, and cosmetics, despite the existence of more than 600 different carotenoids identified in nature. Most carotenoids have strong color and can be viewed as natural pigments or colorants. Furthermore, many carotenoids have potent antioxidant properties and thus inclusion of these compounds in the diet is thought to be healthful.

A variety of methods for carotenoid production based on microbial platforms have recently been described in the art [e.g., *E. coli* and *Candia utilis* for production of lycopene (Farmer W. R. and J. C. Liao., *Biotechnol. Prog.*, 17: 57-61 (2001); Wang C. et al., *Biotechnol. Prog.*, 16: 922-926 (2000); Misawa, N. and H. Shimada., *J. Biotechnol.*, 59:169-181 (1998); Shimada, H. et al., *Appl. Environ. Microbiol.*, 64:2676-2680 (1998)); *E. coli*, *Candia utilis* and *Pfaffia rhodozyma* for production of β-carotene (Albrecht, M. et al., *Biotechnol. Lett.*, 21: 791-795 (1999); Miura, Y. et al., *Appl. Environ. Microbiol.*, 64:1226-1229 (1998); U.S. Pat. No. 5,691,190; *E. coli* and *Candia utilis* for production of zeaxanthin (Albrecht, M. et al., supra; Miura, Y. et al., supra); *E. coli* and *Pfaffia rhodozyma* for production of astaxanthin (U.S. Pat. Nos. 5,466,599; 6,015,684; 5,182,208; 5,972,642); see also: U.S. Pat. Nos. 5,656,472, 5,545,816, 5,530,189, 5,530,188, 5,429,939, and 6,124,113]. However, these methods of producing carotenoids suffer from low yields and reliance on relatively expensive feedstocks. Thus, it would be desirable to identify a method that produces higher yields of carotenoids in a microbial host, such as *Methylomonas* sp. 16a (or a derivative thereof), from an inexpensive feedstock, such as methane and/or methanol.

Odom et al. have previously demonstrated that the C1 metabolizing bacterium *Methylomonas* sp. 16a can be engineered for production of various $C_{40}$ carotenoids (U.S. Ser. No. 09/941,947 corresponding to WO 02/218617), by the introduction of one or more of the lower $C_{40}$ carotenoid biosynthetic pathway genes (i.e., crtE, crtX, crtY, crtI, crtB, crtZ, crtW, crtO, crtA, crtC, crtD, crtF, and crtU). Despite the previous demonstration of β-carotene production in this unique microbial host, however, further advancement towards creation of a recombinant host suitable for high-level production of a specific $C_{40}$ carotenoid product will require significant metabolic engineering to the native host machinery and biosynthetic pathways. The present invention will be particularly useful for efforts targeted toward the genetic engineering of this unique C1 metabolizing bacteria, since it is expected that the absence of the native $C_{30}$ carotenoid production will provide substantial advantages for gene expression leading to $C_{40}$ carotenoids, such as antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin.

The present invention also provides a codon-optimized β-carotene ketolase gene (crtW) and a β-carotene hydroxylase gene (crtZ) which were used to demonstrate the production of canthaxanthin and astaxanthin in the *Methylomonas* sp. 16a deletion mutants.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); by T. J. Silhavy, M. L. Bennan, and L. W. Enquist, *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "sec" means second(s), "min" means minute(s), "hr" means hour(s), "d" means day(s), "μL" means microliter(s), "mL" means milliliter(s), "L" means liter(s), "μM" means micromolar, "mM" means millimolar, "M" means molar, "mmol" means millimole(s), "μmol" mean micromole(s), "nmol" means nanomole(s), "g" means gram(s), "μg" means microgram(s), "ng" means nanogram(s), "nm" means nanometers, "U" means unit(s), "ppm" means parts per million, "bp" means base pair(s), "rpm" means revolutions per minute, "kB" means kilobase(s), "g" means the gravitation constant, "~" means approximately, "$OD_{600}$" means the optical density measured at 600 nm, "$OD_{260}/OD_{280}$" means the ratio of the optical density measured at 260 nm to the optical density measured at 280 nm, and "mAU" means milliabsorbance units.

Molecular Biology Techniques:

Methods for agarose gel electrophoresis were performed as described in Maniatis (supra). Polymerase Chain Reactions (PCR) techniques were found in White, B., *PCR Protocols: Current Methods and Applications*, Humana: Totowa, N.J. (1993), Vol. 15.

Media and Culture Conditions:

General materials and methods suitable for the maintenance and growth of bacterial cultures are found in: *Experiments in Molecular Genetics* (Jeffrey H. Miller), Cold Spring Harbor Laboratory: Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds.), American Society for Microbiology: Washington, D.C., pp 210-213; or, Thomas D. Brock in *Biotechnology: A Textbook of Industrial Microbiology*, $2^{nd}$ ed. Sinauer Associates: Sunderland, Mass. (1989). All reagents and materials used for the growth and maintenance of bacterial cells were obtained from Aldrich Chemicals (Milwaukee, Wis.), BD Diagnostic Systems (Sparks, Md.), Invitrogen Corp. (Carlsbad, Calif.), or Sigma Chemical Company (St. Louis, Mo.), unless otherwise specified.

Example 1

Growth of *Methylomonas* sp. 16a

Example 1 summarizes the standard conditions used for growth of *Methylomonas* sp. 16a (ATCC# PTA-240), as described in U.S. Pat. No. 6,689,601; hereby incorporated by reference.

*Methylomonas* Strain and Culture Media

The growth conditions described below were used throughout the following experimental Examples for treatment of *Methylomonas* 16a, unless conditions were specifically described otherwise.

*Methylomonas* sp. 16a was typically grown in serum stoppered Wheaton bottles (Wheaton Scientific; Wheaton, Ill.) using a gas/liquid ratio of at least 8:1 (i.e., 20 mL of ammonium liquid "BTZ" growth medium in a Wheaton bottle of 160 mL total volume). The composition of the BTZ growth medium is given below. The standard gas phase for cultivation contained 25% methane in air, although methane concentrations can vary ranging from about 5-50% by volume of the culture headspace. These conditions comprise growth conditions and the cells are referred to as growing cells. In all cases, the cultures were grown at 30° C. with constant shaking in a rotary shaker (Lab-Line, Barnstead/Thermolyne; Dubuque, Iowa) unless otherwise specified.

BTZ Media for *Methylomonas* 16a

*Methylomonas* 16a typically grows in a defined medium composed of only minimal salts; no organic additions such as yeast extract or vitamins are required to achieve growth. This defined medium known as BTZ medium (also referred to herein as "ammonium liquid medium") consisted of various salts mixed with Solution 1, as indicated in Tables 1 and 2. Alternatively, the ammonium chloride was replaced with 10 mM sodium nitrate to give "BTZ (nitrate) medium", where specified. Solution 1 provides the composition for a 100-fold concentrated stock solution of trace minerals.

TABLE 1

Solution 1*

| | Molecular Weight | Conc. (mM) | g per L |
|---|---|---|---|
| Nitriloacetic acid | 191.10 | 66.90 | 12.80 |
| CuCl$_2$ × 2H$_2$O | 170.48 | 0.15 | 0.0254 |
| FeCl$_2$ × 4H$_2$O | 198.81 | 1.50 | 0.30 |
| MnCl$_2$ × 4H$_2$O | 197.91 | 0.50 | 0.10 |
| CoCl$_2$ × 6H$_2$O | 237.90 | 1.31 | 0.312 |
| ZnCl$_2$ | 136.29 | 0.73 | 0.10 |
| H$_3$BO$_3$ | 61.83 | 0.16 | 0.01 |
| Na$_2$MoO$_4$ × 2H$_2$O | 241.95 | 0.04 | 0.01 |
| NiCl$_2$ × 6H$_2$O | 237.70 | 0.77 | 0.184 |

*Mix the gram amounts designated above in 900 mL of H$_2$O, adjust to pH = 7.0, and add H$_2$O to a final volume of 1 L. Keep refrigerated.

TABLE 2

Ammonium Liquid Medium (BTZ)**

| | MW | Conc. (mM) | g per L |
|---|---|---|---|
| NH$_4$Cl | 53.49 | 10 | 0.537 |
| KH$_2$PO$_4$ | 136.09 | 3.67 | 0.5 |
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7.0) | 238.3 | | 50 mL |
| Solution 1 | | | 10 mL |

**Dissolve in 900 mL H$_2$O. Adjust to pH = 7.0, and add H$_2$O to give a final volume of 1 L. For agar plates: Add 15 g of agarose in 1 L of medium, autoclave, cool liquid solution to 50° C., mix, and pour plates.

Example 2

Construction of a Positive-Selection Suicide Vector for *Methylomonas* sp. Strain 16a The construction of chromosomal mutations within the *Methylomonas* genome required the use of suicide vectors. Thus, a modified version of the conditional replication vector pGP704 was created, comprising a npr-sacB cassette.

pGP704 as a Vector Backbone for the C1 Chromosomal Integration Vector

The plasmid pGP704 (Miller and Mekalanos, *J. Bacteriol.*, (170): 2575-2583 (1988); FIG. 5) was chosen as a suitable vector backbone for the C1 chromosomal integration vector, since it could be used as a vehicle to transfer replacement nucleotide sequences of interest into *Methylomonas* sp. 16a via conjugation. Plasmid pGP704 is a derivative of pBR322 that is Amp$^R$ but has a deletion of the pBR322 origin of replication (oriE1). Instead, the plasmid contains a cloned fragment containing the origin of replication of plasmid R6K. The R6K origin of replication (oriR6K) requires the Π protein, encoded by the pir gene. In *E. coli*, the Π protein can be supplied in trans by a prophage (λ pir) that carries a cloned copy of the pir gene. The pGP704 plasmid also contains a 1.9 kB BamHI fragment encoding the mob region of RP4. Thus, pGP704 can be mobilized into recipient strains by transfer functions provided by a derivative of RP4 integrated in the chromosome of *E. coli* strain SM10 or SY327. Once the plasmid is transferred, however, it is unable to replicate in recipients that lack the Π protein (e.g., recipients such as *Methylomonas* and other C1 metabolizing bacteria). This inability permits homologous recombination to occur between nucleotide sequences of interest on pGP704 and the intact chromosomal nucleotide sequences of interest.

Thus, on the basis of the above characteristics, the pGP704 vector backbone met the following conditions for a chromosomal integration vector suitable for C1 metabolizing bacteria: 1.) it was conditional for replication, thus allowing selection for integration into the chromosome; 2.) it possessed at least one selectable marker; 3.) it had an origin of transfer that was expected to be suitable for C1 metabolizing bacteria; 4.) it possessed mobilization genes; and 5.) it contained a variety of unique cloning sites. Other alternative chromosomal integration vectors having the characteristics listed above are expected to be suitable for use in the present invention, as described herein.

Plasmid pGP704 did not, however, permit easy detection and identification of clones that had undergone allelic exchange. Thus, pGP704 was modified to permit the positive selection of double-crossover events within *Methylomonas* and other C1 metabolizing bacteria.

Cloning of the npr-sacB Cassette

Plasmid pBE83 contained a *Bacillus amyloliquifaciens* sacB gene under the control of the neutral protease (npr) promoter (gift from V. Nagarajan, E.I. du Pont de Nemours and Co., Inc., Wilmington, Del.). The npr-sacB cassette was PCR amplified from pBE83 using DNA primers DrdI/npr-sacB and TthIII/npr-sacB. The DNA primers were constructed to include unique restriction sites at each terminus of the PCR product to facilitate subsequent cloning (as indicated by the underlined sequences below):

```
DrdI/npr-sacB:
5'-GACATCGATGTCGAATTCGAGCTCGGTACC  (SEQ ID NO: 9)
GATC-3'

TthIII/npr-sacB:
5'-GACCTCGTCGCTGTTATTAGTTGACTGTCA  (SEQ ID NO: 10)
GC-3'
```

The PCR reaction mixture was composed of the following: 10 μL of 10× PCR buffer; 16 μL (4 μL each) of dNTPs (320 mM stock); 1 μL of *Methylomonas* chromosomal DNA solution (~500 ng/μL); 8 μL of MgCl$_2$ solution (25 mM); 0.5 μL of Taq polymerase (5 U/μL); 1 μL of DrdI/npr-sacB primer (~36 nmol); 1 μL of TthIII/npr-sacB primer (~35 nmol); and 71 μL of sterile deionized water (NANOpure® Water System, Barnstead/Thermolyne). The PCR protocol was then performed on a 9600 GeneAmp® PCR System (Perkin Elmer), according to the thermocycling parameters below:

1 cycle: 94° C. (5 min);
1 cycle: 94° C. (5 min), 60° C. (2 min), 72° C. (3 min);
35 cycles: 94° C. (1 min), 60° C. (2 min), 72° C. (3 min);
1 cycle: 94° C. (1 min), 60° C. (2 min), 72° C. (10 min); and
Hold −4° C. (∞).

Afterward, the PCR product was ligated into the pCR2.1TOPO vector per the manufacturer's instructions (Invitrogen; Carlsbad, Calif.). The ligation mixture was transformed into TOP10 One Shot™ calcium chloride competent cells and transformants were screened as recommended by Invitrogen.

Plasmid DNA was isolated from positive clones (white colonies in a blue/white screen) using the QIAprep® Spin Mini-prep Kit (Qiagen; Valencia, Calif.) and the DNA was digested according to the manufacturer's instructions with restriction endonucleases DrdI and TthIII (New England Biolabs; Boston, Mass.). Initially, this PCR product was to be inserted into pGP704 digested with DrdI and TthIII; however, there were difficulties in cloning the DrdI/TthIII PCR product.

A modified cloning strategy was adopted, such that the PCR reaction described above was "repeated" using the Pfu DNA polymerase (Stratagene; LaJolla, Calif.). Specifically, the PCR reaction and protocol were performed exactly as described above, with the exception that Pfu polymerase and buffers from Stratagene were used. A PCR product having flush or blunt ends was produced. This PCR product was ligated directly into the XcaI site (GTA/ATC) of pGP704. The ligation mixture was transformed into calcium chloride competent *E. coli* SY327 cells (Miller V. L. and Mekalanos J. J. *Proc. Natl. Acad. Sci.* 81(11):3471-3475 (1984)).

The transformants were screened using the DrdI/npr-sacB and TthIII/npr-sacB PCR primers (SEQ ID NOs:9 and 10, respectively) to identify vectors containing the npr-sacB insert. The PCR products were analyzed on a 0.8% agarose gel. Plasmid DNA was isolated from cells containing the pGP704::sacB vector.

Example 3

Construction of pGP704::sacB::ΔCarotenoid Gene of Interest

The present Example describes the creation of crt integration vectors that enable production of deletions within the native $C_{30}$ biosynthetic pathway of the *Methylomonas* genome. Specifically, 5 constructs were made based on the positive selection vector pGP704::sacB that enable chromosomal deletions within the crtN1, crtN1/ald, crtN2 and crtN3 genes; additionally, since the crtN1, ald, crtN2 genes (crt cluster) exist in an operon and these genes are co-transcribed from the same promoter, an additional construct was created that would permit deletion of the promoter for the crt cluster. These constructs (i.e., pGP704::sacB::ΔcrtN1, pGP704::sacB::Δald(crtN1), pGP704::sacB::Δald, pGP704::sacB::ΔcrtN2, pGP704::sacB::ΔcrtN3, and pGP704::sacB::Δ promoter crt cluster, pGP704::sacB::Δ crt cluster) were generated using standard PCR and cloning methods, as described below.

PCR Amplification and Cloning of the Carotenoid Deletion DNA Fragments into pGP704::sacB.

For amplification of the subsequent PCR fragments [crtN1 deletion fragment (~3.5 kB), crtN1/ald deletion fragment #2 (~1.1 kB), crtN1/ald deletion fragment #2 (~1.1 kB), ald deletion fragment #1 (~1.1 kB), crtN2 deletion fragment #1 (~1.1 kB), crtN2 deletion fragment #2 (~1.0 kB), crtN3 deletion fragment #1 (~1.2 kB), crtN3 deletion fragment #1 (~1.1 kB), crt cluster promoter deletion fragment #1 (~2.6 kB) crt cluster promoter deletion fragment #2 (1.1 kB), crt cluster deletion fragment #1 (~2.1 kB), and crt cluster deletion #2 (2.0 kB)], the following DNA primers (Table 3) were used, along with *Methylomonas* sp. 16a chromosomal DNA as template. The methodology used for PCR reactions and cloning into *E. coli* TOP10 One Shot™ cells were the same as previously described in Example 2. Several colonies from each transformation were screened for the proper insert DNA fragments using the QIAprep® Spin Mini-prep Kit for plasmid isolation.

TABLE 3

Primers Utilized for Cloning of the Carotenoid Deletion DNA Fragments

| Deletion Fragment | Forward Primer | Reverse Primer | Size of PCR Fragment |
|---|---|---|---|
| crtN1 deletion fragment | BglII/crtN1 (deletion) 5'AGATCTCGGACGTCAT CACTCCCACAT3' (SEQ ID NO: 11) | SphI/crtN1 (deletion): 5'GCATGCGCGAGGTAGA CGTCGAACAC3' (SEQ ID NO: 12) | ~3.5 kB |
| crtN1/ ald deletion fragment #1 | BglII/ald (deletion) #1: 5'AGATCTTTGCAACGGG TATTCGACGAAGG3' (SEQ ID NO: 13) | SphI-NotI/ ald (deletion) #1: 5'GCATGCGCGGCCGCCC CGATGTTTCTGGGAAATC AGC3' (SEQ ID NO: 14) | ~1.1 kB |
| crtN1/ ald deletion fragment #2 | NotI/ald (deletion) #2: 5'GCGGCCGCAACAGCAA GCGCTGCAAGC3 (SEQ ID NO: 15) | SphI/ald (deletion) #2: 5'GCATGCGTTGCGGATA CAGCCTGTCC3' (SEQ ID NO: 16) | ~1.1 kB |
| ald deletion fragment #1 | BglII/ald (deletion) #1: 5'AGATCTTTGCAACGGG TATTCGACGAAGG3' | SphI-XhoI/ ald (deletion) #1 5'GCATGCCTCGAGTGCT ATCGTCGTCATACTCAGG | ~1.1 kB |

TABLE 3-continued

Primers Utilized for Cloning of the Carotenoid Deletion DNA Fragments

| Deletion Fragment | Forward Primer | Reverse Primer | Size of PCR Fragment |
|---|---|---|---|
| | (SEQ ID NO: 13) | CTTTG3' (SEQ ID NO: 17) | |
| ald deletion fragment #2 | XhoI/ald (deletion) #2: 5'<u>CTCGAG</u>AATCAGCAAG CGCTGCAAGC3' (SEQ ID NO: 18) | SphI/ald (deletion) #2: 5'<u>GCATGC</u>GTTGCGGATA CAGCCTGTCC3' (SEQ ID NO: 16) | ~1.0 kB |
| crtN2 deletion fragment #1 | BglII/crtN2 (deletion) #1: 5'<u>AGATCT</u>ATCCGATTCC GGTCATGCTGGA3' (SEQ ID NO: 19) | SphI/crtN2 (deletion) #1: 5'<u>GCATGC</u>CTTTGGTCAT GATGTGAGC3' (SEQ ID NO: 20) | ~1.1 kB |
| crtN2 deletion fragment #2 | MluI/crtN2 (deletion) #2 5'<u>ACGCGT</u>GGTGAGGGAC AAGATTGTGG3' (SEQ ID NO: 21) | SphI/crtN2 (deletion) #2 5'<u>GCATGC</u>TGCTTTGGTT AGCGATAGCG3' (SEQ ID NO: 22) | ~1.0 kB |
| crtN3 deletion fragment #1 | BglII/crtN3 (deletion) #1 5'<u>AGATCT</u>CCGTTCTGTA CACTGATCCG3' (SEQ ID NO: 23) | BglII-NotI/crtN3 (deletion) #1 5'<u>AGATCT</u>GCGGCGCCCA TTTGTTGCTGATAGAATC CGGC3' (SEQ ID NO: 24) | ~1.2 kB |
| crtN3 deletion fragment #2 | 5'NotI/crtN3 (deletion) #2 5'<u>GCGGCCGC</u>GCAAGCCG GCCAACAGGGATTCC3' (SEQ ID NO: 25) | 3'NotI/crtN3 (deletion) #2 5'<u>GCGGCCGC</u>CGAATACC TCGACATTCAAGC3' (SEQ ID NO: 26) | ~1.1 kB |
| crt cluster promoter deletion fragment #1 | BglII (truncated crtN1): 5'<u>AGATCT</u>AACTGTGCGA GCGCCGTAGC3' (SEQ ID NO: 27) | SphI (promoter deletion): 5'<u>GCATGC</u>CGACATCTAG TTGTCCAGC3' (SEQ ID NO: 28) | ~2.6 |
| crt cluster promoter deletion fragment #2 | BglII (promoter deletion): 5'<u>AGATCT</u>TGGCGCTTGA TCGAAATCGTCG3' (SEQ ID NO: 29) | NotI (promoter deletion): 5'<u>GCGGCCGC</u>TGTCGTGC GAATGCATCAGC3' (SEQ ID NO: 30) | ~1.1 kB |
| crt cluster deletion fragment #1 | BglII/crt cluster (deletion) #1 5'<u>AGATCT</u>TCGGTTTCGA TCAGCTCGATGCT3' (SEQ ID NO: 48) | SphI-MluI/crtN1 (deletion) 5'<u>GCATGC</u>ACGCGTTGTC GTGCGAATGCATCAGCAC GTTGCAATGTCG3' (SEQ ID NO: 49) | ~2.1 kB |
| crt cluster deletion fragment #2 | MluI/crtN2 (deletion) 5'<u>ACGCGT</u>GGTGAGGGAC AAGATTGTGG3' (SEQ ID NO: 50) | SphI/crt cluster (deletion) #2 5'<u>GCATGC</u>CATCTAAAGT CCAGGCCCTTA3' (SEQ ID NO: 51) | ~2.0 kB |

**Underlined sequences represent restriction endonuclease recognition sites.

pGP704::sacB::ΔcrtN1

Specifically, the digestion and re-ligation of a single DNA fragment that resulted in the internal deletion of the crtN1 gene from the *Methylomonas* sp. genome generated the re-NSI for the deletion of the crtN1 gene.

The crtN1 deletion fragment was digested with HindIII and XhoI. The restriction digestion products were separated on a 0.8% agarose gel, subsequently excised from the agarose gel, and the DNA was extracted using the Qiaquick® Gel Extraction Kit (Qiagen). Subsequently, the HindIIIXhoI crtN1 fragment was digested with Bg/II and SphI (~3.5 kB) and was ligated into PGP704::sacB digested with Bg/II and SphI.

Following overnight room temperature incubation, the ligation mixture was used to transform calcium chloride competent *E. coli* SY327 cells (Miller, V., L., and Mekalanos, J., J,., supra, 1984). The transformation mixture was plated onto LB+Amp[25] agar plates. Transformants were screened for the appropriate insert DNA using PCR methodology and PCR primers SphI/crtN1(deletion) (SEQ ID NO:12) and BgIII/crtN1 (deletion) (SEQ ID NO:11). A plasmid containing the correct insert DNA was digested with NotI and re-ligated. Since intra-molecular ligation events occur more frequently than inter-molecular ligation events, the ligation reaction was carried out without purifying the DNA fragment. The ligation mixture was used to transform calcium chloride competent E. coli SY327 cells as described above. Transformants were screened for the correct insert DNA fragment (~2.3 kB) by restriction digestion with BgIII and SphI. E. coli cells containing pGP704::sacB::ΔcrtN1 were streaked for isolated colonies.

pGP704::sacB::Δald(crtN1)

The re-NSI assembled for the deletion of the *Methylomonas* sp. ald and the carboxyl terminus of the crtN1 gene was prepared by ligation of two PCR fragments flanking ald (i.e., crtN1/ald deletion fragment #1 and crtN1/ald deletion fragment #2) into pGP704::sacB. Specifically, crtN1/ald deletion fragment #1 was digested with BgIII and SphI and crtN1/ald deletion fragment #2 was digested with NotI and SphI. As described previously, the restriction digestion products were separated on a 0.8% agarose gel, excised from the agarose gel, and the DNA was extracted using the Qiaquick® Gel Extraction Kit (Qiagen).

Purified crtN1/ald deletion fragment #1 was ligated into pGP704::sacB digested with BgIII and SphI. PCR amplification using PCR primers BgIII/ald (deletion)#1 (SEQ ID NO:13) and SphI-NotI/ald (deletion)#1 (SEQ ID NO:14) was used to detect E. coli transformants containing the correct DNA insert fragment. Plasmid DNA was purified from positive clones using the QIAprep® Spin Mini-prep Kit (Qiagen) and the resulting vector was digested with NotI and SphI.

Purified crtN1/ald deletion fragment #2 was ligated into the linearized pGP704::sacB::ald (crtN1) deletion fragment #1 vector described above. After overnight incubation at room temperature, the ligation mixture was used to transform E. coli SY327 cells and transformants were selected on LB+Amp[25] agar plates. PCR amplification using PCR primers BgIII/ald (deletion)#1 (SEQ ID NO:13) and SphI/ald (deletion)#2 (SEQ ID NO:16) was used to detect E. coli transformants containing the appropriate DNA insert fragment. Subsequently, E. coli cells containing pGP704::sacB::Δald(crtN1) were streaked onto LB+Amp[25] agar plates to obtain isolated colonies.

pGP704::sacB::Δald

The re-NSI assembled for the deletion of the *Methylomonas* sp. ald gene was prepared by ligating two PCR fragments flanking ald (i.e., ald deletion fragment #1 and ald deletion fragment #2) into pGP704::sacB. Specifically, ald deletion fragment #1 was digested with BgIII and SphI and ald deletion fragment #2 was digested with XhoI and SphI. As described previously, the restriction digestion products was separated on a 0.8% agarose gel, excised from the agarose gel, and the DNA was extracted using the Qiaquick® Gel Extraction Kit (Qiagen).

Purified ald deletion fragment #1 was ligated into pGP704::sacB digested with BgIII and SphI. PCR amplification using PCR primers BgIII/ald (deletion)#1 (SEQ ID NO: 13) and SphI-XhoI/ald (deletion)#1 (SEQ ID NO:17) was used to detect E. coli transformants containing the correct DNA insert fragment. Plasmid DNA was purified from positive clones using the QIAprep® Spin Mini-prep Kit (Qiagen) and the resulting vector will be digested with XhoI and SphI.

Purified ald deletion fragment #2 was ligated into the linearized pGP704::sacB::ald deletion fragment #1 vector described above. After overnight incubation at room temperature, the ligation mixture was used to transform E. coli SY327 cells and transformants was selected on LB+Amp[25] agar plates. PCR amplification using PCR primers BgIII/ald (deletion)#1 (SEQ ID NO:13) and SphI/ald (deletion)#2 (SEQ ID NO:16) was used to detect E. coli transformants containing the appropriate DNA insert fragment. Subsequently, E. coli cells containing pGP704::sacB::Δald was streaked onto LB+Amp[25] agar plates to obtain isolated colonies.

pGP704::sacB::ΔcrtN2

The construction of the re-NSI for the deletion of the crtN2 gene from the *Methylomonas* genome was carried out through the ligation of two PCR fragments flanking the crtN2 gene (i.e., crtN2 deletion fragment #1 and crtN2 deletion fragment #2) into integration vector pGP704::sacB.

The crtN2 deletion fragment #1 was removed from the TOPO TA vector by digestion with BgIII and SphI and the crtN2 deletion fragment #2 was excised from the TOPO TA vector by digestion with MluI and SphI. The restriction digestion mixture was separated by electrophoresis on a 0.8% agarose gel and the desired DNA fragments were excised and the DNA was extracted using the Qiaquick® Gel Extraction Kit (Qiagen) as described above.

The purified crtN2 deletion fragment #1 was ligated into pGP704::sacB digested with BgIII and SphI and the ligation mixture was used to transform calcium chloride competent E. coli SY327 cells as described above. PCR methodology using PCR primers BgIII/crtN2 (deletion) #1 (SEQ ID NO:19) and SphI/crtN2 (deletion) #1 (SEQ ID NO:20) was used to detect transformants that contained the desired DNA insert fragment. Plasmid DNA was purified from a positive clone using the QIAprep® Spin Mini-prep Kit (Qiagen), the pGP704::sacB::crtN2 deletion fragment #1 was digested with MluI and SphI. The MluI restriction site was located in the terminal portion of the crtN2 gene.

The purified crtN2 deletion fragment #2 was ligated into MluI and SphI digested pGP704::sacB::crtN2 deletion fragment #1 vector DNA. Following an overnight incubation at room temperature, the ligation mixture was transformed into E. coli SY327 cells and transformants were selected by plating onto LB+Amp[25] agar plates. PCR amplification using PCR primers BgIII/crtN2 (deletion) #1 (SEQ ID NO:19) and SphI/crtN2 (deletion) #2 (SEQ ID NO:22) was used to detect transformants containing the correct DNA insert fragment. Afterwards, E. coli cells containing pGP704::sacB::ΔcrtN2 were streaked onto fresh medium to obtain isolated colonies.

pGP704::sacB::ΔcrtN3

The re-NSI used to delete the crtN3 gene from the *Methylomonas* genome was generated by ligating two PCR fragments (i.e., crtN3 deletion fragment #1 and crtN3 deletion fragment #2) into pGP704::sacB.

The crtN3 deletion fragment #1 (~1.1 kB) was excised from pCR2.1 (TOPO TA vector) by restriction digestion with BamHI and XhoI. The restriction digestion mixture was separated on a 0.8% agarose gel and the crtN3 deletion fragment #1 was extracted using the Qiaquick® Gel Extraction Kit (Qiagen). This BamHI and XhoI fragment was then digested with BgIII and was ligated into the BgIII site of the dephosphorylated pGP704::sacB. After an overnight incubation at room temperature, the ligation mixture was used to transform calcium chloride competent E. coli SY327. The transformation mixture was plated onto LB+Amp[25] agar plates. Individual colonies were screened for the appropriate insert DNA using PCR methodology and PCR primers Bg/II/crtN3 (deletion) #1 (SEQ ID NO:23) and Bg/II-NotI/crtN3 (deletion) #1 (SEQ ID NO:24) with *Methylomonas* sp. 16a plasmid DNA as template. Plasmid DNA was isolated from the positive clones, pGP704::sacB::crtN3 deletion fragment #1.

The crtN3 deletion fragment #2 was isolated from the TOPO TA vector by digestion with EcoRI and was separated on a 0.8% agarose gel. The ~1.1 kB DNA fragment was extracted from the gel using the Qiaquick® Gel Extraction Kit. The crtN3 deletion fragment #2 was digested with NotI and ligated into the dephosphorylated NotI site of pGP704::sacB::crtN3 deletion fragment #1. The ligation mixture was used to transform *E. coli*SY327. Several colonies were screened using PCR methodology (Perkin Elmer Ampli-Taq® and Epicentre Fail-Safe™ enzymes) with the Bg/II/crtN3 (deletion) #1 (SEQ ID NO:23) and the 3'NotI/crtN3 (deletion) #2 (SEQ ID NO:26) and plasmid template DNA. Plasmid DNA was isolated from the positive clone and digested with MluI and NdeI to confirm the presence of the correct insert DNA fragment. *E. coli* cells containing pGP704::sacB::ΔcrtN3 were streaked onto fresh medium to obtain isolated colonies.

pGP704::sacB::Δ Promoter crt Cluster

To prepare for the construction of the crt cluster promoter deletion vector (pGP704::sacB::Δ promoter crt cluster), an intermediary vector was generated, pGP704::sacB::hybrid. The components of pGP704::sacB::hybrid were pGP704::sacB, (aid) deletion fragment #1 and crtN3 deletion fragment #2. The purpose of this vector was to make it easier to distinguish between fragments that had been cut with two restriction endonucleases as opposed to only one. This can be visualized on an agarose gel with the presence of an ~1.1 kB fragment when digested with Bg/II and SphI.

The Bg/II and SphI digested pGP704::sacB::hybrid was ligated with the crt cluster promoter deletion fragment #1 (~2.6 kB) which had been prepared using methods similar to those described above. The ligation mixture was used to transform *E. coli* SY327 and the transformation mixture was plated onto LB+Amp$^{25}$ agar plates. Colonies containing the correct insert DNA fragment were screened using plasmid isolation, restriction digestion and agarose gel electrophoresis.

The pGP704::sacB::crt cluster promoter deletion fragment #1 was digested with Bg/II and NotI, separated on a 0.8% agarose gel and extracted from the agarose gel using the Qiaquick® Gel Extraction Kit. The Bg/II and NotI digested pGP704::sacB::crt cluster promoter deletion fragment #1 was ligated with the crt cluster promoter deletion fragment #2. The ligation mixture was used to transform *E. coli* SY327 and was plated onto LB+Amp$^{25}$ agar plates as described above. Colonies containing the correct insert DNA fragment were identified by plasmid isolation and restriction digestions using methods similar to those described above. Cells containing positive vectors (pGP704::sacB::Δ crt cluster promoter) were streaked for isolated colonies.

pGP704::sacB::Δcrt Cluster

The construction of the re-NSI for the deletion of the crt cluster from the *Methylomonas* genome was carried out through the ligation of two PCR fragments flanking the crt cluster (i.e. crt cluster deletion fragment #1 and crt cluster deletion fragment #2) into integration vector pGP704::sacB::CDstuffer1 (contains two 1 kb DNA fragments that flank the crt cluster). This vector was originally constructed for the purpose of deleting the Crt cluster. However, the identification of trans-conjugates in which the Crt cluster had been deleted were not identified from the *Methylomonas* genome. Therefore, a different approach was used by extending the size of the flanking DNA fragments to ~2 kb to increase the probability of identifying cells the have undergone a double crossover event leading to the deletion of the Crt cluster.

The crt deletion fragment #1 was excised from the TOPO TA vector by digestion with Bg/II and MluI and the crt deletion fragment #2 was removed from the TOPO TA vector by digestion with MluI and SphI. The restriction digestion mixture was separated by electrophoresis on a 0.8% agarose gel. The correct DNA fragments were excised and the DNA was extracted using the Qiaquick Gel Extraction Kit (Qiagen) using the same method as described above.

The purified crt cluster deletion fragment #2 as ligated into pGP704::sacB::CDstuffer1 digested with MluI and SphI and the ligation mixture was used to transform calcium chloride competent *E. coil* SY327 cells as described above. Plasmid DNA was purified from several transformants using the QIAprep Spin Mini-prep Kit (Qiagen). Restriction digestions analysis using restriction endonucleases MluI and SphI was used to identify transformant that contained the Crt cluster deletion fragment #2. Plasmid DNA that contain the correct insert fragment were subsequently digested with Bg/II and MluI.

The purified Crt cluster deletion fragment #1 was ligated into Bg/II and MluI digested pGP704::sacB::crt cluster deletion fragment #2 vector DNA. Following an overnight incubation at room temperature, the ligation mixture was transformed into *E. coli* SY327 cells and transformants were selected by plating onto LB/Amp$^{50}$ agar plates. Plasmid DNA was isolated from several colonies and restriction digestion with Bg/II and MluI was used to identify plasmid DNA contain the correct insert DNA The pGP704::sacB::crt cluster deletion vector also contains a gene that confers resistance to ampicillin. However, ampicillin selection is not straight forward when culturing *Methylomonas*. In vitro transposition was used to inactivate the ampicillin resistance gene and to insert a kanamycin resistance gene to the vector. The pGP704::sacB::crt cluster deletion vector severed as the recipient DNA in the in vitro transposition reaction (Epicentre, Madison, Wis.). Following the manufacturer's protocol, the EZ::TN<Kan-2> transposon was used to randomly insert the kanamycin resistance gene into the pGP704::sacB::crt cluster deletion vector. The transposition reaction was heat inactivated at 70° C. for 10 minutes and the transposition mixture was used to transform calcium chloride competent *E. coli* SY327 cells. The transformation mixture was plated onto LB+Kan$^{50}$ plates. The colonies were patched on LB+Amp$^{50}$ and LB+Kan$^{50}$ to identify cells that contained the pGP704::sacB::crt cluster deletion vector that had received the EZ::TN<Kan-2> insertion into the ampicillin resistance gene. *E. coli* cells that were Kan$^R$ and Amp$^S$ were streaked onto fresh medium and severed as the donor cells in the tri-parental matings.

Example 4

Tri-Parental Conjugation of the Various CRT Integration Vectors into *Methylomonas* sp. 16A Each of the crt integration vectors from Example 3 (i.e., pGP704::sacB::ΔcrtN1, pGP704::sacB::Δald(crtN1), pGP704::sacB::Δald, pGP704::sacB::ΔcrtN2, pGP704::sacB::ΔcrtN3, pGP704::sacB::Δ crt cluster promoter, and pGP704::sacB::crt cluster deletion) were transferred into *Methylomonas* sp. 16a via triparental conjugation. Specifically, the following were used as recipient, donor, and helper, respectively: *Methylomonas* sp. 16a, *E. coli* SY327 containing the crt integration vectors, and *E. coli* containing pRK2013.

Theory of the Conjugation

The mobilization of vector DNA into *Methylomonas* occurs through conjugation (tri-parental mating). The pGP704::sacB vector used to make chromosomal mutations in *Methylomonas* has a R6K origin of replication, which requires the Π protein. This vector can replicate in *E. coli* strain SY327, which expresses the Π protein. However, this protein is not present in the *Methylomonas* genome. Therefore, once the vector DNA has entered into *Methylomonas*, it is unable to duplicate itself. If the vector also contains a DNA segment that shares homology to a region of the *Methylomonas* genome, the vector can be integrated into the host's genome through homologous recombination. The homologous recombination system of *Methylomonas* appears to be similar to that of other Gram-negative organisms.

In the case of *Methylomonas*, the mobilizable plasmid (pGP704::sacB) was used to transfer the re-NSI into this bacterium. The conjugative plasmid (pRK2013), which resided in a strain of *E. coli*, facilitated the DNA transfer.

Growth of *Methylomonas* sp. 16a

The growth of *Methylomonas* sp. 16a for tri-parental mating initiated with the inoculation of an −80° C. frozen stock culture into 20 mL of BTZ medium containing 25% methane, as described in Example 1. The culture was grown at 30° C. with aeration until the density of the culture was saturated. This saturated culture was in turn used to inoculate 100 mL of fresh BTZ medium containing 25% methane. The 100 mL culture was grown at 30° C. with aeration until the culture reached an $OD_{600}$ between 0.7 to 0.8. To prepare the cells for the tri-parental mating, the *Methylomonas* sp. 16a cells were washed twice in an equal volume of BTZ medium. The *Methylomonas* cell pellets were re-suspended in the minimal volume needed (approximately 200 to 250 μL). Approximately 40 μL of the re-suspended *Methylomonas* cells were used in each tri-parental mating experiment.

Growth of the *Escherichia coli* Donor and Helper Cells

Isolated colonies of the *E. coli* donor (pGP704::sacB::NSI) and helper (containing conjugative plasmid pRK2013) cells were used to inoculate 5 mL of LB broth containing 25 μg/μL Kan; these cultures were grown overnight at 30° C. with aeration. The following day, the *E. coli* donor and helper cells were mixed together and incubated at 30° C. for ~2 hours. Subsequently, the cells were washed twice in equal volumes of fresh LB broth to remove the antibiotics.

Tri-Parental Mating: Mobilization of the Donor Plasmid into *Methylomonas* Strain 16a Approximately 40 μL of the re-suspended *Methylomonas* cells were used to re-suspend the combined *E. coli* donor and helper cell pellets. After thoroughly mixing the cells, the cell suspension was spotted onto BTZ agar plates containing 0.05% yeast extract. The plates were incubated at 30° C. for 3 days in a jar containing 25% methane.

Following the third day of incubation, the cells were scraped from the plate and re-suspended in BTZ broth. The entire cell suspension was plated onto several BTZ agar plates containing Amp[35]. The plates were incubated at 30° C. in a jar containing 25% methane until colonies were visible (~4-7 days).

Individual colonies were streaked onto fresh BTZ +Amp[35] agar plates and incubated 1-2 days at 30° C. in the presence of 25% methane. These cells were used to inoculate bottles containing 20 mL of BTZ and 25% methane. After overnight growth, 5 mL of the culture was concentrated by centrifugation using a tabletop centrifuge. Then, to rid the cultures of *E. coli* cells that were introduced during the tri-parental mating, the cells were inoculated into 20 mL of BTZ liquid medium containing nitrate (10 mM) as the nitrogen source, methanol (200 mM), and 25% methane and grown overnight at 30° C. with aeration. Cells from the BTZ (nitrate) cultures were again inoculated into BTZ and 25% methane and grown overnight at 30° C. with aeration. The cultures were monitored for *E. coli* growth by plating onto LB agar plates to verify the success of the *E. coli* elimination.

Example 5

Evaluation of *Methylomonas* Transconjugants Containing the Various CRT Integration Vectors Following the mobilization of the various crt integration constructs into *Methylomonas* sp. 16a, as described in Example 4, a two-step selection strategy was applied as described below to identify the ΔcrtN1, Δald(crtN1), Δald, ΔcrtN2, ΔcrtN3, Δcrt cluster promoter, and Δcrt cluster allelic exchange mutants (see also FIG. 4). Four "white" or "pigmentless" mutants were produced comprising the ΔcrtN1, Δald(crtN1), Δcrt cluster promoter, or Δcrt cluster. In contrast, successful deletion of ald, crtN2 or crtN3 genes resulted in *Methylomonas* transformants that still possessed the ability to produce a pink pigment. However, the carotenoid(s) that is produced in each mutant is distinct, indicating that the enzymes act at different stages along the pathway for $C_{30}$ carotenoid synthesis.

Preliminary Screening for Allelic Exchange Mutants

Cultures free of *E. coli* cells were passaged several times in fresh medium (1 mL of culture into 20 mL of fresh BTZ medium), to increase the probability of occurrence of a second crossover event. Subsequently, cells were plated onto BTZ and sucrose (5%) agar plates. Those cells grown on plates containing sucrose had lost the integration vector, which contained the sacB gene. However, the loss of the vector sequences could be due to the second crossover event occurring either on the same or opposite side of the re-NSI that was present on the insert DNA. If the second crossover event had occurred on the same side of the re-NSI as the first crossover event, the wildtype gene of interest would be regenerated. In contrast, if the second crossover event occurred on the opposite side of the re-NSI as the first crossover event, the deletion of the gene of interest would be established in the *Methylomonas* genome.

Verification of the Chromosomal Deletion of the *Methylomonas* sp. 16a Carotenoid Genes Chromosomal DNA was purified from several cultures that had grown on the sucrose plates using the MasterPure™ DNA Purification Kit (EPICENTRE®; Madison, Wis.). Then, PCR amplification methods were applied to confirm each suspected deletion, using the primers described below in Table 4.

TABLE 4

Primers Used to Verify the Deletion of the *Methylomonas* sp. 16a Carotenoid Genes

| Carotenoid Gene(s) | Forward Primer | Reverse Primer | Intact Fragment | Deletion Fragment |
|---|---|---|---|---|
| crtN1 | BglII/crtN1 (deletion)<br>5'-<u>AGATCT</u>CGGACGTCATCACTCCCACAT-3'<br>(SEQ ID NO: 11) | SphI/crtN1 (deletion)<br>5'-<u>GCATGC</u>GCGAGGTAGACGTCGAACAC-3'<br>(SEQ ID NO: 12) | ~3.5 kB | ~2.2 kB |
| crtN1 | NcoI/crtN1<br>5'-CCATGGCCAACACCAAACACATCATCAT<br>(SEQ ID NO: 52) | ScaI/NdeI/crtN1<br>5'-AGTACTCCGCATATGTCAGGCTTTGGCTTTGGCTTTTTTCAGCCAGGC3'<br>(SEQ ID NO: 53) | 1.7 kB | 0.3 kB |
| crtN1/ald | BglII/ald (deletion) #1:<br>5'-<u>AGATCT</u>TTGCAACGGGTATTCGACGAAGG-3'<br>(SEQ ID NO: 13) | SphI/ald (deletion) #2:<br>5'-<u>GCATGC</u>GTTGCGGATACAGCCTGTCC-3'<br>(SEQ ID NO: 16) | ~3.7 kB | ~2.1 kB |
| crtN2 | BglII/crtN2 (deletion) #1:<br>5'-<u>AGATCT</u>ATCCGATTCCGGTCATGCTGGA-3'<br>(SEQ ID NO: 19) | SphI/crtN2 (deletion) #2:<br>5'-<u>GCATGC</u>TGCTTTGGTTAGCGATAGCG-3'<br>(SEQ ID NO: 22) | ~3.4 kB | ~2.1 kB |
| ald | BglII//ald (deletion) #1<br>5'-<u>AGATCT</u>TTGCAACGGGTATTCGACGAAGG3'<br>(SEQ ID NO: 13) | SphI/ald (deletion) #2<br>5'-<u>GCATGC</u>GTTGCGGATACAGCCTGTCC3'<br>(SEQ ID NO: 16) | 3.7 kB | 2.2 kB |
| crtN3 | BglII/crtN3 (deletion) #1:<br>5'-<u>AGATCT</u>CCGTTCTGTACACTGATCCG-3'<br>(SEQ ID NO: 23) | 3'NotI/crtN3 (deletion) #2:<br>5'-<u>GCGGCCGC</u>CGAATACCTCGACATTCAAGC-3'<br>(SEQ ID NO: 26) | ~3.5 kB | ~2.3 kB |
| crt cluster promoter | BglII (truncated crtN1):<br>5'-<u>AGATCT</u>AACTGTGCGAGCGCCGTAGC-3'<br>(SEQ ID NO: 27) | NotI (promoter deletion)<br>5'-<u>GCGGCCGC</u>TGTCGTGCGAATGCATCAGC-3'<br>(SEQ ID NO: 30) | ~4.3 kB | ~2.1 kB |
| crt cluster | BglII (promoter deletion):<br>5'-<u>AGATCT</u>TGGCGCTTGATCGAAATCGTCG3'<br>(SEQ ID NO: 29) | SphI/crtN2 (deletion) #2:<br>5'-<u>GCATGC</u>TGCTTTGGTTAGCGATAGCG-3'<br>(SEQ ID NO: 22) | ~7.2 kB | ~2.1 kB |

**Underlined sequences represent restriction endonuclease recognition sites.

ΔcrtN1, Δald(crtN1), Δcrt Cluster Promoter, and Δcrt Cluster Mutants

The *Methylomonas* strains that had "white" phenotypes, designated herein as(MWM1400 (ΔcrtN1), MWM1000 (Δald(crtN1)), MWM100 (Δcrt cluster promoter), and MWM1600 (Δcrt cluster) were easily distinguished from the wild-type cells. However, the construction of these strains was still verified via PCR amplification using PCR primers Bg/II/ald (deletion) #1 (SEQ ID NO:13) and SphI/ald (deletion) #2 (SEQ ID NO:16), which permitted cells that contained an intact ald gene (wherein the expected size of the PCR product was ~3.7 kB, see Table 4) to be distinguished from those that contained a deletion of the ald gene (wherein the expected size of the PCR product was ~2.1 kB). Two of the three cultures produced a PCR product that was ~2.1 kB, while the third culture appeared to have the wildtype gene present. Thus, these two PCR reactions confirmed the deletion of the crtN1/ald genes in the genome of *Methylomonas* MWM1000. To verify the construction of the crtN1 deletion mutant, PCR amplification using PCR primers Bg/II/crtN1 (deletion) (SEQ ID NO: 11) and SphI/crtN1 (deletion) (SEQ ID NO: 12) was employed. Cells having an intact crtN1 gene produced a DNA fragment that was ~3.5 kB, whereas cells comprised of a disrupted crtN1 gene produced a DNA fragment of ~2.2 kB. An additional pair of primers was used to verify the construction of the crtN1 deletion. PCR primers NcoI/crtN1 (SEQ ID NO: 52) and ScaI/NdeI/crtN1 (SEQ ID NO: 53) were used as an additional set of primers to verify the construction of the crtN1 deletion. Cells having an intact crtN1 gene produced a DNA fragment that was ~1.7 kB, whereas cell possessing a disrupted crtN1 gene resulted in a fragment of ~0.3 kB. Similarly, the construction of *Methylomonas* MWM 1100 (Δcrt cluster promoter) was confirmed using PCR methodology and PCR primers Bg/II (truncated crtN1) (SEQ ID NO:27) and NotI (promoter deletion) (SEQ ID NO:30). Cells that contained an intact promoter region for the crt cluster had the expected PCR product size of ~4.3 kB. In contrast, cells in which the promoter region of the crt cluster had been deleted, gave rise to PCR products that were ~2.1 kB (Table 4). Likewise, the construction of *Methylomonas* MWM1600 (Δcrt cluster) was established using PCR methodology and PCR primers Bg/II (promoter deletion) (SEQ ID NO:29) and SphI/crtN2 (deletion) #2 (SEQ ID NO:22). Cells that remained wild-type for the crt cluster were expected to produce a PCR product that was ~7.2 kB. This long PCR fragment could not be detected under our PCR reaction conditions, thus we used the absence of a PCR product to indicate that the wild-type genes were the product of the double-crossover event. In contrast, the PCR fragment was ~2.1 kB for the cells in which the entire crt gene cluster had been deleted.

ΔcrtN2, ΔcrtN3, and Δald Mutants

The identification of the "pink" mutants required more effort since these cells could not be easily distinguished from the wild-type cells. Nevertheless, generally less than five cultures were evaluated for the verification of the *Methylomonas* "pink" mutants. Cells containing a deletion of the crtN2 gene, designated herein as MPM1200, were easily distinguished from wild-type cells using PCR methodology and PCR primers Bg/II/crtN2 (deletion) #1 (SEQ ID NO:19) and SphI/crtN2 (deletion) #2 (SEQ ID NO:22). The wild-type cells gave a PCR fragment that was ~3.4 kB, while the cells containing the crtN2 deletion gave a fragment that was ~2.1 kB (Table 4). The verification of the *Methylomonas* crtN3 deletion mutant, designated herein as MPM1000, was demonstrated using PCR amplification with PCR primers Bg/II/crtN3 (deletion) #1 (SEQ ID NO:23) and 3'NotI/crtN3 (deletion) #2 (SEQ ID NO:26). An ~2.3 kB PCR fragment was detected for the ΔcrtN3 mutant as compared to an ~3.5 kB PCR fragment that was produced by the wild-type *Methylomonas* cells (Table 4). The affirmation of the *Methylomonas* ald deletion mutant, designated herein as MPM1300, was revealed using PCR amplification with PCR primers Bg/II/ald (deletion) #1 (SEQ ID NO:13) and SphI/ald (deletion) #2 (SEQ ID NO:16). The wild-type cells gave a PCR fragment that was ~3.7 kB, while cells containing the ald deletion gave a fragment that was ~2.2 kB (Table 4).

Example 6

Analysis of $C_{30}$ Carotenoids Produced by *Methylomonas* sp. 16a Deletion Mutants using HPLC-Photodiode Array To investigate the effect of deleting genes involved in the biosynthesis of the $C_{30}$ carotenoid from the *Methylomonas* sp. 16a genome, the carotenoids were extracted from each mutant strain, using two different methods, and evaluated using high performance liquid chromatography with photodiode array detection (HPLC-photodiode array). As a control, the carotenoid from the wild-type *Methylomonas* strain was also extracted and analyzed using similar methods.

Methanol Extraction Method

Each *Methylomonas* culture (wild-type, ΔcrtN1, Δald (crtN1), ΔcrtN2, ΔcrtN3, Δcrt promoter deletion, and Δcrt cluster deletion mutant) was grown with aeration in two 500 mL bottles containing 100 mL of BTZ and 25% methane until they reached saturation (~24 hr). The cells were harvested by centrifugation for 15 min at 4000 rpm. The cell pellet was extracted twice with 10 mL of methanol for 15 min at room temperature with agitation. This step was followed by two extractions with 10 mL of a methanol/acetone (1:1) mixture for 15 min at room temperature also with agitation. The extracted $C_{30}$ carotenoids were dried with nitrogen and were subsequently re-dissolved in 1 mL of methanol.

THF/Methanol Extraction Method

As in the methanol extraction method, each *Methylomonas* culture to be analyzed was grown in two 500 mL bottles containing 100 mL of BTZ and 25% methane until saturation (~24 hr). The cells were split into two aliquots and harvested by centrifugation. For one aliquot, the cell pellets were dried in an oven at ~100° C. for ~24 hr and the dry cell mass was determined. The other aliquot was used for $C_{30}$ carotenoid extractions. The cells were lysed using glass beads (0.5 mL/sample). Also added to each sample was 150 µL of the internal standard, ethyl-β-apo-8'-carotene (trans) (100 mg/L stock solution) and 5 mL of a THF (tetrahydrofuran)/methanol (1:1) solution. This mixture was vortexed for ~2 min, followed by a 15 min centrifugation at 8,000 rpm. The supernatant was collected and the sample was vortexed again for ~2 min and centrifuged at 8,000 rpm for another 15 min. The supernatants were combined and were dried using nitrogen. The carotenoid samples were stored at −80° C. until analyzed using HPLC-photodiode array.

HPLC-Photodiode Array Analysis

A Beckman System Gold® HPLC with Beckman Gold®0 Nouveau Software (Beckman Coulter, Inc. Fullerton, Calif.) was used for the study. A 0.1 mL aliquot of the crude acetone extraction was loaded onto a 150 mm×4.6 mm ZORBAX C18 (3.5 µm particles) column (Agilent Technologies Inc., Wilmington, Del.). The flow rate was 1 mL/min using a solvent gradient consisting of Buffer A and Buffer B. Buffer A was 95% acetonitrile and 5% dH2O, Buffer B was 100% tetrahydrofuran. The running program was: 0-1st min, 95% Buffer A and 5% Buffer B; 1-11th min, linear gradient from 95% Buffer A and 5% Buffer B to 60% Buffer A and 40% Buffer B; 11-22nd min, linear gradient from 60% Buffer A and 40% Buffer B to 50% Buffer A and 50% Buffer B; 22-25th min, 95% Buffer A and 5% Buffer B. The spectrum data was collected by a Beckman photodiode array detector (Model 168).

In the HPLC-diode array analysis, two peaks were detected for the wild-type strain, a large peak that eluted at ~5.5 min and a smaller peak that eluted at ~7 min. Although these two peaks had different elution profiles, their UV spectrums were very similar, suggesting that they were similar forms of the same $C_{30}$ carotenoid (data not shown). When the extracts from *Methylomonas* sp. strain MWM1000 (Δald/crtN1) were evaluated via HPLC-photodiode array, neither of the two peaks seen for wild-type *Methylomonas* sp. 16a were observed. This result suggests that the deletion of the aldehyde dehydrogenase (aid) gene and the crtN1 gene impaired *Methylomonas*' ability to make the $C_{30}$ carotenoid. This was a surprising result, because it was expected that the ald gene encoded an enzyme that modified a $C_{30}$ molecule further down the biosynthesis chain. Interestingly, when only the crtN1 gene was deleted, it was also failed to produce the two peaks detected for the wild-type *Methylomonas*. This suggested that perhaps it was the partial deletion of the crtN1 gene and not the deletion of the ald gene in the Δald/crtN1 strain that was responsible of the loss of the pink pigment in these strains. As expected, when the promoter region of the crt cluster (MWM1100) was deleted or the entire crt cluster (MWM1600) was deleted, a "white" mutant was generated (i.e. the $C_{30}$ carotenoid was no longer produced).

Evaluation of the crtN2 and crtN3 deletion strains yielded very different results when analyzed using HPLC-photodiode array. It was found that *Methylomonas* MPM1200 (ΔcrtN2) had an elution profile that was very similar to that of the wild-type *Methylomonas* sp. 16a, i.e., two peaks were observed. However, the ratios of the two peaks were distinct. The levels of Peak 2 were similar between the two strains. Interestingly, the level of Peak 1 was approximately 75% lower in MPM1200 as compared to *Methylomonas* sp. 16a, i.e., 15 mAU versus 60 mAU, respectively. However, the exact structure of the $C_{30}$ carotenoid present in each fraction is not known. In contrast to MPM1200, an increase (~15%) in the biosynthesis of the $C_{30}$ carotenoid was observed in MPM1000 (ΔcrtN3).

As described above, "Clustal W" analysis, conducted to show the relationship between crtN1, crtN2, crtN3, and sqs, revealed that crtN3 is not closely linked to crtN1 and crtN2 (FIG. 3). When crtN3 (which contains sequences that are homologous to domains of other FAD-dependent oxidoreductases) was viewed in context of its surrounding ORFs, it was observed that crtN3 is located at the end of a cluster of ORFs that have high homology to proteins that play a role in fatty acid metabolism (FIG. 2). It is hypothesized that the crtN3 may have an indirect role in carotenoid biosynthesis and perhaps the deletion of crtN3 from the *Methylomonas* genome relieved a drain on common intermediates. It is possible that crtN3 may also be involved in fatty acid metabolism; however, additional experiments are necessary to confirm this hypothesis.

Example 7

Construction of the Carotenoid Double Mutants

MWM1300 (Δald(crtN1)+ΔcrtN3), MWM1200 (Δcrt Cluster Promoter+ΔcrtN3, MWM1800 (ΔcrtN1 +ΔcrtN3), and MWM1900 (Δcrt Cluster+ΔcrtN3)

Since an increase in the production of the $C_{30}$ carotenoid was observed when the crtN3 gene was deleted from *Methylomonas* sp. 16a background, it was hypothesized that the crtN3 deletion would also have a positive impact on the synthesis of the $C_{40}$ carotenoids (i.e. canthaxanthin and astaxanthin). Thus, deletion of crtN3 was made in each of the *Methylomonas* "white" mutants (MWM1000, MWM1100, MWM1400, and MWM1600).

The pGP704::sacB::ΔcrtN3 integration plasmid was transferred into MWM1000, MWM1100, MWM1400, and MWM1600 via conjugation using the same procedures described above in Example 4. Once inside the *Methylomonas*, the crtN3 gene was deleted via homologous recombination using the same two step strategy described in Example 5. Once again, the deletion of the crtN3 gene was confirmed using PCR methodology and PCR primers Bg/II/crtN3 (deletion) #1(SEQ ID NO:23) and 3' NotI/crtN3 (deletion) #2 (SEQ ID NO:26). If the "white" mutants still contained the intact crtN3 gene, a PCR fragment that was ~3.5 kB was produced. In contrast, cells in which the crtN3 gene was deleted produced an ~2.3 kB PCR fragment (Table 4). The new *Methylomonas* strains that were produced are referred to herein as MWM1200 (Δcrt cluster promoter+ΔcrtN3), MWM1300 (Δald(crtN1)+ΔcrtN3), MWM1800 (ΔcrtN1+ΔcrtN3), and MWM1900 (Δcrt cluster+ΔcrtN3).

Example 8

Synthesis of Codon-Optimized Genes for Expression In *Methylomonas* sp. 16A

This Example describes the design and synthesis of a codon-optimized β-carotene ketolase gene crtW and a β-carotene hydroxylase gene crtZ for production of canthaxanthin, astaxanthin and intermediates in *Methylomonas* sp. 16a based on the crtW and crtZ sequences from *Agrobacterium aurantiacum*.

Source of the Genes

*Agrobacterium aurantiacum* is a marine bacterium that naturally produces astaxanthin. The relative percentages of astaxanthin and 4-ketozeaxanthin (adonixanthin) to the total carotenoids produced in this strain are reported to be 19.5% and 70.3%, respectively (Yokoyama et al., *Biosci. Biotech. Biochem.*, 58:1842-1844 (1994)). The carotenoid biosynthesis gene cluster in *A. aurantiacum* contains the β-carotene ketolase gene crtW and the β-carotene hydroxylase gene crtZ (Misawa et al., *J. Bacteriol.*, 177:6575-6584 (1995)). The ketolase and the hydroxylase have low substrate specificity, resulting in the production of many presumed intermediates of astaxanthin, i.e., adonixanthin, adonirubin, canthaxanthin, 3'-hydroxyechinenone, 3-hydroxyechinenone. To ensure optimal expression in *Methylomonas* sp. 16a to produce more desired products such as canthaxanthin or astaxanthin, the codons of the A. aurantiacum crtW and crtZ genes were codon optimized based on the preferred codon usage table for *Methylomonas* sp. 16a (Table 5).

Determination of Preferred Codon Usage Table for *Methylomonas* sp. 16a

The genome of *Methylomonas* sp. 16a was sequenced and 201 highly expressed *Methylomonas* genes, according to microarray analysis, were used to determine the preferred codon usage profile in *Methylomonas* sp. 16a, which is shown in Table 5. The coding regions of these genes, comprising 164,751 bp, were translated by the Editseq program of DNASTAR to the corresponding 54,917 amino acids. The column titled "Number" refers to the number of times a given codon encodes a particular amino acid in the sample of 54,917 amino acids. The column titled "Fraction" refers to the frequency that a given codon encodes a particular amino acid. The stop codons were not included in the coding regions for tabulation.

TABLE 5

Preferred Codon Usage Table for *Methylomonas* sp. 16a

| Amino Acid | Codon | Number | Fraction |
|---|---|---|---|
| Gly | GGG | 288.00 | 0.07 |
| Gly | GGA | 300.00 | 0.07 |
| Gly | GGU | 1168.00 | 0.27 |
| Gly | GGC | 2541.00 | 0.59 |
| Glu | GAG | 966.00 | 0.28 |
| Glu | GAA | 2514.00 | 0.72 |
| Asp | GAU | 1435.00 | 0.46 |
| Asp | GAC | 1712.00 | 0.54 |
| Val | GUG | 1287.00 | 0.32 |
| Val | GUA | 508.00 | 0.13 |
| Val | GUU | 717.00 | 0.18 |
| Val | GUC | 1450.00 | 0.37 |
| Ala | GCG | 1576.00 | 0.31 |
| Ala | GCA | 607.00 | 0.12 |
| Ala | GCU | 658.00 | 0.13 |
| Ala | GCC | 2279.00 | 0.45 |

TABLE 5-continued

Preferred Codon Usage Table for *Methylomonas* sp. 16a

| Amino Acid | Codon | Number | Fraction |
|---|---|---|---|
| Lys | AAG | 1055.00 | 0.35 |
| Lys | AAA | 1988.00 | 0.65 |
| Asn | AAU | 877.00 | 0.40 |
| Asn | AAC | 1317.00 | 0.60 |
| Met | AUG | 1443.00 | 1.00 |
| Ile | AUA | 301.00 | 0.09 |
| Ile | AUU | 933.00 | 0.28 |
| Ile | AUC | 2122.00 | 0.63 |
| Thr | ACG | 544.00 | 0.19 |
| Thr | ACA | 263.00 | 0.09 |
| Thr | ACU | 380.00 | 0.13 |
| Thr | ACC | 1738.00 | 0.59 |
| Trp | UGG | 600.00 | 1.00 |
| Cys | UGU | 151.00 | 0.24 |
| Cys | UGC | 474.00 | 0.76 |
| Tyr | UAU | 779.00 | 0.52 |
| Tyr | UAC | 723.00 | 0.48 |
| Phe | UUU | 793.00 | 0.38 |
| Phe | UUC | 1308.00 | 0.62 |
| Ser | AGU | 317.00 | 0.10 |
| Ser | AGC | 868.00 | 0.27 |
| Ser | UCG | 733.00 | 0.23 |
| Ser | UCA | 318.00 | 0.10 |
| Ser | UCU | 291.00 | 0.09 |
| Ser | UCC | 701.00 | 0.22 |
| Arg | AGG | 186.00 | 0.06 |
| Arg | AGA | 287.00 | 0.09 |
| Arg | CGG | 411.00 | 0.13 |
| Arg | CGA | 250.00 | 0.08 |
| Arg | CGU | 693.00 | 0.22 |
| Arg | CGC | 1292.00 | 0.41 |
| Gln | CAG | 893.00 | 0.40 |
| Gln | CAA | 1345.00 | 0.60 |
| His | CAU | 635.00 | 0.51 |
| His | CAC | 600.00 | 0.49 |
| Leu | UUG | 1825.00 | 0.38 |
| Leu | UUA | 319.00 | 0.07 |
| Leu | CUG | 1980.00 | 0.41 |
| Leu | CUA | 172.00 | 0.04 |
| Leu | CUU | 221.00 | 0.05 |
| Leu | CUC | 277.00 | 0.06 |
| Pro | CCG | 1104.00 | 0.44 |
| Pro | CCA | 443.00 | 0.18 |
| Pro | CCU | 441.00 | 0.18 |
| Pro | CCC | 520.00 | 0.21 |

Design and Synthesis of the Synthetic Genes for β-Carotene Ketolase and β-Carotene Hydroxylase The β-carotene ketolase gene (SEQ ID NO:31) and the β-carotene hydroxylase gene (SEQ ID NO:32) from *Agrobacterium aurantiacum* are 729 bp and 489 bp in length, respectively (U.S. Pat. No. 5,972,690; GenBank® D58420). The codon-optimized 0-carotene ketolase gene and the β-carotene hydroxylase gene were first designed by back translating the amino acid sequences of the *A. aurantiacum* CrtW and the CrtZ, according to the preferred codon usage table for *Methylomonas* sp. 16a. To further optimize the genes, most strong hairpin structures were disrupted by replacing with alternative sub-optimal codons. The AT-rich mRNA instability region (Guhaniyogi, G. and J. Brewer, *Gene*, 265(1-2):11-23 (2001)) and the long runs of the same nucleotide were also eliminated. In the case of a string of more than 3 or 4 of the same amino acids, a sub-optimal codon was also introduced to prevent shortage of the most preferred codon pool for this amino acid. The ribosomal binding site (RBS) was engineered upstream of the start codon as the RBS sequence from pTrcHis2-TOPO vector (Invitrogen, Carlsbad, Calif.). Several restriction sites were also engineered at the 5' and 3' ends of the genes to facilitate cloning.

A comparison between the synthetic crtW gene (SEQ ID NO:7) and the synthetic crtZ gene (SEQ ID NO:8) with the full-length wildtype crtW and crtZ sequences from *A. aurantiacum* is shown in FIG. 6 and FIG. 7, respectively, wherein nucleotides in shaded boxes correspond to nucleotides that are identical between the native gene and the synthetic gene. For both crtW and crtZ, there is 84% nucleotide identity between the native gene and the synthetic gene. For the codon-optimized crtW gene, 99 codons were optimized, while for the codon-optimized crtZ gene 73 codons were optimized. None of the modifications in the codon-optimized gene changed the amino acid sequence of the encoded ketolase protein (SEQ ID NO:33) or hydroxylase protein (SEQ ID NO:34). The synthetic crtW gene was synthesized and cloned onto the pCRScript vector by Aptagen Inc. (Herndon, Va.) to form pCRScript-Dup1. The synthetic crtZ gene was synthesized and cloned onto the pUC18 vector by GenScript Corp. (Scotch Plains, N.J.) to form pUC-SynCrtZ.

Example 9

Construction of Canthaxanthin Expression Plasmid pDCQ307

Figure 8:
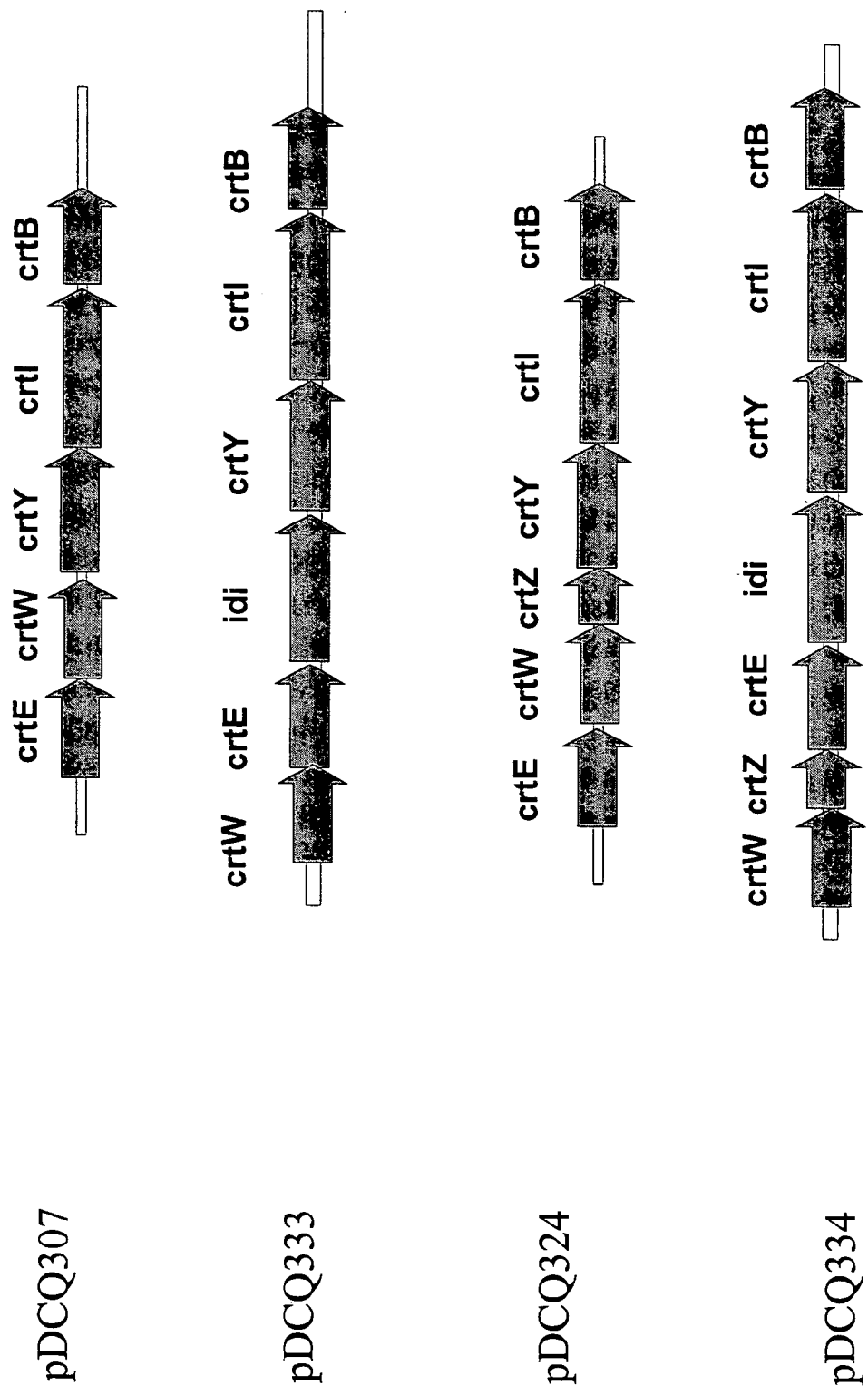
FIG. 8 shows representations of the carotenoid biosynthesis gene clusters cloned in plasmids pDCQ307, pDCQ333, pDCQ324, and pDCQ334.

The purpose of this Example was to prepare a canthaxanthin expression plasmid, referred to herein as pDCQ307. This canthaxanthin-producing plasmid was prepared by coupling the codon-optimized crtW gene (SEQ ID NO:7), described in Example 8, to a β-carotene synthesis gene cluster. The crtW gene was cloned downstream of crtE in the reorganized crtEYIB cluster from *P. stewartii* ATCC8199 to form the operon crtEWYIB (see FIG. 8).

*Pantoea stewartii* ATCC #8199 (WO 03/016503) contains the natural gene cluster crtEXYIBZ. The genes required for β-carotene synthesis (i.e., crtE and crtYIB) were joined together by PCR. Specifically, the crtE gene (SEQ ID NO:35) and crtYIB genes (SEQ ID NO:36) were each amplified using chromosomal DNA as template and the primers given in Table 6.

TABLE 6

Primers Used for Creation of the crtEYIB Reporter Construct

| Gene(s) | Forward Primer | Reverse Primer |
|---|---|---|
| crtE | pBHRcrt_1F:<br>5'-<u>GAATTC</u>GCCCTTGACGGT<br>CT-3'<br>(SEQ ID NO: 37) | pBHRcrt_1R:<br>5'-CGGTTGCATAATCCTGCC<br>CACT<u>CAATTG</u>TTAACTGACGG<br>CAGCGAGTTTT-3'<br>(SEQ ID NO: 38) |
| crtYIB | pBHRcrt_2F:<br>5'-AAAACTCGCTGCCGTCAG<br>TTAA<u>CAATTG</u>AGTGGGCAGGA<br>TTATGCAACCG-3'<br>(SEQ ID NO: 39) | pBHRcrt_2R:<br>5'-GGTACCTAGATCGGGCGC<br>TGCCAGA-3'<br>(SEQ ID NO: 40) |

*Note:
Underlined portions within each primer correspond to restriction sites for EcoRI, MfeI.

The PCR reactions were performed with Pfu DNA polymerase in buffer supplied by the manufacturer containing dNTPs (200 µM of each). Parameters for the thermocycling reactions were: 92° C. (5 min), followed by 30 cycles of: 95°

C. (30 sec), 55° C. (30 sec), and 72° C. (5 min). The reaction concluded with 1 cycle at 72° C. for 10 min. The two PCR products were gel purified and joined together by a subsequent PCR reaction using the primers pBHRcrt_1F (SEQ ID NO:37) and pBHRcrt_2R (SEQ ID NO:40). Parameters for the thermocycling reaction were: 95° C. (5 min), followed by 20 cycles of: 95° C. (30 sec), 55° C. (1 min) and 72° C. (8 min). A final elongation step at 72° C. for 10 min completed the reaction. The final 4511 bp PCR product was cloned into the pTrcHis2-Topo vector (Invitrogen, Carlsbad, Calif.) in the forward orientation, resulting in plasmid pDCQ300. The ~4.5 kB EcoRI fragment of pDCQ300 containing the crtEYIB gene cluster was ligated into the unique EcoRI site of vector pBHR1 (MoBiTec GmbH, Goettingen, Germany), to create construct pDCQ301. In pDCQ301, a unique MfeI site was engineered in the intergenic region of crtE and crtY.

The ~0.8 kB EcoRI fragment of pCRScript-Dup1, prepared as described in Example 8, containing the synthetic codon-optimized crtW gene was ligated to the unique MfeI site in pDCQ301. In the resulting construct pDCQ307, the crtEWYIB genes were under the control of the chloramphenicol resistant gene promoter of the vector.

Example 10

Evaluation of Canthaxanthin Production in Four *Methylomonas* sp. "White" Mutants The production of canthaxanthin was evaluated in all four of the *Methylomonas* sp. "white" mutant backgrounds, i.e., *Methylomonas* strains MWM1200 (Δcrt cluster promoter+ ΔcrtN3), MWM1300 (Δald(crtN1)+ΔcrtN3), MWM1100 (Δcrt cluster promoter), and MWM1000 (Δald(crtN1)). The canthaxanthin expression plasmid pDCQ307, prepared as described in Example 9, was transferred into each "white" mutant via conjugation using the same method described in Example 4. The resulting strains were designated as MCS001 (MWM1000 +pDCQ307), MCS002 (MWM1100+ pDCQ307), MCS003 (MWM1200+pDCQ307), and MCS004 (MWM1300+pDCQ307).

After purifying the strains away from the contaminating *E. coli* cells that were introduced during the mating, each strain was evaluated for the effect of canthaxanthin production on growth rate (data not shown). In addition, the canthaxanthin titers were determined for each strain, as described below.

THF/Methanol Extraction of $C_{40}$ Carotenoid

As described in Example 6 for the extraction of the $C_{30}$ carotenoid, a THF/methanol (1:1) solution was also employed for the extraction of the $C_{40}$ carotenoid from the *Methylomonas* sp. carotenoid-producing strains. The procedures were virtually identical to the $C_{30}$ carotenoid extraction method with the exception of the culture volumes used. Two 500-mL bottles containing ~60 mL of BTZ and 25% methane were grown until saturation (~24 hr) for each of the *Methylomonas* canthaxanthin-producing cultures (MCS001, MCS002, MCS003, and MCS004) to be analyzed. The cultures used in the growth rate experiments were used in this study. The cells were split into two fractions harvested via centrifugation. For one fraction, the cell pellets were dried at ~100° C. in an oven for ~24 hr and the dry cell mass was determined. The other fraction was used for $C_{40}$ carotenoid extractions. The cells were lysed using glass beads (0.5 mL/sample). Also added to each sample was 150 μL of the internal standard, ethyl-β-apo-8'-carotene (trans) (100 mg/L stock solution) and 5 mL of a THF/methanol (1:1) solution. This mixture was vortexed for ~2 min, followed by a 15 min centrifugation at 8,000 rpm. The supernatant was collected and the sample was vortexed again for ~2 min and centrifuged at 8,000 rpm for another 15 min. The supernatants were combined and were dried using nitrogen. The carotenoid samples were stored at −80° C. until analyzed using HPLC-photodiode array.

HPLC Diode Array Analysis of $C_{40}$ Carotenoid

The carotenoid samples were analyzed using HPLC diode array analysis, as described in Example 6. The measured canthaxanthin titers are given in Table 7. The highest titer was seen for MCS003 (~1400 ppm). This reflected an ~80% increase in titer over its parent strain MCS002 (~750 ppm). The only difference between these two strains is the deletion of crtN3 in MCS003. Thus, the deletion of crtN3 resulted in an increase in the production of the $C_{40}$ carotenoid that was greater than the increase that was observed in the production of the $C_{30}$ carotenoid, i.e., ~80% increase versus ~15% increase, respectively. However, the effect of the crtN3 deletion was not as pronounced in the MCS004 strain. The canthaxanthin titer of MCS004 (~1100 ppm) was only slightly higher (~11%) than its parent strain MCS001 (~1000 ppm). This result suggests that there are other contributing factors that influence the much higher titer that is seen in MCS003. One hypothesis is that it is the combination of the crtN2 deletion and the crtN3 deletion may have an additive effect on canthaxanthin production. Note that crtN2 is still present in MCS001 and MCS004.

TABLE 7

Canthaxanthin Titers for *Methylomonas* Mutants

| Strain | $C_{30}$ Carotenoid Genes Expressed | $C_{30}$ Carotenoid Genes Not Expressed | Canthaxanthin Titer (ppm) |
| --- | --- | --- | --- |
| MCS001 | crtN2, crtN3 | crtN1, ald | ~1000 |
| MCS002 | ald, crtN2, crtN3 | crtN1, | ~750 |
| MCS003 | ald, crtN2 | crtN1, crtN3 | ~1400 |
| MCS004 | crtN2 | crtN1, crtN3, ald | ~1100 |

Example 11

Construction of a Canthaxanthin-Producing *Methylomonas* sp. "White" Mutant

This Example describes the construction of another canthaxanthin-producing *Methylomonas* sp. 16a white mutant. The plasmid pDCQ333 was constructed by coupling the codon-optimized crtW gene to the β-carotene synthesis gene cluster crtEidiYIB from *Pantoea agglomerans* DC404 (U.S. Ser. No. 10/808,807). The crtW gene was cloned upstream of the crtE in the native cluster to form the operon crt-WEidiYIB (see FIG. 8). This operon was introduced into *Methylomonas* sp. 16a MWM1200 using tri-parental conjugation and the production of canthaxanthin by this transformed strain was analyzed using HPLC.

Codon-Optimized Ketolase Gene Coupled to β-Carotene Synthesis Genes from *P. agglomerans* DC404

*P. agglomerans* DC404 was an environmental isolate that contained the carotenoid synthesis gene cluster crtEidiYIBZ (SEQ ID NO:41), as described by Cheng et al. in copending U.S. Ser. No. 10/808,807. The soil from a residential vegetable garden in Wilmington, Del. was collected and resuspended in LB medium. A 10 µL loopful of resuspension was streaked onto LB plates and the plates were incubated at 30° C. Pigmented bacteria with diverse colony appearances were picked and streaked twice to homogeneity on LB plates and incubated at 30° C. From these colonies, one which formed pale yellow smooth translucent colonies was designated as "strain DC404".

*P. agglomerans* strain DC404 was grown in 25 mL of LB medium at 30° C. overnight with aeration. Bacterial cells were centrifuged at 4,000×g for 10 min. The cell pellet was gently resuspended in 5 mL of 50 mM Tris-10 mM EDTA (pH 8.0) and lysozyme was added to a final concentration of 2 mg/mL. The suspension was incubated at 37° C. for 1 hr. Sodium dodecyl sulfate was then added to a final concentration of 1% and proteinase K was added at 100 µg/mL. The suspension was incubated at 55° C. for 2 hr. The suspension became clear and the clear lysate was extracted twice with an equal volume of phenol:chloroform:isoamyl alcohol (25:24:1) and once with chloroform:isoamyl alcohol (24:1). After centrifuging at 4,000 rpm for 20 min, the aqueous phase was carefully removed and transferred to a new tube. Two volumes of ethanol were added and the DNA was gently spooled with a sealed glass Pasteur pipette. The DNA was dipped into a tube containing 70% ethanol. After air drying, the DNA was resuspended in 400 µL of TE (10 mM Tris-1 mM EDTA, pH 8.0) with RNaseA (100 µg/mL) and stored at 4° C. The concentration and purity of DNA was determined spectrophotometrically by $OD_{260}/OD_{280}$.

A cosmid library of DC404 was constructed using the pWEB cosmid cloning kit from Epicentre (Madison, Wis.) following the manufacturer's instructions. Genomic DNA was sheared by passing it through a syringe needle. The sheared DNA was end-repaired and size-selected on low-melting-point agarose by comparison with a 40 kB standard. DNA fragments approximately 40 kB in size were purified and ligated into the blunt-ended cloning-ready pWEB cosmid vector. The library was packaged using ultra-high efficiency MaxPlax Lambda Packaging Extracts, and plated on EPI100 *E. coli* cells. Two yellow colonies were identified from the cosmid library clones. The cosmid DNA from the two clones had similar restriction digestion patterns. This cosmid DNA, referred to herein as pWEB-404, contained the crtEidiYIBZ gene cluster, given as SEQ ID NO:41.

Primers pWEB404F: 5'-GAATTCACTAGTC-GAGACGCCGGGTACCMCCAT-3' (SEQ ID NO:42) and pWEB404R: 5'-GAATTCTAGCGCGGGCGCTGCCAGA-3' (SEQ ID NO:43) were used to amplify a fragment from DC404 containing the crtEidiYIB genes (SEQ ID NO:6) by PCR. Cosmid DNA pWEB-404 was used as the template with PfuTurbo™ polymerase (Stratagene, La Jolla, Calif.), and the following thermocycler conditions: 92° C. (5 min); 94° C. (1 min), 60° C. (1 min), 72° C. (9 min) for 25 cycles; and 72° C. (10 min). A single product of approximately 5.6 kB was observed following gel electrophoresis. Taq polymerase (Roche Appled Science, Indianapolis, Ind.) was used in a ten minute 72° C. reaction to add additional 3' adenosine nucleotides to the fragment for TOPO° cloning into pTrcHis2-TOPO (Invitrogen, Carlsbad, Calif.). Following transformation to *E. coli* TOP10 cells, several colonies appeared bright yellow in color, indicating that they were producing a carotenoid compound. The gene cluster was then subcloned into the broad host range vector pBHR1 (MoBiTec, LLC, Marco Island, Fla.), and electroporated into *E. coli* 10G cells (Lucigen, Middletown, Wis.). The transformants containing the resulting plasmid pDCQ330 were selected on LB medium containing 50 µg/mL kanamycin. In pDCQ330, a unique SpeI site was engineered upstream of crtE.

The ~0.8 kb EcoRI fragment of pCRScript-Dup1, prepared as described in Example 8, containing the synthetic, codon-optimized crtW gene was first blunt-ended and then ligated to pDCQ330, which was digested by SpeI and blunt-ended. In the resulting construct pDCQ333, the crtW gene was cloned upstream of the crtEidiYIB cluster and the crtWEidiYIB genes were under the control of the chloramphenicol resistant gene promoter of the vector.

Tri-Parental Conjugation of the Plasmid pDCQ333 into *Methylomonas* sp. 16a MWM1200

Plasmid pDCQ333 was transferred into *Methylomonas* 16a MWM1200 by tri-parental conjugal mating, which is described in Example 4. The *E. coli* helper strain containing pRK2013 and the *E. coli* 10G donor strain containing pDCQ333 were grown overnight in LB medium containing kanamycin (50 µg/mL), washed three times in LB, and resuspended in a volume of LB representing approximately a 60-fold concentration of the original culture volume.

The *Methylomonas* 16a MWM1200 strain, described in Example 7, was grown as the recipient using the general conditions described in Example 4. Briefly, *Methylomonas* 16a MWM1200 strain was grown in serum-stopped Wheaton bottles (Wheaton Scientific, Wheaton Ill.) using a gas/liquid ratio of at least 8:1 (i.e., 20 mL of liquid BTZ (nitrate) medium in 160 mL total volume) at 30° C. with constant shaking. The standard gas phase for cultivation contained 25% methane in air. The recipient cells were cultured under these conditions for 48 h in BTZ (nitrate) medium, washed three times in BTZ (nitrate), and resuspended in a volume of BTZ (nitrate) representing a 150-fold concentration of the original culture volume.

The donor, helper, and recipient cell pastes were then combined in ratios of 1:1:2, respectively, on the surface of BTZ (nitrate) agar plates containing 0.5% (w/v) yeast extract. Plates were maintained at 30° C. in 25% methane for 16-72 hr to allow conjugation to occur, after which the cell pastes were collected and resuspended in BTZ (nitrate). Dilutions were plated on BTZ (nitrate) agar containing kanamycin (50 µg/mL) and incubated at 30° C. in 25% methane for up to 1 week. Orange-red transconjugants were streaked onto BTZ (nitrate) agar containing kanamycin (50 µg/mL).

Analysis of Canthaxanthin Production

For analysis of carotenoid composition, transconjugants were cultured in 25 mL of BTZ (nitrate) medium containing kanamycin (50 µg/mL) and incubated at 30° C. in 25% methane as the sole carbon source for 3-4 days. The cells were harvested by centrifugation and frozen at −20° C. After thawing, the pellets were extracted with 10 mL of acetone, dried under nitrogen and redissolved in 1-2 mL of acetone. The extract was filtered using an Acrodisc CR25 mm syringe filter (Pall Corporation, Ann Arbor, Mich.). The extract was then concentrated in 0.1 mL of 10% acetone/90% acetonitrile for HPLC analysis using an Agilent Series 1100 LC/MSD SI (Agilent, Foster City, Calif.).

A cell extract sample (20 µL) was loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was:
0-2 min: 95% Buffer A and 5% Buffer B;
2-10 min: linear gradient from 95% Buffer A and 5% Buffer B to 60% Buffer A and 40% Buffer B;

10-12 min: linear gradient from 60% Buffer A and 40% Buffer B to 50% Buffer A and 50% Buffer B;
12-18 min: 50% Buffer A and 50% Buffer B; and,
18-20 min: 95% Buffer A: and 5% Buffer B.

Buffer A was 95% acetonitrile and 5% dH$_2$O; Buffer B was 100% tetrahydrofuran.

The resulting chromatogram showed that in *Methylomonas* MWM1200 containing pDCQ333, the major carotenoid produced was canthaxanthin, which eluted at 8.2 min. The echinenone intermediate was also present at a low level.

Example 12

Construction of Astaxanthin-Producing *Methylomonas* sp. "White" Mutants

This Example describes the construction of two astaxanthin-producing *Methylomonas* sp. 16a white mutants. Two plasmids were constructed by coupling the codon-optimized crtW and crtZ genes, described in Example 8, to two different β-carotene synthesis gene clusters. In the first construct pDCQ324, the crtWZ genes were cloned downstream of crtE in the reorganized crtEYIB cluster from *P. stewartii* ATCC8199 to form the operon crtEWZYIB (see FIG. 8). In the second construct pDCQ334, the crtWZ genes were cloned upstream of crtE in the native crtEidiYIB cluster from *P. agglomerans* DC404 to form the operon crtWZEidiYIB (see FIG. 8). These operons were introduced into *Methylomonas* sp. 16a MWM1200 using tri-parental conjugation and the production of C$_{40}$ carotenoids by the two resulting transformed strains were analyzed using HPLC.

Codon-Optimized Ketolase and Hydroxylase Genes Coupled to β-Carotene Synthesis Genes from *P. stewartii* ATCC8199

In order to create convenient restriction sites for incorporating the codon-optimized hydroxylase gene crtZ (SEQ ID NO:8) into the cluster, unique XbaI and Bg/II sites were introduced downstream of the crtW gene. The codon-optimized crtW gene was PCR amplified using pDCQ307 DNA as template with primers crtW_F_Agro(Syn) 5'-GC CAATTGAAGGAGGAATAAACCATG-3' (SEQ ID NO:44) and crtW_R_Agro(Syn) 5'-GC GAATTCAGATCTTGC TCTAGATCACGCGGTGTCGCCTTTG-3' (SEQ ID NO:45). The underlined portions of these primer sequences are restriction sites for EcoRI, MfeI Bg/II, or XbaI. The ~0.8 kB PCR product containing the crtW gene was digested with MfeI/EcoRI and ligated into the unique MfeI site in pDCQ301. The ~0.5 kB XbaI/Bg/II fragment of pUC-synCrtZ, described in Example 8, containing the codon-optimized crtZ gene was then cloned to the XbaI/Bg/II sites downstream of crtW In the resulting construct pDCQ324, the crtEWZYIB genes were organized in an operon and were under the control of the chloramphenicol resistant gene promoter of the vector.

Codon-Optimized Ketolase and Hydroxylase Genes Coupled to β-Carotene Synthesis Genes from *P. agglomerans* DC404

The codon-optimized crtWZ genes were PCR amplified using pDCQ324 DNA as template, with primers crtWZ_F (syn agro): 5'-ACTAGTAAGGAGGAATAAACCATGAGCGCC-3' (SEQ ID NO:46) and crtWZ_R(syn agro): 5'-GCTAGCTGTACATTAGGTGCGTTCTTGGGCTTC-3' (SEQ ID NO:47). The underlined portions of these primer sequences were engineered restriction enzyme sites for SpeI and NheI. The ~1.3 kb PCR product was gel-purified and cloned into the pTrcHis2-topo vector. The~1.3 kb SpeI/NheI fragment containing crtWZ genes was then subcloned into the SpeI site of pDCQ330. In the resulting plasmid pDCQ334, the crtWZEidiYIB genes were organized in an operon and were under the control of the chloramphenicol resistant gene promoter of the vector.

Tri-Parental Conjugation of the Plasmids pDCQ324 or pDCQ334 into *Methylomonas* sp. 16a MWM1200

Plasmid pDCQ324 or pDCQ334 was transferred into *Methylomonas* 16a MWM1200 using tri-parental conjugation, as described in Example 11. The transconjugants were grown and analyzed as described in Example 11. The HPLC results showed that in *Methylomonas* MWM1200 containing pDCQ324 or pDCQ334, the major carotenoid produced was astaxanthin, which eluted at about 5.5 min. The intermediates such as adonixanthin, adonirubin and canthaxanthin were also present. Identification of astaxanthin and canthaxanthin were based on comparison of elution time, absorption spectrum and the molecular weight with those of the authentic standards obtained from CaroteNature (Lupsingen, Switzerland). Identification of adonixanthin and adonirubin were based on the comparison of the absorption spectrum and the molecular weight with those reported in the literature.

What is claimed is:

1. A high growth methanotrophic bacterial strain which:
   a) grows on a C1 carbon substrate selected from the group consisting of methanol and methane;
   b) comprises a functional Embden-Meyerhof carbon pathway, said pathway comprising a gene encoding a pyrophosphate dependent phosphofructokinase enzyme;
   c) possesses a disruption such that at least one endogenous gene selected from the group consisting of carotenoid gene N1 (crtN1), aldehyde dehydrogenase gene (ald), carotenoid gene N2 (crtN2), and carotenoid gene N3 (crtN3) is down-regulated; and
   d) comprises a 16s rRNA sequence as set forth in SEQ ID NO:1.

2. The bacterial strain of claim 1 comprising at least one gene encoding an enzyme of the $C_{40}$ carotenoid biosynthesis pathway selected from the group consisting of: carotenoid gene E (crtE), carotenoid gene X (crtX), carotenoid gene Y (crtY), carotenoid gene I (crtI), carotenoid gene B (crtB), carotenoid gene R (crtR), carotenoid gene Z (crtZ), carotenoid gene W (crtW), carotenoid gene O (crtO), carotenoid gene A (crtA), carotenoid gene C (crtC), carotenoid gene D (crtD), carotenoid gene F (crtF), and carotenoid gene U (crtU).

3. The bacterial strain of claim 1 wherein the strain is a *Methylomonas* sp.

4. The *Methylomonas* sp. strain of claim 3 further comprising:
   (a) a crtE-idi-crtY-crtI-crtB gene cluster having the sequence as set forth in SEQ ID NO:6; and
   (b) a codon-optimized β-carotene ketolase gene having the sequence as set forth in SEQ ID NO:7.

5. The *Methylomonas* sp. strain of claim 3 further comprising:
   (a) a crtE-idi-crtY-crtI-crtB gene cluster having the sequence as set forth in SEQ ID NO:6;
   (b) a codon-optimized β-carotene ketolase gene having the sequence as set forth in SEQ ID NO:7; and
   (c) a codon-optimized β-carotene hydroxylase gene having the sequence as set forth in SEQ ID NO:8.

6. The *Methylomonas* sp. strain of claim 3 wherein the down regulated genes have the nucleic acid sequences (SEQ ID NO:2), (SEQ ID NO:3), (SEQ ID NO:4), (SEQ ID NO:5) corresponding to the genes crtN1, ald, crtN2, and crtN3 respectively.

7. The bacterial strain of claim 1 which possesses a disruption such that endogenous crtN1 is down-regulated.

* * * * *

SEQUENCE LISTING

```
<160> NUMBER OF SEQ ID NOS: 53

<210> SEQ ID NO 1
<211> LENGTH: 1429
<212> TYPE: DNA
<213> ORGANISM: Methylomonas sp. 16A

<400> SEQUENCE: 1
cggtatgctt aacacatgca agtcgaacgc tgaagggtgc ttgcacctgg atgagtggcg      60
gacgggtgag taatgcatag gaatctgcct attagtgggg gataacgtgg ggaaactcac     120
gctaataccg catacgctct acggaggaaa gccgggacc ttcgggcctg gcgctaatag     180
atgagcctat gtcggattag ctagttggtg gggtaaaggc ctaccaaggc gacgatccgt     240
```

-continued

```
agctggtctg agaggatgat cagccacact gggactgaga cacggcccag actcctacgg    300
gaggcagcag tggggaatat tggacaatgg gcgcaagcct gatccagcaa taccgcgtgt    360
gtgaagaagg cctgagggtt gtaaagcact ttcaatggga aggaacacct atcggttaat    420
acccggtaga ctgacattac ccatacaaga agcaccggct aactccgtgc cagcagccgc    480
ggtaatacgg agggtgcaag cgttaatcgg aattactggg cgtaaagcgt gcgtaggcgg    540
tttttttaagt cagatgtgaa agccctgggc ttaacctggg aactgcattt gatactgggg    600
aactagagtt gagtagagga gagtggaatt tcaggtgtag cggtgaaatg cgtagagatc    660
tgaaggaaca ccagtggcga aggcggctct ctggactcaa actgacgctg aggtacgaaa    720
gcgtgggtag caaacaggat tagatacccct ggtagtccac gccgtaaacg atgtcaacta    780
accgttgggt tcttaaagaa cttagtggtg gagctaacgt attaagttga ccgcctgggg    840
agtacggccg caaggctaaa actcaaatga attgacgggg gcccgcacaa gcggtggagc    900
atgtggttta attcgatgca acgcgaagaa ccttacctac ccttgacatc ctcggaactt    960
gtcagagatg acttggtgcc ttcgggaacc gagagacagg tgctgcatgg ctgtcgtcag   1020
ctcgtgtcgt gagatgttgg gttaagtccc gtaacgagcg caacccttat ccttagttgc   1080
cagcgcgtca tggcgggaac tctagggaga ctgccggtga taaaccggag gaaggtgggg   1140
acgacgtcaa gtcatcatgg cccttatggg tagggctaca cacgtgctac aatggtcggt   1200
acagagggtt gcgaactcgc gagagccagc caatcccaaa aagccgatcc tagtccggat   1260
tgcagtctgc aactcgactt gcatgaagtc ggaatcgcta gtaatcgcgg atcagaatgc   1320
cgcggtgaat acgttcccgg gccttgtaca caccgcccgt cacaccatgg gagtgggttg   1380
caaaagaagt aggtagttta accttcggga gggcgcttac cactttgtg              1429
```

<210> SEQ ID NO 2
<211> LENGTH: 1536
<212> TYPE: DNA
<213> ORGANISM: Methylomonas sp. 16A

<400> SEQUENCE: 2

```
atggccaaca ccaaacacat catcatcgtc ggcgcgggtc ccggcggact tgcgccggc     60
atgttgctga ccagcgcgg cttcaaggta tcgattttcg acaaacatgc agaaatcggc    120
ggccgcaacc gcccgatcaa catgaacggc tttaccttcg ataccggtcc gacattcttg    180
ttgatgaaag gcgtgctgga cgaaatgttc gaactgtgcg agcgccgtag cgaggattat    240
ctggaattcc tgccgctaag cccgatgtac cgcctgctgt acgacgaccg cgacatcttc    300
gtctattccg accgcgagaa catgcgcgcc gaattgcaac gggtattcga cgaaggcacg    360
gacggctacg aacagttcat ggaacaggaa cgcaaacgct caacgcgct gtatccctgc    420
atcacccgcg attattccag cctgaaatcc tttttgtcgc tggacttgat caaggccctg    480
ccgtggctgg cttttccgaa aagcgtgttc aataatctcg gccagtattt caaccaggaa    540
aaaatgcgcc tggcctttg ctttcagtcc aagtatctgg gcatgtcgcc gtgggaatgc    600
ccggcactgt ttacgatgct gccctatctg gagcacgaat acggcattta tcacgtcaaa    660
ggcggcctga accgcatcgc ggcggcgatg gcgcaagtga tcgcgaaaa cggcggcgaa    720
attcacttga acagcgaaat cgagtcgctg atcatcgaaa acggcgctgc caagggcgtc    780
aaattacaac atggcgcgga gctgcgcggc gacgaagtca tcatcaacgc ggattttgcc    840
cacgcgatga cgcatctggt caaaccgggc gtcttgaaaa aatacacccc ggaaaacctg    900
```

| | |
|---|---|
| aagcagcgcg agtattcctg ttcgaccttc atgctgtatc tgggtttgga caagatttac | 960 |
| gatctgccgc accataccat cgtgtttgcc aaggattaca ccaccaatat ccgcaacatt | 1020 |
| ttcgacaaca aaaccctgac ggacgatttt tcgttttacg tgcaaaacgc cagcgccagc | 1080 |
| gacgacagcc tagcgccagc cggcaaatcg cgctgtacg tgctggtgcc gatgcccaac | 1140 |
| aacgacagcg gcctggactg gcaggcgcat tgccaaaacg tgcgcgaaca ggtgttggac | 1200 |
| acgctgggcg cgcgactggg attgagcgac atcagagccc atatcgaatg cgaaaaaatc | 1260 |
| atcacgccgc aaacctggga aacggacgaa cacgtttaca agggcgccac tttcagtttg | 1320 |
| tcgcacaagt tcagccaaat gctgtactgg cggccgcaca accgtttcga ggaactggcc | 1380 |
| aattgctatc tggtcggcgg cggcacgcat cccggtagcg gtttgccgac catctacgaa | 1440 |
| tcggcgcgga tttcggccaa gctgatttcc cagaaacatc gggtgaggtt caaggacata | 1500 |
| gcacacagcg cctggctgaa aaagccaaa gcctga | 1536 |

<210> SEQ ID NO 3
<211> LENGTH: 1593
<212> TYPE: DNA
<213> ORGANISM: Methylomonas sp. 16A

<400> SEQUENCE: 3

| | |
|---|---|
| atgacgacga tagcagccgt ctccccactg gatggccgct tgctgggaca ttttccagtc | 60 |
| agcaagccgg cgctcattca gcaacagctg acaaaatccc gccgcgccgc cctgctttgg | 120 |
| cgcgagctgc cggtcacgga acgggtcaaa cgcctgtcgc ccttgaaaaa acagctgctg | 180 |
| gataacctgg acagactctg cgaaaccatc cgcctcagca ccggcaaggt tcgcaccgag | 240 |
| gccttgctgg gggaaattta tccggtgctg gatttactgg cgtattacca aaagcgggcg | 300 |
| ccgcggattc tacgcacgcg cgccgtgtcc acctcgccgt tcgcgttttcc ggccgccacc | 360 |
| gcccgcatcg aacgccgccc ttacggcgtg gtcgcggtga tctcgccatg gaattacccg | 420 |
| tttcacctga gcgtcgcccc gctgctgacc gctttgctgg ccggcaatgc ggtaatcctg | 480 |
| aaaccctccg aactctgctt gccggtcggt cagttgatcg tcgatttgtt cgccacgctg | 540 |
| gatttgccgg acgggttggt gcaatgggtc atcggcgacg gccaaaccgg cgcggaactg | 600 |
| atagacgccc gccccgatct ggtgtttttc accggcggcc tgcagaccgg tcgggcggtc | 660 |
| atgcaacgcg ccgcccggca tccgattccg gtcatgctgg agttgggcgg taaagacacc | 720 |
| atgctggtgc tggccgacgc cgacctcaag cgcgccagcg ctgccgcgct gtacggcgcg | 780 |
| tttttgcaata gcggccaagt ctgcgtctcg gtcgaacgtc tgtacgtgca acaagcctgt | 840 |
| tttgcggaat tcctggccat gctgctgaag ggcctgtcca agctcaaggt cggccatgac | 900 |
| ccgcacggcg atgtgggagt gatgacgtcc gcccggcaaa tcgacatcgt ccaggcccat | 960 |
| tacgaggacg ccatcgccca gggcgccaag gcctccggcc cgctgctgcg cgacggcaat | 1020 |
| gtcgtgcaac ccgtggtgct ttgggacgtg caccacggca tgaaggtcat gcgcgaggaa | 1080 |
| accttcggtc cgttgctgcc ggtcatgccg ttcagcgacg aagccgaggc catcaagctc | 1140 |
| gccaacgaca gcgatctggg tctaaacgcc agcatctgga gccaggatat aatcaaggcc | 1200 |
| gagcgccttg ctggacaact agatgtcggc aactgggcga tcaacgacgt attgaaaaac | 1260 |
| gtgggccatt ccgcctgcc cttcggcggc gtcaagcaaa gcgggtttgg ccgttatcac | 1320 |
| ggcgccgaag gcttgctgaa cttcagctac ccggtatcgg gcctgaccaa tcgcagccgc | 1380 |
| ttgcccaaag aacccaactg gttcccttac agcgcatcag gctatgaaaa tttcaagggt | 1440 |
| ttcctcgatt ttatctacgg cgaagactcg atgctgcagc gcggtcgccg caatcagcaa | 1500 |

```
gcgctgcaag ccttccgcga gttttccatt ttcgattgga cacaacgctg gcaaaacctg    1560
aaactgctgt tttcttggac acgggatgac taa                                 1593

<210> SEQ ID NO 4
<211> LENGTH: 1494
<212> TYPE: DNA
<213> ORGANISM: Methylomonas sp. 16A

<400> SEQUENCE: 4
atgaactcaa atgacaacca acgcgtgatc gtgatcggcg ccggcctcgg cggcctgtcc      60
gccgctattt cgctggccac ggccggcttt tccgtgcaac tcatcgaaaa aaacgacaag    120
gtcggcggca agctcaacat catgaccaaa gacggcttta ccttcgatct ggggccgtcc    180
attttgacga tgccgcacat ctttgaggcc ttgttcacag gggccggcaa aaacatggcc    240
gattacgtgc aaatccagaa agtcgaaccg cactggcgca atttcttcga ggacggtagc    300
gtgatcgact tgtgcgaaga cgccgaaacc cagcgccgcg agctggataa acttggcccc    360
ggcacttacg cgcaattcca gcgctttctg gactattcga aaaacctctg cacggaaacc    420
gaagccggtt acttcgccaa gggcctggac ggcttttggg atttactcaa gttttacggc    480
ccgctccgca gcctgctgag tttcgacgtc ttccgcagca tggaccaggg cgtgcgccgc    540
tttatttccg atcccaagtt ggtcgaaatc ctgaattact tcatcaaata cgtcggctcc    600
tcgccttacg atgcgcccgc cttgatgaac ctgctgcctt acattcaata tcattacggc    660
ctgtggtacg tgaaaggcgg catgtatggc atggcgcagg ccatggaaaa actggccgtg    720
gaattgggcg tcgagattcg tttagatgcc gaggtgtcgg aaatccaaaa acaggacggc    780
agagcctgcc ccgtaaagtt ggcgaacggc gacgtgctgc cggccgacat cgtggtgtcg    840
aacatggaag tgattccggc gatggaaaaa ctgctgcgca gcccggccag cgaactgaaa    900
aaaatgcagc gcttcgagcc tagctgttcc ggcctggtgc tgcacttggg cgtggacagg    960
ctgtatccgc aactggcgca ccacaatttc ttttattccg atcatccgcg cgaacatttc   1020
gatgcggtat tcaaaagcca tcgcctgtcg acgatccga ccatttatct ggtcgcgccg    1080
tgcaagaccg accccgccca ggcgccggcc ggctgcgaga tcatcaaaat cctgccccat    1140
atcccgcacc tcgaccccga caaactgctg accgccgagg attattcagc cttgcgcgag   1200
cgggtgctgg tcaaactcga acgcatgggc ctgacggatt tacgccaaca catcgtgacc    1260
gaagaatact ggacgccgct ggatattcag gccaaatatt attcaaacca gggctcgatt    1320
tacggcgtgg tcgccgaccg cttcaaaaac ctgggtttca aggcacctca acgcagcagc    1380
gaattatcca atctgtatt cgtcggcggc agcgtcaatc ccggcggcgg catgccgatg    1440
gtgacgctgt ccgggcaatt ggtgagggac aagattgtgg cggatttgca ataa         1494

<210> SEQ ID NO 5
<211> LENGTH: 1542
<212> TYPE: DNA
<213> ORGANISM: Methylomonas sp. 16A

<400> SEQUENCE: 5
atgcgcggca ttcatccaga atccaaacac gaacaatacg acgtgatcgt cataggcgcc       60
ggtatcggcg gcttgagcac ggccgcgtta ttggcgaaag ccggaaaagc cgtgttgtta     120
gtcgaaaggc atgaccgccc cggcggttat gctcacggtt ccggcggcg caattaccat     180 ttcgattcgg gggtacatct ggtcagcggc tgcggtgccg acggctatga aaacggcagc     240
```

```
acgatttacc ggatttgccg ggccgtgggc atagacaccg aggatgtttt ccttccgatc      300
ccgtcttacg cccgcgcggt gtttccgggg ttcgaactga gcctgcatgc cggcgaagag      360
gtgttcgtcg gtgagttatg cgcgcatttc ccaaacgaaa aggacaatct gctccgcttg      420
attcggctct gcaaaaccct ggcggaagaa gccatgctgg cggaagaaat tctggaacag      480
agcaaaatca ctcgcgtacc acccacgcga cgctggcca atttgtttcg ttaccgccgc      540
gccaccttgg cggaagcact ggatgaattt ttgctcgacc cacatcttaa aagtgcctgc      600
gccgcgctat ggccttattt gggcctaccg ccttcgcaac tgtctttctt atattgggcc      660
agcatgatgg cgggctacac ctacgaaggt gcgtattatt gccgcggcag ttttcaaacc      720
tatgccaaca gactggcgca agcgatcgaa aagcgcggcg cgaggtgtt attgaacgcc       780 agcgtgcggc ggatttgcgt ggaaaacggc ggcatcagcg gcatcatgct ggaaaatggt      840
caactaatac gcgcaaagac cgtagtctcg aatgtcgccg cccagcaaac cgccgaatta      900
ctgatcggtc gcgagcattg gccggctggc tattgcgaca gctgaaaaa gttggcgccg       960 tcgctgtcga ttttcgccag ctacatcgca accgatttgg ccatcgacac ggccgttcat     1020
agccacgagt cgttttttta ccaaaccttc gatcacgaag ccgggtttgc atccacgcac     1080
aaggggcagc ccaattggtt ttcggccacc ctgtcgacgt tgagcgatgc ctcgctggca     1140
ccggccggtc aacacaccct gatgctgacc accttatgcc cgtttgacat agggcaaagc     1200
tggcgacagg ccaaactgga ctttgagcaa cgcttattgg cgcaagccga caacatttt     1260 ccaggcctga agaccatttt gttgctgata gaatccggct cgccgcgcac gctggaacgc     1320
tacaccctca accaccaagg cgcggcctac ggctttgccc ctaccccga tcaaatcggc     1380 ccaaaccgtc cggacgttcg cggagccttg ccgggcttgt tccacaccgg ccactggacg     1440
cgtccgggcg gcggcgtcgc cggcgtcagt atctcggctc aactggcggc acaagccatt     1500
ttgaacctgc ccatacaagc cgatttctgg aacagcctgg at                        1542
```

<210> SEQ ID NO 6
<211> LENGTH: 5632
<212> TYPE: DNA
<213> ORGANISM: Pantoea agglomerans

<400> SEQUENCE: 6

```
catgaccggc ggcgcggcgc gcgccagaga cattaaccgt catctggccc aggcggcgca       60
aacccttggg ctggcgatgg gcgtcggttc ccagcgcgtg gcgctggagg acggcgcgca      120
gcacgggctg gatgcccagc tacgccatat cgccccggac gtgccgctgc tggctaacct      180
tggcgcggcg cagatccgcg gtgcgcaggg gctggactac gcccggcgcg cggtggacat      240
gatcgacgcc gacgcgttaa ttgtgcatct gaacccgctg caggaggcgc tccagggcgg      300
cggcgatcgc gactggcgcg gcatcctcaa cgccattgcg cagctggtgc gcgacctgcc      360
ggtaccggtg gtggttaaag aggtgggcgc cgggatctcc ccggacgttg cctgccgact      420
ggcggacgtc ggcgtggcga tgatcgacat tgccggcgcg ggcggaacca gctgggcggc      480
ggtggaagct gaacgcgccc gaccccga ggcgcgaaat gtggcgatgg cctttgccga       540
ctggggcatt cctactgccg atgcgctgcg tcgcgtccat cttgcgctgc ctgatatccc      600
gcttatcgcc tccggcggca tcgccaacgg cattgacgca gcaaagcca tcgcgctggg      660 tgcagatctg gtgggccagg ccgcggcggt gctggcgcat gccaacgccc cggcgacgc      720 ggcaattgcc catttccgca ccctgattac gcagctgcgg atcgcctgtt tctgtaccgg      780
cagtgcaaac ctgcaggcgt tgcgacacgc cacgctgctt ccggtcaacg gcggcgcatc     840
```

```
cctgtgacgc agtacggtgc cttataccgg ggagcggtat gaaaaaatgg gatctgattc      900
tggtcggcgc ggggctggcc aacgggctta tcgcctggcg actaaagcag cgtcatccga      960
cgcttgctgt attaatgctg gagtgcggcg acgcgcccgg cggaaaccac acctggtcct     1020
ttcaccaaca cgatatcacg ccagcccagc acgcctggct ggcgccgctg gtggcccatc     1080
gctgggacgg gtacgacgtc cactttccga acgtgtcgcg caccctgcat gacggctacc     1140
tgaccatcac ctccacgcgt tttgcccaag cgatgcgcgg gctgatgaaa gagaatttgc     1200
tgacaaacgt gaccgtgtca cgggtgagcg ggcaggaagt aaccctcagc gacggacgac     1260
gctttaccgc cggggcggtg attgatggcc gcggctatca gccctcgccg cacctcagca     1320
ttggctatca ggcgttcatc ggccaggagt ggcaactgac cgcgccccac gggttaacgc     1380
gcccgatcct gatggatgcc cgcgtcgccc agggcaacgg ctaccgcttt gtctataccc     1440
tgccgctcag cgccgacacc ctgcttatcg aagacacgca ctacattgac ggcccgacgc     1500
tcgacgccga ttcagcccgc gcgcggattg ccgattacgc ccgccagcag ggctggcagc     1560
ttgcgcggct ggtgcgtgag gaacaggggg cgctgccgat caccctgtcc ggcgatccgg     1620
ccgccttctg gcaccagttc catcatcagc cggtcagcgg cctgcgcgcc ggtctgttcc     1680
atgccaccac cggctattcg ctgccgctgg cggttcggct ggcggaccgc attgccaacg     1740
cgccgggact gcatcagggc gcgctctatc agctgatcgc cgatttcgcg gcgcgccact     1800
ggcagacaca acgcttttc cgcctgctta accgcatgct tttcctggcc ggcacacccg      1860
accagcgctg gcgcgtgatg cagcggtttt accagcttga cgagcagctg atcgcccgtt     1920
tttatgccgg ccagcttcgc tccgccgacc gcgcgcgcct gctgcttggc aaaccgccgg     1980
tgccgattgt cggggcgatc aaagccctgc tccacactca ttcttctctg cgagcccatc     2040
ataaatgaaa caaaccattg taattggcgc cgggttcggc ggactggcgc tggcgattcg     2100
cctccaggcg gcgggcattc ctaccacgct gctggagagc cgcgacaaac ccggcggccg     2160
cgcctatgtc tacgaagatc gcggctttac ctttgatgcg ggtcccaccg tcatcaccga     2220
tccctccgcc attgaggagc tgttcaccct cgccggaaaa cggctgaagg actacgttga     2280
gctgatgccg gtgacgccgt tctatcgcct gtgctgggaa gacggcaagg ttttcgacta     2340
cgccaacgat caggcggcgc ttgagtcgca gatcgccgcg tttaacccga acgacgtggc     2400
gggctatcac cgcttcctcg actactcccg ggcggtgttt gccgaaggct atctgaagct     2460
cggcgcggtg ccgtttctct cgtttcgcga catgctgcgc gccggtcctc aactggcgcg     2520
gctgcaggca tggcgcagcg tgtacgacaa agtgtcggcc tacgtggaag acgagcacct     2580
gcggcaggca ttttcgtttc actcgctgct ggtgggcggc aacccgttct ccacgtcttc     2640
tatttacacc ctgatccacg ccctggagcg ggaatggggc gtctggttcc cgcgcggcgg     2700
caccggtgcg ctggtcagg gcatggtgaa gctgtttcag gatcttggcg gcaccctcac      2760
ccttaacgct caggttgagc ggctggagac ggtggacaat caggtgaagg ccgtgcatct     2820
ggttaacggg cagcggctgg aggctgcggc ggtggcctcg aacgcggacg tggtaaatac     2880
ctatgcccga ctgctcggcc atcacccgca cggcgccgct acggccaaaa agctgaaacg     2940
caagcgcatg agcaactcgc tgttcgtgct ctattttggc ctggatcacc atcacaccca     3000
gctggcgcac cataccgtct gctttggccc gcgttataaa gcgctaatcg atgaaatttt     3060
cagcgccgac accctgtcgg aagatttttc gctctatctg catgcgccct gcgtaaccga     3120
cccgtcgctg gccccgccgg ggtgcggcag ctactatgtg ctcgcgccgg tgccgcacct     3180
```

```
cggtaacgcc ccgctcgact ggagcgtgga agggccgcgt ctgcgggatc gcattttga    3240 ttatctcgaa gcgcgctata tgccggggct gcgctcccag ctggtgacgc accgcatgtt   3300
cacgccggaa gattttcgcg atacgctcga tgcctggcag gggtcagcgt tttcactgga   3360
gccgatcctc acccagagcg cctggttccg gccgcacaac cgcgacagcg tggttgataa   3420
cctctacctg gtcggcgccg gaacgcatcc cggcgctggc gtgccgggcg tgatcggatc   3480
cgccaaggca acggcccagt taatgttaaa ggatttagcg taatgtccca gccgcttctc   3540
gaacacgcca cgcgccaccat gaccgccggt tctaaaagtt tcgccaccgc ctcaaagctg   3600
tttgacaaac gcaccggcg cagcgcgctg atgctctata cctggtgccg ctactgcgac    3660
gatgttatcg acggacaggt ggtgggtttt gctgccccga ccgagcagag cgacacgccc   3720
gaggcgcgcc tgcaacggct gcgtaagatg acgcgccgcg cctacgacgg ggaaaccatg   3780
caagagccgc cgttcgccgc ctttcaggag gttgccctcg cccatgccat tccgcctact   3840
caggccttcg accacctgga aggctatgcg atggacgtgc gcaacgagcg ctattacagc   3900
ctcgatgata cgctccgcta ctgttatcac gtggcgggcg tggtcggcct gatgatggcc   3960
agggtgatgg gagtgcggga cgaagccacg ctggatcgcg cctgcgatct gggcattgcc   4020
tttcagctca ccaatatcgc cagggatatc gttgacgatg cgcaggtggg acgctgctac   4080
ctgccgcagc agtggctggc ggaagtcgga ctcaatgaac agacctgcac cgtgcgggcc   4140
aaccgtccgg cgctggcgcg tctggcagcg cggctggtga ccgaggctga gccctattat   4200
cagtcagcgc ttgccgggct gggggatctg cccctgcgct ccgcctgggc gattgccacc   4260
gcgcacgggg tgtatcgtga gatcggggtg aaggtgctga tggcgggtga aaaagcatgg   4320
gatacccgcc agggcacgac gcgcgcggag aagctggcgc tggttatttc cggcgcgaag   4380
caggcgatgg cttcccggaa ggcgagctgg ccgccgcgcg atccgcacct ctggcagcgc   4440
ccgcgctaga attcgaattc actagtcgag acgccgggta ccaaccatga caagacccctt   4500 tgaaacacat cccggtcacg acggggaact gcatgagctg cacgctgccc tgcaacgtcg   4560
cctggatgaa ctgctgcccg ttggcgatga gcgggatcgg gtcagcagcg caatgcgcga   4620
aggcgtactg caccggggga aacgcattcg cccgctgctc ctgatcctcg ccgcccgcga   4680
cctcggctgc gatcgcgacc accccggcct gctggatatg gcctgtgcgg tggaaatggt   4740
gcacgcctcg tcgctgatcc tcgacgatat tccctgcatg gataacgcgg cgctccggcg   4800
cggtcgccct accattcatc gccagtatgg tgaagacgtg gcaattctcg ctgcggtagc   4860
gttgctcagc agcgcctttg gcgtgatggt cgcggcgcag ggattgtctc ccgagtgccg   4920
cagccaggcg gtggcggagc tgtcgatggc ggtcggtacc cagggtctgg tgcagggtca   4980
gtataaggat ctgcgtgaag caccgccccc gcgcagcgcc gaggagatcg ccaccaccaa   5040
cgaactgaaa accagcgtgc tgtttggtgc cacgctgcaa atcgcggccc tggcggcagg   5100
cgcctcgccg gcggcgcgcc agaaaatgcg ctgctttgcg caggatttag gccaggcgtt   5160
ccagctgctg gacgatctgg cggacggcca tgccgggacc ggcaaagaca tcaataagga   5220
cgcgggtaag tccacgctgg tggcgatgct cggcagcgac gcggtgcgcg agcggctcga   5280
cacccatctg cgccgcgcag acgcccattt ttcacgcgcc tgcggaaaaa accaggccac   5340
gcgacgcttt atgcacgcct ggttttcaaa acagctggcc gcgtttagct gagcaacgga   5400 tacacccccgg taatatttgt ggagatcaca tgaaggacgc gcatctggtt cagcgtaaaa   5460
atgaccacct ggtatcgtg ctgcaccctg accgggcgat gagtaccatt cgcaccggat   5520
ttgacgcctg gcgttttgaa cactgcgccc tcccggagct ggatctcgac ggtatcgatc   5580
```

-continued tctccaccac cctgttttcc cgcccgctga agcccccggt gctgatcagc tc        5632

<210> SEQ ID NO 7
<211> LENGTH: 756
<212> TYPE: DNA
<213> ORGANISM: Artificial Sequence
<220> FEATURE:
<223> OTHER INFORMATION: Codon-optimized crtW gene from Agrobacterium
      aurantiacum

<400> SEQUENCE: 7
caattgaagg aggaataaac catgagcgcc catgccctgc cgaaagccga cctgaccgcg    60
accagcctga tcgtcagcgg tggcatcatc gcggcctggc tggcgctgca tgtccatgcc   120
ctgtggttcc tggacgccgc cgcccatccg atcctggcca tcgccaactt cctgggcctg   180
acctggctga gcgtcggcct gttcatcatc gcgcatgacg ccatgcatgg cagcgtggtc   240
ccgggtcgtc cgcgtgccaa cgccgccatg ggccaactgg tcctgtggtt gtatgccggc   300
ttcagctggc gcaagatgat cgtcaaacat atggcccatc atcgccacgc gggcaccgac   360
gacgatccgg acttcgacca tggtggcccg gtccgctggt atgcgcgctt catcggcacc   420
tatttcggct ggcgtgaagg cctgttgctg ccggtcatcg tcaccgtcta tgcgctgatc   480
ctgggcgacc gctggatgta tgtcgtcttc tggccgctgc cgagcatcct ggcgagcatc   540
caactgttcg tcttcggtac ctggctgccg atcgcccgg ccatgacgc ctttccggac   600 cgccataacg cccgcagcag ccgcatcagc gacccggtca gcctgctgac ctgcttccat   660 tcggcggct atcatcatga acatcatctg catccgaccg tcccgtggtg gcgcctgccg   720
agcacccgca ccaaaggcga caccgcgtga caattg                            756

<210> SEQ ID NO 8
<211> LENGTH: 533
<212> TYPE: DNA
<213> ORGANISM: Artificial Sequence
<220> FEATURE:
<223> OTHER INFORMATION: Codon-optimized crtZ gene from Agrobacterium
      aurantiacum

<400> SEQUENCE: 8
caattgtgct ctagaaagga ggaataaacc atgaccaact tcctgatcgt cgtcgccacc    60
gtgctggtca tggaactgac cgcgtatagc gtccatcgtt ggatcatgca tggtccgttg   120 ggttgggggct ggcacaagag ccatcatgaa gaacatgacc atgccttgga aaagaatgac   180
ctgtatggct tggtcttcgc cgtcatcgcc accgtcctgt tcaccgtcgg ctggatctgg   240
gctccagtct tgtggtggat cgccttgggc atgaccgtct atggcttgat ctacttcgtc   300
ctgcatgatg gcttggtcca tcaacgctgg ccgttccgct acatcccgcg caaaggctat   360
gcccgtcgct tgtatcaagc ccatcgcttg catcatgccg tcgaaggtcg tgatcattgc   420
gtcagcttcg gcttcatcta tgccccaccg gtcgacaaac tgaaacaaga cctgaagatg   480
agcggcgtct tgcgtgccga agcccaagaa cgcacctaat agatctggaa ttc          533

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gacatcgatg tcgaattcga gctcggtacc gatc                                   34

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
gacctcgtcg ctgttattag ttgactgtca gc                                     32

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
agatctcgga cgtcatcact cccacat                                           27

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gcatgcgcga ggtagacgtc gaacac                                            26

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
agatctttgc aacgggtatt cgacgaagg                                         29

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
gcatgcgcgg ccgccccgat gtttctggga aatcagc                                37

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
gcggccgcaa tcagcaagcg ctgcaagc                                          28

<210> SEQ ID NO 16
<211> LENGTH: 26
<212> TYPE: DNA
<213> ORGANISM: Artificial Sequence

```
<220> FEATURE:
<223> OTHER INFORMATION: Primer

<400> SEQUENCE: 16
gcatgcgttg cggatacagc ctgtcc                                          26

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
gcatgcctcg agtgctatcg tcgtcatact caggctttg                            39

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
ctcgagaatc agcaagcgct gcaagc                                          26

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
agatctatcc gattccggtc atgctgga                                        28

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
gcatgccttt ggtcatgatg tgagc                                           25

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
acgcgtggtg agggacaaga ttgtgg                                          26

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
gcatgctgct ttggttagcg atagcg                                          26
```

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
agatctccgt tctgtacact gatccg                                    26

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
agatctgcgg cgcccatttg ttgctgatag aatccggc                       38

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
gcggccgcgc aagccggcca acagggattc c                              31

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
gcggccgccg aatacctcga cattcaagc                                 29

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
agatctaact gtgcgagcgc cgtagc                                    26

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
gcatgccgac atctagttgt ccagc                                     25

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
agatcttggc gcttgatcga aatcgtcg                                              28

<210> SEQ ID NO 30
<211> LENGTH: 28
<212> TYPE: DNA
<213> ORGANISM: Artificial Sequence
<220> FEATURE:
<223> OTHER INFORMATION: Primer

<400> SEQUENCE: 30
gcggccgctg tcgtgcgaat gcatcagc                                              28

<210> SEQ ID NO 31
<211> LENGTH: 729
<212> TYPE: DNA
<213> ORGANISM: Agrobacterium aurantiacum

<400> SEQUENCE: 31
atgagcgcac atgccctgcc caaggcagat ctgaccgcca ccagcctgat cgtctcgggc           60
ggcatcatcg ccgcttggct ggccctgcat gtgcatgcgc tgtggtttct ggacgcagcg          120
gcgcatccca tcctggcgat cgcaaatttc ctgggcgtga cctggctgtc ggtcggattg          180
ttcatcatcg cgcatgacgc gatgcacggg tcggtggtgc cggggcgtcc gcgcgccaat          240
gcggcgatgg gccagcttgt cctgtggctg tatgccggat tttcgtggcg caagatgatc          300
gtcaagcaca tgcccatca ccgccatgcc ggaaccgacg acgaccccga tttcgaccat           360
ggcggcccgg tccgctggta cgcccgcttc atcggcacct atttcggctg gcgcgagggg          420
ctgctgctgc ccgtcatcgt gacggtctat gcgctgatcc ttggggatcg ctggatgtac          480
gtggtcttct ggccgctgcc gtcgatcctg gcgtcgatcc agctgttcgt gttcggcacc          540
tggctgccgc accgccccgg ccacgacgcg ttcccggacc gccacaatgc gcggtcgtcg          600
cggatcagcg accccgtgtc gctgctgacc tgctttcact ttggcggtta tcatcacgaa          660
caccacctgc acccgacggt gccgtggtgg cgcctgccca gcacccgcac caaggggac            720
accgcatga                                                                 729

<210> SEQ ID NO 32
<211> LENGTH: 489
<212> TYPE: DNA
<213> ORGANISM: Agrobacterium aurantiacum

<400> SEQUENCE: 32
atgaccaatt tcctgatcgt cgtcgccacc gtgctggtga tggagttgac ggcctattcc           60
gtccaccgct ggatcatgca cggcccctg gctggggct ggcacaagtc ccaccacgag            120
gaacacgacc acgcgctgga aaagaacgac ctgtacggcc tggtctttgc ggtgatcgcc          180
acggtgctgt tcacggtggg ctggatctgg gcgccggtcc tgtggtggat cgccttgggc          240
atgactgtct atgggctgat ctatttcgtc ctgcatgacg ggctggtgca tcagcgctgg          300
ccgttccgtt atatcccgcg caagggctat gccagacgcc tgtatcaggc ccaccgcctg          360
caccatgcgg tcgaggggcg cgaccattgc gtcagcttcg gcttcatcta tgcgccccg           420
gtcgacaagc tgaagcagga cctgaagatg tcgggcgtgc tgcgggccga ggcgcaggag          480
cgcacgtga                                                                 489

<210> SEQ ID NO 33

<211> LENGTH: 242
<212> TYPE: PRT
<213> ORGANISM: Agrobacterium aurantiacum

<400> SEQUENCE: 33

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Ile Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240

Thr Ala
```

<210> SEQ ID NO 34
<211> LENGTH: 162
<212> TYPE: PRT
<213> ORGANISM: Agrobacterium aurantiacum

<400> SEQUENCE: 34

```
Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

Met Thr Val Tyr Gly Leu Ile Tyr Phe Val Leu His Asp Gly Leu Val
                85                  90                  95
```

-continued

```
His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Met Ser Gly Val Leu Arg Ala Glu Ala Gln Glu
145                 150                 155                 160

Arg Thr
```

<210> SEQ ID NO 35
<211> LENGTH: 950
<212> TYPE: DNA
<213> ORGANISM: Pantoea stewartii

<400> SEQUENCE: 35

| | | |
|---|---|---|
| gaattcgccc ttgacggtct gcgcaaaaaa acacgttcac cttactggca tttcggctga | 60 |
| gcagttgctg gctgatatcg atagccgcct tgatcagtta ctgccggttc agggtgagcg | 120 |
| ggattgtgtg ggtgccgcga tgcgtgaagg cacgctggca ccgggcaaac gtattcgtcc | 180 |
| gatgctgctg ttattaacag cgcgcgatct tggctgtgcg atcagtcacg ggggattact | 240 |
| ggatttagcc tgcgcggttg aaatggtgca tgctgcctcg ctgattctgg atgatatgcc | 300 |
| ctgcatggac gatgcgcaga tgcgtcgggg gcgtcccacc attcacacgc agtacggtga | 360 |
| acatgtggcg attctggcgg cggtcgcttt actcagcaaa gcgtttgggg tgattgccga | 420 |
| ggctgaaggt ctgacgccga tagccaaaac tcgcgcggtg tcggagctgt ccactgcgat | 480 |
| tggcatgcag ggtctggttc agggccagtt taaggacctc tcggaaggcg ataaacccccg | 540 |
| cagcgccgat gccatactgc taaccaatca gtttaaaacc agcacgctgt tttgcgcgtc | 600 |
| aacgcaaatg gcgtccattg cggccaacgc gtcctgcgaa gcgcgtgaga acctgcatcg | 660 |
| tttctcgctc gatctcggcc aggcctttca gttgcttgac gatcttaccg atggcatgac | 720 |
| cgataccggc aaagacatca atcaggatgc aggtaaatca acgctggtca atttattagg | 780 |
| ctcaggcgcg gtcgaagaac gcctgcgaca gcatttgcgc ctggccagtg aacacctttc | 840 |
| cgcggcatgc caaaacggcc attccaccac ccaacttttt attcaggcct ggtttgacaa | 900 |
| aaaactcgct gccgtcagtt aacaattgag tgggcaggat tatgcaaccg | 950 |

<210> SEQ ID NO 36
<211> LENGTH: 3611
<212> TYPE: DNA
<213> ORGANISM: Pantoea stewartii

<400> SEQUENCE: 36

| | | |
|---|---|---|
| aaaactcgct gccgtcagtt aacaattgag tgggcaggat tatgcaaccg cactatgatc | 60 |
| tcattctggt cggtgccggt ctggctaatg gccttatcgc gctccggctt cagcaacagc | 120 |
| atccggatat gcggatcttg cttattgagg cgggtcctga ggcgggaggg aaccatacct | 180 |
| ggtcctttca cgaagaggat ttaacgctga atcagcatcg ctggatagcg ccgcttgtgg | 240 |
| tccatcactg gcccgactac caggttcgtt tcccccaacg ccgtcgccat gtgaacagtg | 300 |
| gctactactg cgtgacctcc cggcatttcg ccgggatact ccgcaacag tttggacaac | 360 |
| atttatggct gcataccgcg gtttcagccg ttcatgctga atcggtccag ttagcggatg | 420 |
| gccggattat tcatgccagt acagtgatcg acggacgggg ttacgcgcct gattctgcac | 480 |
| tacgcgtagg attccaggca tttatcggtc aggagtggca actgagcgcg ccgcatggtt | 540 |

-continued

| | |
|---|---|
| tatcgtcacc gattatcatg gatgcgacgg tcgatcagca aaatggctac cgctttgttt | 600 |
| ataccctgcc gctttccgca accgcactgc tgatcgaaga cacacactac attgacaagg | 660 |
| ctaatcttca ggccgaacgg gcgcgtcaga acattcgcga ttatgctgcg cgacagggtt | 720 |
| ggccgttaca gacgttgctg cgggaagaac agggtgcatt gcccattacg ttaacgggcg | 780 |
| ataatcgtca gttttggcaa cagcaaccgc aagcctgtag cggattacgc gccgggctgt | 840 |
| tcatccgac aaccggctac tccctaccgc tcgcggtggc gctggccgat cgtctcagcg | 900 |
| cgctggatgt gtttacctct tcctctgttc accagacgat tgctcacttt gcccagcaac | 960 |
| gttggcagca acagggtttt tccgcatgc tgaatcgcat gttgttttta gccggaccgg | 1020 |
| ccgagtcacg ctggcgtgtg atgcagcgtt tctatggctt acccgaggat ttgattgccc | 1080 |
| gcttttatgc gggaaaactc accgtgaccg atcggctacg cattctgagc ggcaagccgc | 1140 |
| ccgttcccgt tttcgcggca ttgcaggcaa ttatgacgac tcatcgttga agagcgacta | 1200 |
| catgaaacca actacggtaa ttggtgcggg ctttggtggc ctggcactgg caattcgttt | 1260 |
| acaggccgca ggtattcctg ttttgctgct tgagcagcgc gacaagccgg gtggccgggc | 1320 |
| ttatgtttat caggagcagg gctttacttt tgatgcaggc cctaccgtta tcaccgatcc | 1380 |
| cagcgcgatt gaagaactgt tgctctggc cggtaaacag cttaaggatt acgtcgagct | 1440 |
| gttgccggtc acgccgtttt atcgcctgtg ctgggagtcc ggcaaggtct tcaattacga | 1500 |
| taacgaccag gcccagttag aagcgcagat acagcagttt aatccgcgcg atgttgcggg | 1560 |
| ttatcgagcg ttccttgact attcgcgtgc cgtattcaat gagggctatc tgaagctcgg | 1620 |
| cactgtgcct tttttatcgt tcaaagacat gcttcgggcc gcgccccagt tggcaaagct | 1680 |
| gcaggcatgg cgcagcgttt acagtaaagt tgccggctac attgaggatg agcatcttcg | 1740 |
| gcaggcgttt tcttttcact cgctcttagt gggggggaat ccgtttgcaa cctcgtccat | 1800 |
| ttatacgctg attcacgcgt tagaacggga atggggcgtc tggtttccac gcggtggaac | 1860 |
| cggtgcgctg gtcaatggca tgatcaagct gtttcaggat ctgggcggcg aagtcgtgct | 1920 |
| taacgcccgg gtcagtcata tggaaaccgt tggggacaag attcaggccg tgcagttgga | 1980 |
| agacggcaga cggtttgaaa cctgcgcggt ggcgtcgaac gctgatgttg tacatacccta | 2040 |
| tcgcgatctg ctgtctcagc atcccgcagc cgctaagcag gcgaaaaaac tgcaatccaa | 2100 |
| gcgtatgagt aactcactgt ttgtactcta ttttggtctc aaccatcatc acgatcaact | 2160 |
| cgcccatcat accgtctgtt ttgggccacg ctaccgtgaa ctgattccg aaattttaa | 2220 |
| ccatgatggt ctggctgagg attttcgct ttatttacac gcaccttgtg tcacggatcc | 2280 |
| gtcactggca ccgaaagggt gcggcagcta ttatgtgctg cgcctgttc cacacttagg | 2340 |
| cacggcgaac ctcgactggg cggtagaagg accccgactg cgcgatcgta tttttgacta | 2400 |
| ccttgagcaa cattacatgc ctggcttgcg aagccagttg gtgacgcacc gtatgtttac | 2460 |
| gccgttcgat ttccgcgacg agctcaatgc ctggcaaggt tcggccttct cggttgaacc | 2520 |
| tattctgacc cagagcgcct ggttccgacc acataaccgc gataagcaca ttgataatct | 2580 |
| ttatctggtt ggcgcaggca cccatcctgg cgcgggcatt cccggcgtaa tcggctcggc | 2640 |
| gaaggcgacg gcaggcttaa tgctggagga cctgatttga cgaatacgtc attactgaat | 2700 |
| catgccgtcg aaaccatggc ggttggctcg aaaagctttg cgactgcatc gacgcttttc | 2760 |
| gacgccaaaa cccgtcgcag cgtgctgatg ctttacgcat ggtgccgcca ctgcgacgac | 2820 |
| gtcattgacg atcaaacact gggctttcat gccgaccagc cctcttcgca gatgcctgag | 2880 |

```
cagcgcctgc agcagcttga aatgaaaacg cgtcaggcct acgccggttc gcaaatgcac    2940
gagcccgctt ttgccgcgtt tcaggaggtc gcgatggcgc atgatatcgc tcccgcctac    3000
gcgttcgacc atctggaagg ttttgccatg gatgtgcgcg aaacgcgcta cctgacactg    3060
gacgatacgc tgcgttattg ctatcacgtc gccggtgttg tgggcctgat gatggcgcaa    3120
attatgggcg ttcgcgataa cgccacgctc gatcgcgcct gcgatctcgg gctggctttc    3180
cagttgacca acattgcgcg tgatattgtc gacgatgctc aggtgggccg ctgttatctg    3240
cctgaaagct ggctgaaga ggaaggactg acgaaagcga attatgctgc gccagaaaac    3300
cggcaggcct taagccgtat cgccgggcga ctggtacggg aagcggaacc ctattacgta    3360
tcatcaatgg ccggtctggc acaattaccc ttacgctcgg cctgggccat cgcgacagcg    3420
aagcaggtgt accgtaaaat tggcgtgaaa gttaacagg ccgtaagca ggcctgggat    3480 catcgccagt ccacgtccac cgccgaaaaa ttaacgcttt tgctgacggc atccggtcag    3540
gcagttactt cccggatgaa gacgtatcca ccccgtcctg ctcatctctg gcagcgcccg    3600
atctaggtac c                                                         3611
```

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37

```
gaattcgccc ttgacggtct                                                  20
```

<210> SEQ ID NO 38
<211> LENGTH: 50
<212> TYPE: DNA
<213> ORGANISM: Artificial Sequence
<220> FEATURE:
<223> OTHER INFORMATION: Primer

<400> SEQUENCE: 38

```
cggttgcata atcctgccca ctcaattgtt aactgacggc agcgagtttt                 50
```

<210> SEQ ID NO 39
<211> LENGTH: 50
<212> TYPE: DNA
<213> ORGANISM: Artificial Sequence
<220> FEATURE:
<223> OTHER INFORMATION: Primer

<400> SEQUENCE: 39

```
aaaactcgct gccgtcagtt aacaattgag tgggcaggat tatgcaaccg                 50
```

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40

```
ggtacctaga tcgggcgctg ccaga                                            25
```

<210> SEQ ID NO 41
<211> LENGTH: 8814
<212> TYPE: DNA
<213> ORGANISM: Pantoea agglomerans

<400> SEQUENCE: 41

```
accgcgaaga cagcaacgtg ctggagaccc gctttgagac ggaaccgggt cggtgctgat        60
caccgagtcg ctgaacagca cgcttgctgg ccggctgccg tggagcgaac tggcccgccg       120
catcgacggt attgagggcc acgtgacgct gaacgtcagc ctgcgtttcg gtaccgctgc       180
cgagacgcgc tccccgtgga gggcgaacac ctttaagggc gatgtgtttc acattgccga       240
tctgatggcg atgctgcgca ccagcgaaga cattgagatt acccactgcg acgatgaaaa       300
aattaccgcc cagctgatga cctcaccggg gtcgcgctcg ctggtcgccc tgctggtcac       360
cgagaaagag ccgctggcgg tgccggatct ctccgccatc gatgaccgca tcgaaaccag       420
ccaccttgcc tggtgcgact ggacccgcag cctcagctac cgcggtctct acgacaagca       480
cgtcaaacga tccgcgctgg cgctgaagtt tctctggtac tccccgaccg gcgcgctggc       540
ggcggcggcc accacctcgc tgccggaagg cattggcggg gagaaaaact acgactaccg       600
ctatgcctgg gtgcgcgatg cctgtctgat catcaaagcg ttcgtgttcc tcggtgcgct       660
ggaggactgc aaagccgcct ctcctggct gtcgaaaacc attattcgcc acgggcctga       720
gctgcgcgcc tgctatacgc tcgaaggtga cgaggtgccg gccgagtact atccgccgct       780
gcgcggatat cgggattccc gcccggtgcg ggtgggcaac aacgcccgca accagatcca       840
gctcagcatg tacggcgaca tgctcgccac cgcgcagctg tttatcgagg cgggacacgt       900
actggatctc gccaccctcg ccctgcttgg cgaactggcg aactgctgcg ccgacagctg       960
gcggcagaag gactccggca tctgggagtt accggacgag cagcactata cccactcgaa      1020
gatggcctgc tggctggcac tggatcgcgc cgtggcgatg gcagaacaga agcacatcga      1080
accgacctgg gtcgggcgct ggcagcgcga gcgcgatcgg atccgcgact ggatcgaaac      1140
ccactgctgg tcggagaaaa agcaggccta cgtgttttac gtcggggacg acgagcggct      1200
ggatgccgcc ctggcgctgg tgcacgacta cggcaacagc gtaaacccgc agcgtatgct      1260
ggccacctat cgcgccatca agcggagct gggacacgac acgcccatgc tctaccgcta      1320
cagcgaggtg aaaaggaag aaagcacctt tgtcgcctgc tcgttctggc tggtggaagc      1380
cctcgccgcg atgggtgaaa ccgacgaggc ccaggcggcc atgaccggca tcctcgagag      1440
gctctgcgac cggggcaatg ttgaaacttt taacgagatg tttgatgtgc gtaccgacga      1500
gtggcgcggc aaccttcctc aggggctgag ccatctggcg ctgatctgcg ccgcgcaggc      1560
gctttcggaa aaatgccgca acacgcgcga ctgacgcacg cgtagctaag gagaagacga      1620
tgaccatcag aggtatcgaa catattggta ttaccgtcgc cgacctcacc ggggcggagc      1680
ggttttcat cgaggcgctg gatgccagcg tgctctaccg catcgtgccg cccggcgcgg      1740
cggacaatgc catcagcggc gaccagatga cgcggctcaa tggctttccc ccggagatgc      1800
gggttaccgg cctggccatg ctgcgtctcg gcaacggctg caatattgag ctgtttgaga      1860
tcgatcccgg cgtggcagac gcgcccggaa atatcagcca ggcgggcctg aaccacctgt      1920
cggtttacgt ggacgacatt cagcaggccg gcgcacgggt aaaagcacag gcgccacgc      1980
tgtttgacgg gccgagcgac tgctttgctc aggaagaggg ccgcggcaac cagacctggt      2040
tctgccgcac gccttttggc ctgctgattg aactcatctc ccttccctcg ccgcttcgct      2100
acgatgcgca ggcgcagcaa accgctggga tcccccagcg ctgacaggcc tctctcacgc      2160
gggcatcgcc cgcgttgtca taccctcgtc accgtcctga caaaaattaa caataaattt      2220
tcattttca gccagacttt aagcacatag cgtcgccatg acatttattt tcatctaaac      2280
```

```
ctatacaaga aaaacattga tgtataactt tgcataccgc tgcacacagg ctcagactgc   2340
gacacccgtt gcgggtcagc gctatttcca tttcatctgc gagacgccgg gtaccaacca   2400
tgacaagacc ctttgaaaca catcccggtc acgacgggga actgcatgag ctgcacgctg   2460
ccctgcaacg tcgcctggat gaactgctgc ccgttggcga tgagcgggat cgggtcagca   2520
gcgcaatgcg cgaaggcgta ctggcaccgg ggaaacgcat tcgcccgctg ctcctgatcc   2580
tcgccgcccg cgacctcggc tgcgatcgcg accaccccgg cctgctggat atggcctgtg   2640
cggtggaaat ggtgcacgcc tcgtcgctga tcctcgacga tattccctgc atggataacg   2700
cggcgctccg gcgcggtcgc cctaccattc atcgccagta tggtgaagac gtggcaattc   2760
tcgctgcggt agcgttgctc agcagcgcct ttggcgtgat ggtcgcggcg cagggattgt   2820
ctcccgagtg ccgcagccag gcggtggcgg agctgtcgat ggcggtcggt acccagggtc   2880
tggtgcaggg tcagtataag gatctgcgtg aaggcaccgc cccgcgcagc gccgaggaga   2940
tcgccaccac caacgaactg aaaaccagcg tgctgtttgg tgccacgctg caaatcgcgg   3000
ccctggcggc aggcgcctcg ccggcggcgc gccagaaaat gcgctgctttt gcgcaggatt   3060 taggccaggc gttccagctg ctggacgatc tggcggacgg ccatgccggg accggcaaag   3120
acatcaataa ggacgcgggt aagtccacgc tggtggcgat gctcggcagc gacgcggtgc   3180
gcgagcggct cgacacccat ctgcgccgcg cagacgccca ttttttcacgc gcctgcggaa   3240 aaaaccaggc cacgcgacgc tttatgcacg cctggttttc aaaacagctg gccgcgttta   3300
gctgagcaac ggatacaccc cggtaatatt tgtggagatc acatgaagga cgcgcatctg   3360
gttcagcgta aaaatgacca cctggatatc gtgctgcacc ctgaccgggc gatgagtacc   3420
attcgcaccg gatttgacgc ctggcgtttt gaacactgcg ccctcccgga gctggatctc   3480
gacggtatcg atctctccac caccctgttt tcccgcccgc tgaaagcccc ggtgctgatc   3540
agctccatga ccggcggcgc ggcgcgcgcc agagacatta accgtcatct ggcccaggcg   3600
gcgcaaaccc ttgggctggc gatgggcgtc ggttcccagc gcgtggcgct ggaggacggc   3660
gcgcagcacg ggctggatgc ccagctacgc catatcgccc cggacgtgcc gctgctggct   3720
aaccttggcg cggcgcagat ccgcggtgcg caggggctgg actacgcccg cgcgcgggtg   3780
gacatgatcg acgccgacgc gttaattgtg catctgaacc cgctgcagga ggcgctccag   3840
ggcggcggcg atcgcgactg gcgcggcatc ctcaacgcca ttgcgcagct ggtgcgcgac   3900
ctgccggtac cggtggtggt taaagaggtg ggcgccggga tctccccgga cgttgcctgc   3960
cgactggcga acgtcggcgt ggcgatgatc gacattgccg gcgcgggcgg aaccagctgg   4020
gcggcggtgg aagctgaacg cgccccgacc cccgaggcgc gaaatgtggc gatggccttt   4080
gccgactggg gcattcctac tgccgatgcg ctgcgtcgcg tccatcttgc gctgcctgat   4140
atcccgctta tcgcctccgg cggcatcgcc aacggcattg acgcagcaaa agccatcgcg   4200
ctgggtgcag atcggtgggg ccaggccgcg gcggtgctgg cgcatgccaa cgcctccggc   4260
gacgcggcaa ttgcccacttt ccgcaccctg attacgcagc tgcggatcgc ctgtttctgt   4320
accggcagtg caaacctgca ggcgttgcga cacgccacgc tgcttccggt caacggcggc   4380
gcatccctgt gacgcagtac ggtgccttat accggggagc ggtatgaaaa aatgggatct   4440
gattctggtc ggcgcgggc tggccaacgg gcttatcgcc tggcgactaa agcagcgtca   4500
tccgacgctt gctgtattaa tgctggagtg cggcgacgcg cccggcggaa accacacctg   4560
gtcctttcac caaacgata tcacgccagc ccagcacgcc tggctggcgc cgctggtggc   4620
ccatcgctgg gacgggtacg acgtccactt tccgaacgtg tcgcgcaccc tgcatgacgg   4680
```

```
ctacctgacc atcacctcca cgcgttttgc ccaagcgatg cgcgggctga tgaaagagaa    4740
tttgctgaca aacgtgaccg tgtcacgggt gagcgggcag gaagtaaccc tcagcgacgg    4800
acgacgcttt accgccgggg cggtgattga tggccgcggc tatcagccct cgccgcacct    4860
cagcattggc tatcaggcgt tcatcggcca ggagtggcaa ctgaccgcgc cccacgggtt    4920
aacgcgcccg atcctgatgg atgcccgcgt cgcccagggc aacggctacc gctttgtcta    4980
taccctgccg ctcagcgccg acaccctgct tatcgaagac acgcactaca ttgacggccc    5040
gacgctcgac gccgattcag cccgcgcgcg gattgccgat tacgcccgcc agcagggctg    5100
gcagcttgcg cggctggtgc gtgaggaaca gggggcgctg ccgatcaccc tgtccggcga    5160
tccgccgcc ttctggcacc agttccatca tcagccggtc agcggcctgc gcgccggtct    5220
gttccatgcc accaccggct attcgctgcc gctggcggtt cggctggcgg accgcattgc    5280
caacgcgccg ggactgcatc agggcgcgct ctatcagctg atcgccgatt tcgcggcgcg    5340
ccactggcag acacaacgct ttttccgcct gcttaaccgc atgcttttcc tggccggcac    5400
acccgaccag cgctggcgcg tgatgcagcg gttttaccag cttgacgagc agctgatcgc    5460
ccgttttat gccggccagc ttcgctccgc cgaccgcgcg cgcctgctgc ttggcaaacc    5520
gccggtgccg attgtcgggg cgatcaaagc cctgctccac actcattctt ctctgcgagc    5580
ccatcataaa tgaaacaaac cattgtaatt ggcgccgggt tcggcggact ggcgctggcg    5640
attcgcctcc aggcggcggg cattcctacc acgctgctgg agagccgcga caaacccggc    5700
ggccgcgcct atgtctacga agatcgcggc tttacctttg atgcgggtcc caccgtcatc    5760
accgatccct ccgccattga ggagctgttc accctcgccg gaaaacggct gaaggactac    5820
gttgagctga tgccggtgac gccgttctat cgcctgtgct gggaagacgg caaggttttc    5880
gactacgcca acgatcaggc ggcgcttgag tcgcagatcg ccgcgtttaa cccgaacgac    5940
gtggcgggct atcaccgctt cctcgactac tcccgggcgg tgtttgccga aggctatctg    6000
aagctcggcg cggtgccgtt tctctcgttt cgcgacatgc tgcgcgccgg tcctcaactg    6060
gcgcggctgc aggcatggcg cagcgtgtac gacaaagtgt cggcctacgt ggaagacgag    6120
cacctgcggc aggcattttc gttttcactcg ctgctggtgg gcggcaaccc gttctccacg    6180
tcttctatt acaccctgat ccacgccctg gagcgggaat ggggcgtctg gttcccgcgc    6240
ggcggcaccg gtgcgctggt tcagggcatg gtgaagctgt ttcaggatct tggcggcacc    6300
ctcacccttta acgctcaggt tgagcggctg gagacggtgg acaatcaggt gaaggccgtg    6360
catctggtta acgggcagcg gctggaggct gcggcggtgg cctcgaacgc ggacgtggta    6420
aataccttatg cccgactgct cggccatcac ccgcacggcg ccgctacggc caaaaagctg    6480
aaacgcaagc gcatgagcaa ctcgctgttc gtgctctatt ttggcctgga tcaccatcac    6540
acccagctgg cgcaccatac cgtctgcttt ggcccgcgtt ataaagcgct aatcgatgaa    6600
attttcagcg ccgacaccct gtcggaagat ttttcgctct atctgcatgc gccctgcgta    6660
accgacccgt cgctggcccc gccggggtgc ggcagctact atgtgctcgc gccggtgccg    6720
cacctcggta acgcccgct cgactggagc gtggaagggc cgcgtctgcg ggatcgcatt    6780
tttgattatc tcgaagcgcg ctatatgccg gggctgcgct cccagctggt gacgcaccgc    6840
atgttcacgc cggaagattt tcgcgatacg ctcgatgcct ggcaggggtc agcgttttca    6900
ctggagccga tcctcaccca gagcgcctgg ttccggccgc acaaccgcga cagcgtggtt    6960
gataacctct acctggtcgg cgccggaacg catcccggcg ctggcgtgcc gggcgtgatc    7020
```

-continued

```
ggatccgcca aggcaacggc ccagttaatg ttaaaggatt tagcgtaatg tcccagccgc    7080
ttctcgaaca cgccagcgcc accatgaccg ccggttctaa aagtttcgcc accgcctcaa    7140
agctgtttga caaacgcacc cggcgcagcg cgctgatgct ctatacctgg tgccgctact    7200
gcgacgatgt tatcgacgga caggtggtgg gttttgctgc cccgaccgag cagagcgaca    7260
cgcccgaggc gcgcctgcaa cggctgcgta agatgacgcg ccgcgcctac gacgggaaa     7320 ccatgcaaga gccgccgttc gccgcctttc aggaggttgc cctcgcccat gccattccgc    7380
ctactcaggc cttcgaccac ctggaaggct atgcgatgga cgtgcgcaac gagcgctatt    7440
acagcctcga tgatacgctc cgctactgtt atcacgtggc gggcgtggtc ggcctgatga    7500
tggccagggt gatgggagtg cgggacgaag ccacgctgga tcgcgcctgc gatctgggca    7560
ttgccttcta gctcaccaat atcgccaggg atatcgttga cgatgcgcag gtgggacgct    7620
gctacctgcc gcagcagtgg ctggcggaag tcggactcaa tgaacagacc tgcaccgtgc    7680
gggccaaccg tccggcgctg gcgcgtctgg cagcgcggct ggtgaccgag ctgagccct    7740 attatcagtc agcgcttgcc gggctggggg atctgccccct gcgctccgcc tgggcgattg    7800
ccaccgcgca cggggtgtat cgtgagatcg gggtgaaggt gctgatggcg ggtgaaaaag    7860
catgggatac cgccagggc acgacgcgcg cggagaagct ggcgctggtt atttccggcg     7920 cgaagcagg gatggcttcc cggaaggcga gctggccgcc gcgcgatccg cacctctggc    7980
agcgcccgcg ctagcgggtc tgccgttacg ttcgcgcagc accgcctgca gcttgtccac    8040
cggtggggcg tagataaacc cgaaggagac gcacccttcg cgcccccgca ccgcgtgatg    8100
cagccggtgt gccatgtaga ggcggcgcag atagccgcgg cgcggcacgt aacggaacgg    8160
ccagcgctgg tggactaaac catcgtgaac gataaagtag atcacgccgt agccggtcat    8220
tcccgcgcca atccactgaa gcggccagta cccttcgctg cccgcgtaaa tcagcgcaat    8280
ggccagtagc gcaaacacca ccgcatagag atcgttacgc tcaaacgccc ctttgcgcgg    8340
ggtatggtgc gaatgatgcc agccccatcc ccagccgtgc atgatgtact tgtgtgcgaa    8400
cgttgccacc ccttccatga tgatgatagt cagtagcacg atcccggtat tccacaacgc    8460
aagcataggt ttttcctgta gttgacagcc cctaaagcgt agcctggaat gccaggaaac    8520
ataagcgtaa cctcggggat aatgcgcttt tcaggcgtaa aagcatttat gacaattatt    8580
catcgcgcca cgttcacgcc gtgacgccct gctcaccgcg cggcagcagc cgcatcggct    8640
gataaacgcg cccggtttct gcgcgtcatc gcccggtgtg cgcggcgtca acgcaataaa    8700
acttactttc aaaaggcggc ccgaaaaggc taccttttt tattcttgtc atatactcga    8760
tctaacctga attatcgccg taacgtaccg cttcttttga ggtaatcccg gagc          8814
```

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
gaattcacta gtcgagacgc cgggtaccaa ccat                                34

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
gaattctagc gcgggcgctg ccaga                                    25

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
gccaattgaa ggaggaataa accatg                                   26

<210> SEQ ID NO 45
<211> LENGTH: 42
<212> TYPE: DNA
<213> ORGANISM: Artificial Sequence
<220> FEATURE:
<223> OTHER INFORMATION: Primer

<400> SEQUENCE: 45
gcgaattcag atcttgctct agatcacgcg gtgtcgcctt tg                 42

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
actagtaagg aggaataaac catgagcgcc                               30

<210> SEQ ID NO 47
<211> LENGTH: 33
<212> TYPE: DNA
<213> ORGANISM: Artificial Sequence
<220> FEATURE:
<223> OTHER INFORMATION: Primer

<400> SEQUENCE: 47
gctagctgta cattaggtgc gttcttgggc ttc                           33

<210> SEQ ID NO 48
<211> LENGTH: 29
<212> TYPE: DNA
<213> ORGANISM: artificial sequence
<220> FEATURE:
<223> OTHER INFORMATION: primer

<400> SEQUENCE: 48
agatcttcgg tttcgatcag ctcgatgct                                29

<210> SEQ ID NO 49
<211> LENGTH: 46
<212> TYPE: DNA
<213> ORGANISM: artificial sequence
<220> FEATURE:
<223> OTHER INFORMATION: primer

<400> SEQUENCE: 49
gcatgcacgc gttgtcgtgc gaatgcatca gcacgttgca atgtcg             46

<210> SEQ ID NO 50

```
<211> LENGTH: 26
<212> TYPE: DNA
<213> ORGANISM: artificial sequence
<220> FEATURE:
<223> OTHER INFORMATION: primer

<400> SEQUENCE: 50
acgcgtggtg agggacaaga ttgtgg                                          26

<210> SEQ ID NO 51
<211> LENGTH: 27
<212> TYPE: DNA
<213> ORGANISM: artificial sequence
<220> FEATURE:
<223> OTHER INFORMATION: primer

<400> SEQUENCE: 51
gcatgccatc taaagtccag gcccttta                                        27

<210> SEQ ID NO 52
<211> LENGTH: 28
<212> TYPE: DNA
<213> ORGANISM: artificial sequence
<220> FEATURE:
<223> OTHER INFORMATION: primer

<400> SEQUENCE: 52
ccatggccaa caccaaacac atcatcat                                        28

<210> SEQ ID NO 53
<211> LENGTH: 48
<212> TYPE: DNA
<213> ORGANISM: artificial sequence
<220> FEATURE:
<223> OTHER INFORMATION: primer

<400> SEQUENCE: 53
agtactccgc atatgtcagg ctttggcttt ggcttttttc agccaggc                  48
```